(12) United States Patent
Messier et al.

(10) Patent No.: US 7,462,460 B2
(45) Date of Patent: Dec. 9, 2008

(54) METHODS FOR IDENTIFYING AGENTS THAT INCREASE THE P44 FUNCTION OF MICROTUBULE ASSEMBLY OR RESISTANCE TO HCV INFECTION

(75) Inventors: Walter Messier, Longmont, CO (US); James Sikela, Englewood, CO (US)

(73) Assignee: Evolutionary Genomics, Inc., Lafayette, CO (US)

( * ) Notice: Subject to any disclaimer, the term of this patent is extended or adjusted under 35 U.S.C. 154(b) by 0 days.

(21) Appl. No.: 11/058,065

(22) Filed: Feb. 15, 2005

(65) Prior Publication Data
US 2005/0164174 A1    Jul. 28, 2005

Related U.S. Application Data

(60) Division of application No. 10/098,600, filed on Mar. 14, 2002, now Pat. No. 6,866,996, which is a continuation-in-part of application No. 09/942,252, filed on Aug. 28, 2001, now abandoned, which is a continuation-in-part of application No. 09/591,435, filed on Jun. 9, 2000, now Pat. No. 6,280,953, which is a continuation-in-part of application No. 09/240,915, filed on Jan. 29, 1999, now Pat. No. 6,228,586.

(60) Provisional application No. 60/098,987, filed on Sep. 2, 1998, provisional application No. 60/073,263, filed on Jan. 30, 1998.

(51) Int. Cl.
*G01N 33/53* (2006.01)

(52) U.S. Cl. ...................................... 435/7.1

(58) Field of Classification Search ................. 530/350; 514/12; C12N 15/12
See application file for complete search history.

(56) References Cited

U.S. PATENT DOCUMENTS

| 5,602,005 A | 2/1997 | Herr et al. |
| 5,965,352 A | 10/1999 | Stoughton et al. |

FOREIGN PATENT DOCUMENTS

| EP | 120658 | 3/1984 |

(Continued)

OTHER PUBLICATIONS

Kitamura et al., Induction of the human gene for p44. a hepatitis-C-asociated microtubular aggreagte protein, by interferon-alpha/beta, Eur. J. Biochem., 224, 877-833 (1994).*

(Continued)

*Primary Examiner*—Kathleen Kerr Bragdon
*Assistant Examiner*—Agnes B. Rooke
(74) *Attorney, Agent, or Firm*—Swanson & Bratschun, L.L.C.

(57) ABSTRACT

The present invention provides methods for identifying evolutionarily significant polynucleotide and polypeptide sequences in human and/or non-human primates which may be associated with a physiological condition, such as enhanced resistance to HCV infection. The invention also provides methods for identifying evolutionarily significant polynucleotides with mutations that are correlated with susceptibility to diseases, such as BRCA1 exon 11. The methods employ comparison of human and non-human primate sequences using statistical methods. Sequences thus identified may be useful as host therapeutic targets and/or in screening assays.

10 Claims, 31 Drawing Sheets

FOREIGN PATENT DOCUMENTS

| WO | WO 99/13075 | * | 3/1999 |
| WO | WO 00/12764 | | 3/2000 |
| WO | WO 99/39006 | | 7/2000 |

OTHER PUBLICATIONS

Alter et al. (1984) Science 226:549-552.
Burger et al. (1994) J. Mol. Evol. 39:255-267.
Edwards et al. (1995) Molecular Ecology 4:719-729.
Endo et al. (1996) Mol. Biol. Evol. 13:685-690.
Fournier et al. (1988) J. Gen. Virol. 79:2367.
Fultz et al. (1986) Journal of Virology 58:116-124.
Gibbons (Sep. 1998) Science 281: 1432-1434, website www.sciencemag.org.
Goodman et al. (1990) J. Mol. Evol. 30:260-266.
Goodwin et al. (1996) Mol. Biol. Evol. 13:346-358.
Herbert et al. (1996) Mol. Biol. Evol. 13:1054-1057.
Hughes (1997) Mol. Biol. Evol. 14:1-5.
Hughes and Nei (1988) Nature 335:167-170.
Huttley et al. (2000) Nature Genetics 25:410-13.
Jaeger et al. (1994) Immunogenetics 40:184-191.
Jenkins et al. (1995) Proc. R. Soc. Lond. 261:203-207.
Kitamura et al. (1994) Eur. J. Biochem. 224:877-83.
Kreitman and Akashi (1995) Annu. Rev. Ecol. Syst. 26:403-422.
Lee and Vacquier (1992) Biol. Bull. 182:97-104.
Lee et al. (1998) Aids Research and Human Retroviruses 14:1323-1328.
Li (1993) J. Mol. Evol. 36:96-99.
Li (1997) in Molecular Evolution, Sinauer Associates, Inc. Pub., Sunderland, MA, Table of Contents.
Li et al. (1985) Mol. Biol. Evol. 2:150-174.
Lienert and Parham (1996) Immunol. Cell Biol. 74:349-356.
Lyn et al. (1995) Gene 155:241-245.
Malcolm et al. (1990) Nature 345:86-89.
McDonald and Kreitman (1991) Nature 351:652-654.
Messier and Stewart (1994) Current Biology 4:911-913.
Messier and Stewart (1997) Nature 385:151-154.
Metz and Palumbi (1996) Mol. Biol. Evol. 13:397-406.
Nakashima et al. (1995) Proc. Natl. Acad. Sci. USA 92:5605-5609.
Nei (1987) in Molecular Evolutionary Genetics, Columbia University Press Pub., New York, NY, Table of Contents.
Nei and Hughes in Evolution at the Molecular Level, Sinauer Associates, Sunderland, MA, pp. 222-247 (1991).
Niewiesk and Bangham (1996) J. Mol. Evol. 42:452-458.
Novembre et al. (1997) Journal of Virology 71:4086-4091.
Parham and Ohta (1996) Science 272:67-74.
Patzwahl et al. (2000) J. Virology 75(3):1332-38.
Rumin et al. (199) J. Gen. Virology 80:3007.
Sharp (1997) Nature 385:111-112.
Swanson & Vacquier (1995) Proc. Natl. Acad. Sci. USA 92:4957-4961.
Swanson and Vacquier (1998) Science 281:710-712.
Wettstein et al. (1996) Mol. Biol. Evol. 13:56-66.
Whitfield et al. (1993) Nature 364:713-715.
Wolinsky et al. (1996) Science 272:537-542.
Wu et al. (1997) J. Mol. Evol. 44:477-491.
Xu et al. (1997) Human Mol. Genetics 6(7):1057-62.
Yang (1998) Mol. Biol. Evol. 15:568-573.
Zhou and Li (1996) Mol. Biol. Evol. 13:780-783.
Dennis (1999) Nat. Gen. 22:10.
Favre et al. (2001) CR Acad, Sci. 324:1141-1148.
Galun et al. (1995) J. Infectious Diseases 172:25-30.
Hacia et al. (Feb. 1998) Nat. Gen. 18:155-158.
Labonte et al. (2002) J. Med. Virol. 66:312-319.
Lanford et al. (1991) J. Med. Virology 34:148-153.
Mercer et al. (Aug. 2001) Nat. Med. 7(8):927-933.
Shen et al. (1998) Oncogene 17:3115-3124.
Shimizu et al. (Apr. 1985) Med. Sci. 82:2138-2142.
Takahashi et al. (1990) J. General Virology 71:2005-2011.
Thompson et al. (Apr. 1995) Nat. Gen. 9:444-450.
Walker (1997) Springer Semin Immunopathology 19(1):85-98.
Xu et al. (Mar. 1999) Mol. Cell 3:389-395.
Xu et al. (May 1999) Nat. Gen. 22:37-43.

* cited by examiner

```
HUMAN:      1441 AAGATCAAGAAATACAGAGACTACAACAGGCCCCAAAAAGGGACCCCCATGAAACCGAACACA
                 -:-:-:-:-:-:-:-:-:-:-:-:-:-:-:-:-:-:-:-:-:-:-:-:-:-:-:-:-:-:-:-:
CHIMPANZEE:      AAGATCAGGAAATACAGAGACTACAACACAGGCTCAAAAAGGGACCCCATGAAACCGAACACA
                  K  I  R  K  Y  R  L  Q  Q  A  Q  K  G  T  P  M  K  P  N  T

CAAGCCACGCCTCCCTGA    SEQ ID.: 1
                 -:-:-:-:-:-:-:-:-:
                 CAAGCCACGCCCTCCCTGA   SEQ ID.: 2
                  Q  A  T  P  P  ^ ^   SEQ ID.: 3
```

FIG. 2 (CONT.)

```
1515 ICAM      GORILLA
CAG ACA TCT GTG TCC TGT CCA CCC CGG GGA GGC TCC GTG CTG ACA
TGC AGC ACC TGT TGT GAC CAG CAG AAA CCC TTG TTG CCT CAA AAG
GAG TTG CTC CTG ATG GGG AAT AAC ACC CCG AAT GCT GTG AAA GAT
AGC CAA CCA TAC TCA GAA TGC CCT GAT GTG CAG CTC ACA ACC TTC CTC
ACC GTG TAC TGG ACT CCA GAA CTG GTG GAG GTG TCT TGG CAG CCA GTG
GGC AAG GAC CTT ACC CGT TGC CAG GAG CTG AAA CGG GCA AAC CTC ATC
GTG GTG CTG GGG GAG GTG CCG GAG CTG TTC TGC CCC GCC
ACT GAA CTG CAA ACG CTG CCC GTG CAA GGG CTG ACT GAG CCT CGG GTC GAG
CAG CTC TTT GTC GCG CCA GCG GTC CTT TGT GAC CCT CTG CCA GTC TCG GAG
GAG GTG GAC ACG CAG GTC GTC ACT TGT CCC TGG CAG AGG TTC CCA GAA AAC
GCC CAG GTC CAC CTG ACT CTG GGG GAC TTG AAC CCC ACA GTC GAC TAT GGC AAC
GAC TCC TTC TCA GCC AAG GCC CAG AGT GTG ACC CAG GAC GAG ACC GTG ACC TGG
CTG ACG TGT GCA GTA ATA CTG GGG ACC AGC CAG ATC CAG CAG AAG GTC AGG GAG AGC CCC TGG TAT CTG ACC CGG GAT GTC GAC AGG GCA CTG ATC CGG GCC ATC GAT CTG CCC GAG TGG TCC CCG CAG AGC CCG AAG CAA AAT GAG CAG GAT CAG GAG ACC CCG GCT GTG CCC ACC GAG GGT TGA GCC CCT CGG TGC CGG GGC CTA GGA AAG GAC GCG ACC CGA CCA TGG AAA AAC CCA AGA CTC ACA TCA GGG GAG GAG GTC AGG GAG GGG GAG CAT AGA AGA CGA AAG GAG TCA GAT CGA CTC CAA GAT TGC GAA AAT GGC ATC GAT CAT GGC GAT GAG AGC TGT GGG ATG ATG AAC CTC CCC AGA GAA TGG TCT CCA GGC AGC GAG GAA TGT AAG GTA TGC CTC CCA GCA GCG CTC AGC AGA ATG GAG GAA TGT AGA GAA CAA ACT AAG TGC GAG GAT CAA GAT GGA GGG TAC GGC GGG CCT GGC CAC TTC CGT GGC GTC GCT CAT AAT CCC CCC GGG AAT CGT CAG GTC GCA GCC GCA GTC GAT GGT TCC AAC ACC GTC AGA GAG GGC AAG CTC TAG CCC ATC CCC GTG CAT AGA ATC CCA CAG CCC CAA GAC GCC TTC GTA AAG ACG AAG CAA ATA GCG ACG CAA GCA CTA AGA TAC AAA CAT TAC GCA CGC AAA CCT GGG CCC TAG GTA CGG ACA
```

(SEQ ID NO: 4)

Fig. 3

```
1515 ICAM    ORANG
CAC ACA TCT GTG TCC TCC GCC AAC GTC TTC CTG CCC CGG GGA GGC TCC GTG CTA GTG AAT
TGC AGC ACC TCC TGT GAC CAG CCC AAC ACC TTG TTG AAG ATG TTG GGC ATA GAG CTG CCT CAA GAA AAG
GAG TTG CTC CCG GGG AAC TCA GAA CTG GAT TGC CCT AAT GCT GTG AAA ACC TTC CTC
AGC CAA CCA TAC TGC ACT CCA GAA CGG TGC GTG CAG GAG CTC TCT TGG CAG CCA GTG
ACC GTG AAG AAC CTT ACC ACC CTA CGC GAG GAG AGC GCA CCC CGG GCC AAC CTC ACC
GGC AAG AAC TTG CTC TGT CGT GGG CTG GAG AGC GGT GCA CCA GGA GTG GGG GAG CCC GCC
GTG GTA TTG CTC ACG CGT

Fig. 5A (SEQ ID NO:6)

| | QTSVSPSKVI | LPRGGSVLVT | CSTSCDQPKL | LGIETPLPKK | ELLLPGNNRK |
|---|---|---|---|---|---|
| Human J03132    | .......... | .......... | .......... | .......... | .......... |
| Human X06990    | .......... | .......... | .......... | .......... | .......... |
| Human X59286-8  | .......... | .......... | .......... | .......... | .......... |
| Human #4        | .......... | .......... | .......... | .......... | .......... |
| Human #7        | .......... | .......... | .......... | .......... | .......... |
| Human #8        | .......... | .......... | .......... | .......... | .......... |
| Human M24283    | .......... | .......... | ....M..... | .......... | .......... |
| Human U86814    | .......... | .......... | ....D..... | .......... | .......... |
| Chimp M86848    | ....P..... | .Q........ | ....D..... | .......... | ....G..W.. |
| Chimp #1        | ....P..... | .Q........ | ....T..... | .......... | ....G..W.. |
| Gorilla #1      | ....P..... | .......... | ....T..... | .......... | ....L..Q.. |
| Gorilla #2      | ....P..... | .......... | .......... | .......... | ....L..Q.. |
| Orang           | H...SAN.F. | ........N. | ....T..... | .......... | ...PG..W.. |

| | VYELSNVQED | SQPMCYSNCP | DGQSTAKTFL | TVYWTPERVE | LAPLPSWQPV |
|---|---|---|---|---|---|
| Human J03132    | .......... | .......... | .......... | .......... | .......... |
| Human X06990    | .......... | .......... | .......... | .......... | .......... |
| Human X59286-8  | .......... | .......... | .......... | .......... | .......... |
| Human #4        | .......... | .......... | .......... | .......... | .......... |
| Human #7        | .......... | .......... | .......... | .......... | .......... |
| Human #8        | .......... | .......... | .......... | .......... | .......... |
| Human M24283    | .......... | .......... | .......... | .......... | .......... |
| Human U86814    | .......... | .......... | .......... | .....????? | ?????????? |
| Chimp M86848    | .......... | .......... | .......... | .......... | .......... |
| Chimp #1        | .......... | .......... | .......... | .......... | .......... |
| Gorilla #1      | .......... | .......... | .......... | .......... | .......... |
| Gorilla #2      | .......... | .......... | .......... | .......... | .......... |
| Orang           | M......... | .......... | ....A..... | .......... | .......... |

| | GKNLTLRCQV | EGGAPRANLT | VVLLRGEKEL | KREPAVGEPA | EVTTTVLRR |
|---|---|---|---|---|---|
| Human J03132    | .......... | .......... | .......... | .......... | ......... |
| Human X06990    | .......... | .......... | .......... | .......... | ......... |
| Human X59286-8  | .......... | .......... | .......... | .......... | ......... |
| Human #4        | .......... | .......... | .......... | .......... | ......... |
| Human #7        | .......... | .......... | .......... | .......... | ......... |
| Human #8        | .......... | .......... | .......... | .......... | ......... |

| | | | | | | |
|---|---|---|---|---|---|---|
| Human M24283   | ?????????? | ?????????? | ?????????? | ?????????? | ?????????? | ?????????? |
| Human U86814   | ..D....... | .......... | .......... | ........E. | .......... | .........E. |
| Chimp M86848   | ..D....... | .......... | .......... | ........E. | .......... | .........E. |
| Chimp #1       | ..D....... | ........I. | .......... | .......... | .......... | .......P.EK |
| Gorilla #1     | ..D....... | ........I. | .......... | .......... | .......... | .......P.EK |
| Gorilla #2     | .......... | .......... | .......... | .......... | .......... | .......... |
| Orang          | .......... | .......... | .......... | ........E. | ......S.Q. | ....A...A.K |

| | | | | | | |
|---|---|---|---|---|---|---|
| Human J03132   | DHHGANFSCR | TELDLRPQGL | ELFENTSAPY | QLQTFVLPAT | PPQLVSPRVL | |
| Human X06990   | .......... | .......... | .......... | .......... | .......... | |
| Human X59286-8 | .......... | .......... | .......... | .......... | .......... | |
| Human #4       | .......... | .......... | .......... | .......... | .......... | |
| Human #7       | .......... | .......... | .......... | .......... | .......... | |
| Human #8       | .......... | .......... | .......... | .......... | .......... | |
| Human M24283   | ?????????? | ?????????? | ?????????? | ?????????? | ?????????? | |
| Human U86814   | .......... | .......... | ....Q....H | .......... | .......... | |
| Chimp M86848   | .......... | .......... | ....Q....H | .......... | .......... | |
| Chimp #1       | .......... | .......... | ....K..... | .......... | .......... | |
| Gorilla #1     | .....L.... | .......... | ....K..... | .......... | .......... | |
| Gorilla #2     | .....L.... | .......... | .........H | .......... | .......... | |
| Orang          | ..D....... | .......... | .......... | .......... | .......... | |

| | | | | | | |
|---|---|---|---|---|---|---|
| Human J03132   | EVDTQGTVVC | SLDGLFPVSE | AQVHLALGDQ | RLNPTVTYGN | DSFSAKASVS | |
| Human X06990   | .......... | .......... | .......... | .......... | .......... | |
| Human X59286-8 | .......... | .......... | .......... | .......... | .......... | |
| Human #4       | .......... | .......... | .......... | .......... | .......... | |
| Human #7       | .......... | .......... | .......... | .......... | .......... | |
| Human #8       | .......... | .......... | .......... | .......... | .......... | |
| Human M24283   | ?????????? | ?????????? | ?????????? | ?????????? | ?????????? | |
| Human U86814   | .......... | .......L.. | .......... | .......... | .......... | |
| Chimp M86848   | .......... | .......L.. | .......... | .......... | .......... | |
| Chimp #1       | ?????????? | ?????????? | ?????????? | ?????????? | ?????????? | |
| Gorilla #1     | .......... | .......... | .......... | .......... | .......... | |

Fig. 5B

|              | VTAEDEGTQR | LTCAVILGNQ | SQETLQTVTI | YSFPAPNVIL | TKPEVSEGTE |
|---|---|---|---|---|---|
| Gorilla #2   | .......... | .......... | .......... | .......... | .......... |
| Orang        | .......... | .......... | ......V... | .L........ | .......... |
| Human J03132 | VTAEDEGTQR | LTCAVILGNQ | SQETLQTVTI | YSFPAPNVIL | TKPEVSEGTE |
| Human X06990 | .......... | .......... | .......... | .......... | .......... |
| Human X59286-8 | ?????????? | ?????????? | ?????????? | ?????????? | ?????????? |
| Human #4     | .......... | .......... | .......... | .......... | .......... |
| Human #7     | .......... | .......... | .......... | .......... | .......... |
| Human #8     | .......... | .......... | .......... | .......... | .......... |
| Human M24283 | .......... | .......... | .R........ | .......... | .......... |
| Human U86814 | .......... | .......... | .R........ | .......... | .......... |
| Chimp M86848 | .......W.. | ......T... | .......... | .......... | .......... |
| Chimp #1     | .......W.. | ......T... | .......... | .......... | .......... |
| Gorilla #1   | ..E....W.. | ......R... | ....R..... | .......T.. | .......M.. |

|              | VTVKCEAHPR | AKVTLNGVPA | QPLGPRAQLL | LKATPEDNGR | SFSCSATLEV |
|---|---|---|---|---|---|
| Human J03132 | VTVKCEAHPR | AKVTLNGVPA | QPLGPRAQLL | LKATPEDNGR | SFSCSATLEV |
| Human X06990 | .......... | .......... | .......... | .......... | .......... |
| Human X59286-8 | ?????????? | ?????????? | ?????????? | ?????????? | ?????????? |
| Human #4     | .......... | .......... | ...V...V.. | .......... | .......... |
| Human #7     | .......... | .......... | ...V...V.. | .......... | .......... |
| Human #8     | .......... | .......... | ..P..T.F.. | .......... | .......... |
| Human M24283 | .......... | .......... | ..P..T.F.. | .......... | .......... |
| Human U86814 | .......... | .......... | ..P....F.. | .......... | .......... |
| Chimp M86848 | .......... | .......... | .......... | .......... | .......... |
| Chimp #1     | ?????????? | ?????????? | ?????????? | ?????????? | ?????????? |
| Gorilla #1   | .......... | .......... | .......... | .......... | .......... |
| Gorilla #2   | .......... | .......... | .......... | .......... | .......... |
| Orang        | ......I... | ....A..N.. | .......... | .......... | .......... |

|              | AGQLIHKNQT | RELRVLYGPR | LDERDCPGNW | TWPENSQQTP | MCQAWGNPLP |
|---|---|---|---|---|---|
| Human J03132 | AGQLIHKNQT | RELRVLYGPR | LDERDCPGNW | TWPENSQQTP | MCQAWGNPLP |
| Human X06990 | .......... | .......... | .......... | .......... | .......... |

Fig. 5C

|  | | | | | |
|---|---|---|---|---|---|
| Human X59286-8 | .......... | .......... | .......... | .......... | .......... |
| Human #4 | .......... | .......... | .......... | .......... | .......... |
| Human #7 | .......... | .......... | .......... | .......... | .......... |
| Human #8 | .......... | .......... | .......... | .......... | .......... |
| Human M24283 | .......... | .......... | .......... | .......... | .......... |
| Human U86814 | ?????????? | ?????????? | ?????????? | ?????????? | ?????????? |
| Chimp M86848 | .......... | .......... | .......... | .......... | ....S..... |
| Chimp #1 | .......... | .......... | .......... | .......... | ....S..... |
| Gorilla #1 | .......... | .......... | .......... | .......... | .......... |
| Gorilla #2 | .......... | .......... | .......... | .......... | .......... |
| Orang | .......... | .......... | .......... | .......... | .......... |
| Human J03132 | ELKCLKDGTF | PLPIGESVTV | TRDLEGTYLC | RARSTQGEVT | REVTVNVLSP |
| Human X06990 | .......... | .......... | .......... | .......... | .......... |
| Human X59286-8 | ?????????? | ?????????? | ?????????? | ?????????? | .......... |
| Human #4 | .......... | ....V..... | .......... | .......... | .......... |
| Human #7 | .......... | ....V..... | .......... | .......... | .......... |
| Human #8 | .......... | ....V..... | .......... | .......... | ....K..... |
| Human M24283 | .......... | ....V..... | .......... | .......... | .......... |
| Human U86814 | ?????????? | ?????????? | ?????????? | ?????????? | ?????????? |
| Chimp M86848 | .......... | .......... | .......... | .......... | ....K..... |
| Chimp #1 | .......... | .......... | .......... | .......... | ....K..... |
| Gorilla #1 | .......... | .......... | .......... | .......... | .......... |
| Gorilla #2 | .......... | .......... | .......... | .......... | .......... |
| Orang | .......... | .......... | .......... | .......... | .......... |
| Human J03132 | RYEIVIITVV | AAAVIMGTAG | LSTYLYNRQR | KIKKYRLQQA | QKGTPMKPNT |
| Human X06990 | .......... | .......... | .......... | .......... | .......... |
| Human X59286-8 | .......... | .......... | .......... | .......... | .......... |
| Human #4 | .......... | .......... | .......... | .......... | .......... |
| Human #7 | .......... | .......... | .......... | .......... | .......... |
| Human #8 | .......... | .......... | .......... | .......... | .......... |
| Human M24283 | .......... | .......... | .......... | .......... | .......... |
| Human U86814 | ?????????? | ?????????? | ?????????? | ?????????? | ?????????? |
| Chimp M86848 | .......... | .......... | .......... | ....R..... | .......... |
| Chimp #1 | .......... | .......... | .......... | ....R..... | .......... |

Fig. 5D

```
Gorilla #1       ...F...A..  ..........  ..........  ..R.......  ..........
Gorilla #2       ...F...A..  ..........  ..........  ..R.......  ..........
Orang            ..........  ...A.L....  ..........  ..RI......  ..........

Human J03132     QATPP
Human X06990     .....
Human X59286-8   .....
Human #4         .....
Human #7         ?????
Human #8         .....
Human M24283     .....
Human U86814     .....
Chimp M86848     .....
Chimp #1         .....
Gorilla #1       .....
Gorilla #2       .....
Orang            .T...
```

Fig. 5E

| | | | | | |
|---|---|---|---|---|---|
| Human M32331 | SDEKVFEVHV | RPKKLAVEPK | GSLEVNCSTT | CNQPEVGGLE | TSLDKILLDE |
| Human #4     | .......... | .......... | .......... | .......... | .......... |
| Human #8     | .......... | .......... | .......... | .......... | .......... |
| Human X15606 | .......... | .......... | .......... | .......... | ...N...... |
| Chimp #1     | .......... | .......... | ...K...... | .......... | .......... |
| Chimp #2     | .......... | .......... | ...K...... | .......... | .......... |
| Gorilla #2   | .......... | .......... | A......... | .......... | .......... |

| | | | | | |
|---|---|---|---|---|---|
| Human M32331 | QAQWKHYLVS | NISHDTVLQC | HFTCSGKQES | MNSNVSVYQP | PRQVILTLQP |
| Human #4     | .......... | .......... | .......... | .......... | .......... |
| Human #8     | .......... | .......... | .......... | .......... | .......... |
| Human X15606 | .......... | .......... | .......... | .......... | .......... |
| Chimp #1     | .......... | .......... | .......... | .......... | .......... |
| Chimp #2     | .......... | .......... | .......... | .......... | .......... |
| Gorilla #2   | .......... | .......... | .......... | .......... | .......... |

| | | | | | |
|---|---|---|---|---|---|
| Human M32331 | TLVAVGKSFT | IECRVPTVEP | LDSLTLFLFR | GNETLHYETF | GKAAPAPQEA |
| Human #4     | .......... | .......... | .......... | .......... | .......... |
| Human #8     | .......... | .......... | .......... | .......... | .......... |
| Human X15606 | .......... | .......... | .......... | .......... | .......... |
| Chimp #1     | .......... | .......... | .......... | .......... | .......... |
| Chimp #2     | .......... | .......... | .......... | .......... | .......... |
| Gorilla #2   | .......... | .......... | .......... | ......NQ.. | ......L... |

| | | | | | |
|---|---|---|---|---|---|
| Human M32331 | TATFNSTADR | EDGHRNFSCL | AVLDLMSRGG | NIFHKHSAPK | MLEIYEPVSD |
| Human #4     | .......... | .......... | .......... | .......... | .......... |
| Human #8     | .......... | .......... | .......... | .......... | .......... |
| Human X15606 | .......... | .......... | .......... | .......... | .......... |
| Chimp #1     | .V........ | D......... | .......... | .......... | .......... |
| Chimp #2     | .V........ | D......... | .......... | .......... | .......... |
| Gorilla #2   | .......... | .......... | .....I.... | ...QE..... | .......... |

(SEQ ID NO:7)

Fig. 6A

```
Human M32331      SQMVIIVTVV  SVLLSLFVTS  VLLCFIFGQH  LRQQRMGTYG  VRAAWRRLPQ
Human #4          ..........  ..........  ..........  ..........  ..........
Human #8          ..........  ..........  ..........  ..........  ..........
Human X15606      ..........  ..........  ..........  ..........  ..........
Chimp #1          ..........  ..........  ..........  ..........  ..........
Chimp #2          ..........  ..........  ..........  ..........  ..........
Gorilla #2        ..........  ..........  ..........  ..........  ..........

Human M32331      AFRP
Human #4          ....
Human #8          ....
Human X15606      ....
Chimp #1          ....
Chimp #2          ....
Gorilla #2        ....
```

Fig. 6B

| | | | | | |
|---|---|---|---|---|---|
| Human X69819 | QEFLLRVEPQ | NPVLSAGGSL | FVNCSTDCPS | SEKIALETSL | SKELVASGMG |
| Human #4 | .......... | .......... | .......... | .......... | .......... |
| Human #5 | .......... | .......... | .......... | .......... | .......... |
| Human #7 | .......... | .......... | .......... | .......... | .......... |
| Human S50015 | .......... | .......... | .......... | F......... | .......... |
| Chimp #3 | .......... | .......... | .......... | .......... | .......... |
| Chimp #4 | .......... | .......... | .......... | .......... | .......... |
| Chimp #5 | .......... | .......... | .......... | .......... | .......... |
| Gorilla #1 | .......... | .......... | .......... | .......... | .......... |
| Gorilla #2 | .......... | .......... | .......... | .......... | .......... |
| Orang | .......... | ....P..... | L......... | .K........ | .....DN... |
| | | | | | |
| Human X69819 | WAAFNLSNVT | GNSRILCSVY | CNGSQITGSS | NITVYGLPER | VELAPLPPWQ |
| Human #4 | .......... | .......... | .......... | .......... | .......... |
| Human #5 | .......... | .......... | .......... | .......... | .......... |
| Human #7 | .......... | .......... | .......... | .......... | .......... |
| Human S50015 | .......... | .......... | .......... | .......... | .......... |
| Chimp #3 | .......... | .......... | .......... | .....R.... | .......... |
| Chimp #4 | .......... | .......... | .......... | .....R.... | .......... |
| Chimp #5 | .......... | .......... | .......... | .....R.... | .......... |
| Gorilla #1 | .......... | .......... | .......... | .....R.... | .......... |
| Gorilla #2 | .......... | .......... | .......... | .....R.... | .......... |
| Orang | ....Y..... | .......... | ......I... | .....R.... | .......L.. |
| | | | | | |
| Human X69819 | PVGQNFTLRC | QVEGGSPRTS | LTVVLLRWEE | ELSRQPAVEE | PAEVTATVLA |
| Human #4 | .......... | .......... | .......... | .......... | .......... |
| Human #5 | .......... | .......... | .......... | .......... | .......... |
| Human #7 | .......... | .......... | .......... | .......... | .......... |
| Human S50015 | .......... | .......... | .......... | .......... | .......... |
| Chimp #3 | Q......... | .......... | .......... | .......... | .......... |
| Chimp #4 | Q......... | .......... | .......... | .......... | .......... |
| Chimp #5 | R......... | .......... | .......... | .......... | .......... |
| Gorilla #1 | .......... | .......... | .......... | .......... | .......P.. |
| Gorilla #2 | .......... | .......... | .......... | .......... | .......P.. |

(SEQ ID NO:8)

Fig. 7A

| | | | | | |
|---|---|---|---|---|---|
| Human X69819 | SRDDHGAPFS | CRTELDMQPQ | GLGLFVNTSA | PRQLRTFVLP | VTPPRLVAPR |
| Human #4     | .......... | .......... | .......... | .......... | .......... |
| Human #5     | .......... | .......... | .......... | .......... | .......... |
| Human #7     | .......... | .......... | .......... | .......... | .......... |
| Human S50015 | .......... | .......... | .......... | .......... | .......... |
| Chimp #3     | .......... | .......... | .......... | .......... | .......... |
| Chimp #4     | .......... | .......... | .......... | .......... | .......... |
| Chimp #5     | .......... | .......... | .......... | .......... | .......... |
| Gorilla #1   | ..G....... | .......... | .......... | .......... | M......... |
| Gorilla #2   | ..G....... | .......... | .......... | .......... | M...S..... |
| Orang        | ..GH...H.. | .......... | .......... | .......... | .......... |

| | | | | | |
|---|---|---|---|---|---|
| Human X69819 | FLEVETSWPV | DCTLDGLFPA | SEAQVYLALG | DQMLNATVMN | HGDTLTATAT |
| Human #4     | .......... | .......... | .......... | .......... | .......... |
| Human #5     | .......... | .......... | .......... | .......... | .......... |
| Human #7     | .......... | .......... | .......... | .......... | .......... |
| Human S50015 | .......... | .......... | .......... | .......... | .......... |
| Chimp #3     | .......... | .......... | .......... | .......... | .......... |
| Chimp #4     | .......... | .......... | .......... | .......... | .......... |
| Chimp #5     | .......... | .......... | .......... | .......... | .......... |
| Gorilla #1   | .......... | .......... | .......... | .......... | .......... |
| Gorilla #2   | .......... | .......... | .......... | .......... | .......... |
| Orang        | ...A...... | .......... | .......... | ........V. | .......... |

| | | | | | |
|---|---|---|---|---|---|
| Human X69819 | ATARADQEGA | REIVCNVTLG | GERREARENL | TVFSFLGPIV | NLSEPTAHEG |
| Human #4     | .......... | .......... | .......... | .......... | .......... |
| Human #5     | .......... | .......... | .......... | .......... | .......... |
| Human #7     | .......... | .......... | .......... | .......... | .......... |
| Human S50015 | .......... | .......... | .......... | .......... | .......... |
| Chimp #3     | .......... | .......... | .......... | ........T. | ........P.. |

Fig. 7B

```
Chimp #4        ..........  ..........  ..........  .......T..  .......P..
Chimp #5        ..........  ..........  ..........  .......T..  .......P..
Gorilla #1      ...L......  ..........  ..........  .I........  .......P..
Gorilla #2      ...L......  ..........  ..........  .I........  .......P..
Orang           .M........  Q.........  ..........  .........L  .....S.P..

Human X69819    STVTVSCMAG  ARVQVTLDGV  PAAAPGQPAQ  LQLNATESDD  GRSFFCSATL
Human #4        ..........  ..........  ..........  ..........  ..........
Human #5        ..........  ..........  ..........  ..........  ..........
Human #7        ..........  ..........  ..........  ..........  ..........
Human S50015    ..........  ..........  ..........  ..........  ..........
Chimp #3        ..........  ..........  ..........  ..........  R.........
Chimp #4        ..........  ..........  ..........  ..........  R.........
Chimp #5        ..........  ..........  ..........  ..........  R.........
Gorilla #1      ..........  ..........  ..........  ..........  ..........
Gorilla #2      ..........  ..........  ..........  ..........  ..........
Orang           ..........  ..........  ..........  ..........  ..........

Human X69819    EVDGEFLHRN  SSVQLRVLYG  PKIDRATCPQ  HLKWKDKTRH  VLQCQARGNP
Human #4        ..........  ..........  ..........  ..........  ..........
Human #5        ..........  ..........  ..........  ..........  ..........
Human #7        ..........  ..........  ..........  ..........  ..........
Human S50015    ..........  ..........  ..........  ..........  ..........
Chimp #3        ..........  ..........  ..........  ........T.  ..........
Chimp #4        ..........  ..........  ..........  ........T.  ..........
Chimp #5        ..........  ..........  ..........  ........T.  ..........
Gorilla #1      ..........  ..........  ..........  ........T.  ..........
Gorilla #2      ..........  ..........  ..........  ........T.  ..........
Orang           ......F...  ..........  ..........  ..........  ..........

Human X69819    YPELRCLKEG  SSREVPVGIP  FFVNVTHNGT  YQCQASSSRG  KYTLVVVMDI
Human #4        ..........  ..........  ..........  ..........  ..........
Human #5        ..........  ..........  ..........  ..........  ..........
Human #7        ..........  ..........  ..........  ..........  ..........
```

Fig. 7C

| | | | | | |
|---|---|---|---|---|---|
| Human S50015 | .......... | .......... | .......... | .......... | .......... |
| Chimp #3 | .......... | .......... | .......... | .......... | .......... |
| Chimp #4 | .......... | .......... | .......... | .......... | .......... |
| Chimp #5 | .......... | .......... | .......... | .......... | .......... |
| Gorilla #1 | .......... | .......... | .......... | .......... | .......... |
| Gorilla #2 | .......... | .......... | .......... | .......... | .......... |
| Orang | H......... | .......... | .......... | .......... | R......... |
| | | | | | |
| Human X69819 | EAGSSHFVPV | FVAVLLTLGV | VTIVLALMYV | FREHQRSGSY | HVREESTYLP |
| Human #4 | .......... | .......... | .......... | .......... | .......... |
| Human #5 | .......... | .......... | .......... | .......... | .....T.... |
| Human #7 | .......... | .......... | .......... | .......... | .......... |
| Human S50015 | .......... | .......... | .......... | .......... | .......... |
| Chimp #3 | .......... | .......... | .......... | ....K..... | .......... |
| Chimp #4 | .......... | .......... | .......... | ....K..... | .......... |
| Chimp #5 | .......... | .......... | .......... | ....K..... | .......... |
| Gorilla #1 | .......... | .......... | .......... | ....K..... | .......... |
| Gorilla #2 | .......... | .......... | .......... | ....K..... | .......... |
| Orang | ...N....L. | .L...V.... | ..V.V..... | ....K...R. | ...Q...S.. |
| | | | | | |
| Human X69819 | LTSMQPTEAM | GEEPSRAE | | | |
| Human #4 | .......... | ........ | | | |
| Human #5 | .......... | ........ | | | |
| Human #7 | .......... | ........ | | | |
| Human S50015 | .......... | ........ | | | |
| Chimp #3 | .......Q.. | ........ | | | |
| Chimp #4 | .......Q.. | ........ | | | |
| Chimp #5 | .......... | ........ | | | |
| Gorilla #1 | .......... | ........ | | | |
| Gorilla #2 | .......... | ........ | | | |
| Orang | .......... | .....T.. | | | |

Fig. 7D

Human

ATGAGTGACTCCAAGGAACCAAGACTGCAGCAGCTGGCCTCCTGGAGGAGAACA
GCTGAGAGGCCTTGGATTCCGACAGACTGAGGATACAAGAGCTTAGCAGGTGTC
TTGGCCATGGTCCCTGGTGCTGCAACTCCTCCTCAGCGCTCTTGGCTGGCTCCT
TGTCCAAGTGTCCAAGGTCCCCAGCTCAGTCAGGAACAATCCAGGCAAGACG
CGATCTACCAGAACCTGACCCAGCTTAAAGCTGCAGTGGGTGAGCTCTCAGAAA
TCCAAGCTGCAGGAGATCTACCAGGAGCTGACCCAGTGAAGGCTGCAGTGGGTGA
GCTTCCAGAGAAATCTAAGCTGCAGGAGATCTACCAGGAGCTGACCCGGCTGAAGG
CTGCAGTGGGTGAGCTTCCAGAGAAATCTAAGCTGCAGGAGATCTACCAGGAGAT
CTACCAGGAGCTGACTCGGCTGAAGGCTGAGCTTCCAGAGTGGGTGAGCTTGAGCTT
AGCAGCAGGAGATCTACCAGGAGCAGGAGATCTAAGCAGGAGCTGACCCGGCTGAAGGCTGC
CCAGAGAAATCTAAGCAGGAGATCTACCAGGAGCTGACCCGGCTGAAGGCTGACC
AGTGGGTGAGCTTCCAGAGAAATCTAAGCAGCAGGAGATCTACCAGGAGCTGACC
CAGCTGAAGGCTGCAGTGAACGCCTGCCACCCTGTCCCTGGAATGGACATT
CTTCCAAGGAAACTGTTACTTCATGTCTAACTCCCAGCGACACTGGCACGACTCCAT
CACCGCCTGCAAAGAAAGTGGGGGCCCAGTCTCGTCGTAATCAAAAGTGCTGAGGAGC
AGAACTTCCTACAGCTGCAGTCTTCCAGAAGTAACCGCTTCACCTGGATGGGACTTT
CAGATCTAAATCAGGAAGGCACGTGGCAATGGGTGGACGGCTCACCTCTGTTGCCC
AGCTTCAAGCAGTATTGGAACAGAGGAGCCAACAACGTTGGGGAGGAAGACTG
CGCGGAATTTAGTGGCAATGGCTGGAACGACGACAAATGTAATCTTGCCAATTCTG
GATCTGCAAAAGTCCGCAGCTCCTGTCTCCAGGATGAAGAACAGTTCTTCTCC
AGCCCCTGCCACCCCAAACCCCTCCTGCG (SEQ. ID. NO. 9)

Fig. 11

Chimpanzee

ATGAGTGACTCCAAGGAACCAAGAGACTGCAGCAGCTGGGCCTCCTGGAGGAGGAACA
GCTGAGAGGCCTTGGATTCCGACAGACTGGAGGCTACAAGAGCTTAGCAGGTGTC
TTGGCCATGGTCCCCTGGTGCTGCAACTCTCCTTCACGCTCTTGCTGCTGGCTCCT
TGTCCAAGTGTCAAGGTCCCCAGTCCAGGAAGAATCCAGGCAAGACG
TGATCTACCAGAACCTGACCCAGCTTAAAGCTGCAGTGGGTGAGCTCTCAGAGAAA
TCCAAGCTGCAGGAGATCTACCAGGAGCTGAACCCAGCTGAAGGCTGCAGTGGGTGA
GCTTCCAGAGAAATCTAAGCAGCAGGAGATCTACCAGGAGATCTACCAGGAGCTG
ACTCGGCTGAAGGCTGCAGTGGGTGAGCTTCCAGAGATGCAGGAGCTTCCAGAGAT
CTACCAGGAGCTGACTCGGCTGAAGGCTGCAGTGGGTGAGCTTCCAGAGAAATCTA
AGCAGCAGGAGATCTACCAGGAGCTGACCCAGCTGAAGGCTGCAGTGGGTGAGCTT
CCAGAGAAATCTAAGCAGCAGGAGATCTACCAGGAGCTGACCCAGCTGAAGGCTGC
AGTGGGTGAGCTTCCAGAGAACCGCCTGTGCCCCCTGGAACTGCACGACTCCAT
CGGGCTGAAGGCTGCAGAAGTGGGGCCCAGCTGTCGTAATCAAAGTGCTGAGGAGC
CTTCCAAGGAAACTGTTACTTCATGTCTAACTGCTGGAACTGCACGACTCCAT
CACTGCCTGCAAAGAAGTGGGGCCCAGCTGTCGTAATCAAAGTGCTGAGGAGC
AGAACTTCCTACAGCTGCAGTCTTCCAGAAGTAACCGCTTCACCTGGATGGACTTT
CAGATCTAAATGAGGAAGGCATGTGGCAATGTGGACGGCTCACCTCTGTTGCCC
AGCTTCAACCAGTAYTGGAACAGAGGAGCCCAACAAGTTGGGGAGGAAGACTG
CGCGGAATTTAGTGGCAATGGCTGGAATGACGACAAATGTAATCTTGCCAAATTCTG
GATCTGCAAAAGTCCGCAGCCTCTCTGCTCCAGGAGATGAAGAACAGTTTCTTCTCC
AGCCCCTGCCACCCCAAACCCCTCCTGCG (SEQ. ID. NO. 10)

Fig. 12

Gorilla

ATGAGTGACTCCAAGGAACCAAGACTGCAGCAGCTGGGCCTCCTGGAGGAGGAACA
GCTGAGAGGCCTTGGATTCCGACAGACTCGAGGCTACAGAGCTTAGCAGGTGTC
TTGGCCATGGTCCCCTGGTGCTGCAACTCCTCTCCTTCACGCTCTTGGCTGCTCCT
TGTCCAAGTGTCCAAGGTCCCCAGCTCCAGTTCAGGAACAATCCAGGCAAGACG
CGATCTACCAGAACCTGACCCAGTTTAAAGCTGCAGTGGGTGAGCTCTCAGAGAAA
TCCAAGCTGCAGGAGATCTATCAGGAGCTGACCCAGTGAAGGCTGCAGTGGGTGA
GCTTCCAGAGAAATCTAAGCAGCAGGAGATCTACCAGGAGCTGAGCCAGTGAAGG
CTGCAGTGGGTGAGCTTCCAGAGAAATCTAAGCAGCAGGAGATCTACCAGGAGCTG
ACCCGGCTGAAGGCTGCAGTGGGTGAGCTGAAGGCTGAAGGCTGAGCTTGAGCTT
CTACCAGGAGCAGGAGATCTACCAGGAGCTTCCAGAGAAATCTAAGCAGCAGGAT
AGCAGCAGGAGATCTAAGCAGCAGGAGATCTACCAGGAGCTGAAGGCTGAAGGCTGC
CCAGAGAAATCTAAGCAGCAGGAGATCTACCAGGAGCTGAGCCAGTGAAGGCTGC
AGTGGGTGAGCTTCCAGAGAAATCTAAGCAGCAGGAGATCTACCAGGAGCTGACC
CAGTGAAGGCTGCAGTGGAACGCTGTGCCGCCGCTGCCCCTGGGAATGGACATT
CTTCCAAGGAAACTGTTACTTCATGTCTAACTCCCAGGCACGACTGGCACGACTCCAT
CACCGCCTGCCAAGAAGTGCTGCAGCCCCAGCTCGTAATCAAAAGTGCTGAGGAGC
AGAACTTCCTACAGCTCTTCCAGAGTCTTCCAGAAGTAACCGCTTCACCTGGATGGACTTT
CAGATCTAAATCATGAAGGCACGTGGCAATGGGTGACGCTCACCTCTGTTGCCC
AGCTTCGAGCAGCAGTATTGGAACAGAGAGCCAACAACGTTGGGGAGGAAGACTG
CGGGAATTTAGTGGCAATGGCTGGAACGATGACAAATGTAATCTTGCCAAATTCTG
GATCTGCAAAAAGTCTGCAGCTCGCCTCCTGCTCCAGGGATGAAGAACAGTTTCTTCTCC
AGCCCTCTGCCACCCCAAACCCCCACCCTCCTGCG (SEQ. ID. NO. 11)

Fig. 13

```
1     ctccagacct acccagaaag atgcccggat ggatcctgca gctccgtggc ttttctggga
61    agcagcggcc cctgctctca agagaccctg gctcctgatg gtggcccaa  ggttgccagc
121   tggtgctagg gactcaggac agtttcccag aaaaggccaa gcgggcagcc cctccagggg
181   ccgggtgagg aagctggggg gtgcggaggc cacactgggt ccctgaaccc cctgcttggt
241   tacagtgcag ctcctcaagt ccacagacgt gggccggcac agcctcctgt acctgaagga
301   aatcggccgt ggctggttcg ggaaggtgtt cctggggag  gtgaactctg gcatcagcag
361   tgcccaggtg gtggtgaagg agctgcaggc tagtgccagc gtgcaggagc ag<u>atg</u>cagtt
421   cctggaggag gtgcagccct acagggccct gaagcacagc aacctgctcc agtgcctggc
481   ccagtgcgcc gaggtgacgc cctacctgct ggtgatggag ttctgcccac tggggaccct
541   caagggctac ctgcggagct gccgggtggc ggagtccatg gctcccgacc ccggacccct
601   gcagcgcatg gcctgtgagg tggcctgtgg cgtcctgcac cttcatcgca caatttcgt
661   gcacagcgac ctggccctgc ggaactgcct gctcacggct gacctgacgg tgaagattgg
721   tgactatggc ctggctcact gcaagtacag agaggactac ttcgtgactg ccgaccagct
781   gtgggtgcct ctgcgctgga tcgcgccaga gctggtggac gaggtgcata gcaacctgct
841   cgtcgtggac cagaccaaga gcgggaatgt gtggtccctg ggcgtgacca tctgggagct
901   ctttgagctg gcacgcagc  cctatcccca gcactcggac cagcaggtgc tggcgtacac
961   ggtccgggag cagcagctca agctgcccaa gccccagctg cagctgaccc tgtcggaccg
1021  ctggtacgag gtgatgcagt tctgctggct gcagcccgag cagcggccca gccgagga
1081  ggtgcacctg ctgctgtcct acctgtgtgc caagggcgcc accgaagcag aggaggagtt
1141  tgaacggcgc tggcgctctc tgcggcccgg cggggcggc  gtggggcccg ggcccggtgc
1201  ggcggggccc atgctgggcg gcgtggtgga gctcgccgct gcctcgtcct tcccgctgct
1261  ggagcagttc gcggcgacg  gcttccacgc ggacggcgac gacgtgctga cggtgaccga
1321  gaccagccga ggcctcaatt ttgagtacaa gtgggaggcg ggccgcggcg cggaggcctt
1381  cccggccacg ctgagccctg ccgcaccgc  acgcctgcag gagctgtgcg ccccgacgg
1441  cgcgccccg  ggcgtggttc cggtgctcag cgcgcacagc ccgtcgctgg cagcgagta
1501  cttcatccgc ctagaggagg ccgcacccgc cgccggccac gaccctgact gcgccggctg
1561  cgcccccagt ccacctgcca ccgcggacca ggacgacgac tctgacggca gcaccgccgc
1621  ctcgctggcc atggagccgc tgctgggcca cgggccaccc gtcgacgtcc cctggggccg
1681  cggcgaccac taccctcgca gaagcttggc gcgggacccg ctctgcccct cacgctctcc
1741  ctcgccctcg gcggggcccc tgagtctggc ggagggagga gcggaggatg cagactgggg
1801  cgtggccgcc ttctgtcctg ccttcttcga ggacccactg ggcacgtccc ctttggggag
1861  ctcaggggcg ccccgctgc  cgctgactgg cgaggatgag ctagaggagg tgggagcgcg
1921  gagggccgcc cagcgcgggc actggcgctc caacgtgtca gccaacaaca acagcggcag
1981  ccgctgtcca gagtcctggg accccgtctc tgcgggctgc cacgctgagg ctgccccag
2041  tccaaagcag accccacggg cctccccga  gccggggtac cctggagagc ctctgcttgg
2101  gctccaggca gcctctgccc aggagccagg ctgctgcccc ggcctccctc atctatgctc
2161  tgcccagggc ctggcacctg ctccctgcct ggttacaccc tcctggacag agacagccag
2221  tagtgggggt gaccaccgc  aggcagagcc caagcttgcc acggaggctg agggcactac
2281  cggaccccgc ctgcccttc  cttccgtccc ctccccatcc caggagggag ccccacttcc
2341  ctcggaggag gccagtgccc ccgacgcccc tgatgccctg cctgactctc ccacgcctgc
2401  tactggtggc gaggtgtctg ccatcaagct ggcttctgcc ctgaatggca gcagcagctc
2461  tcccgaggtg gaggcaccca gcagtgagga tgaggacacg gctgaggcca cctcaggcat
2521  cttcaccgac acgtccagcg acggcctgca ggccaggagg ccggatgtgg tgccagcctt
2581  ccgctctctg cagaagcagg tgggaccccc cgactccctg gactccctgg acatcccgtc
2641  ctcagccagt gatggtggct atgaggtctt cagcccgtcg gccactggcc cctctggagg
2701  gcagccgcga gcgctggaca gtggctatga caccgagaac tatgagtccc ctgagtttgt
2761  gctcaaggag gcgcaggaag ggtgtgagcc ccaggccttt gcggagctgg cctcagaggg
2821  tgagggcccc gggcccgaga cacggctctc cacctccctc agtggcctca acgagaagaa
2881  tccctaccga gactctgcct acttctcaga cctcgaggct gaggccgagg ccacctcagg
2941  cccagagaag aagtgcggcg gggaccgagc ccccgggcca gagctgggcc tgccgagcac
3001  tgggcagccg tctgagcagg tctgtctcag gcctgggggtt tccggggagg cacaaggctc
```

Figure 14A

```
3061 tggccccggg gaggtgctgc ccccactgct gcagcttgaa gggtcctccc cagagcccag
3121 cacctgcccc tcgggcctgg tcccagagcc tccggagccc caaggcccag ccaaggtgcg
3181 gcctgggccc agccccagct gctcccagtt tttcctgctg accccggttc cgctgagatc
3241 agaaggcaac agctctgagt tccaggggcc cccaggactg ttgtcagggc cggccccaca
3301 aaagcggatg ggggcccag gcaccccag agcccactc cgcctggctc tgcccggcct
3361 ccctgcggcc ttggagggcc ggccggagga ggaggaggag gacagtgagg acagcgacga
3421 gtctgacgag gagctccgct gctacagcgt ccaggagcct agcgaggaca gcgaagagga
3481 ggcgccggcg gtgcccgtgg tggtggctga gagccagagc gcgcgcaacc tgcgcagcct
3541 gctcaagatg cccagcctgc tgtccgagac cttctgcgag gacctggaac gcaagaagaa
3601 ggccgtgtcc ttcttcgacg acgtcaccgt ctacctcttt gaccaggaaa gccccacccg
3661 ggagctcggg gagcccttcc cgggcgccaa ggaatcgccc cctacgttcc ttaggggggag
3721 ccccggctct cccagcgccc ccaaccggcc gcagcaggct gatggctccc caaatggctc
3781 cacagcggaa gagggtggtg ggttcgcgtg ggacgacgac ttcccgctga tgacggccaa
3841 ggcagccttc gccatggccc tagacccggc cgcacccgcc cggctgcgc ccacgcccac
3901 gcccgctccc ttctcgcgct tcacggtgtc gcccgcgccc acgtcccgct tctccatcac
3961 gcacgtgtct gactcggacg ccgagtccaa gagaggacct gaagctggtg ccggggggtga
4021 gagtaaagag gct tgagacc tgggcagctc ctgcccctca aggctggcgt caccggagcc
4081 cctgccaggc agcagcgagg atggtgaccg agaaggtggg gaccacgtcc tggtggctgt
4141 tggcagcaga ttcaggtgcc tctgccccac gcggtgtcct ggagaagccc gtgggatgag
4201 aggccctgga tggtagatcg gccatgctcc gccccagagg cagaattcgt ctgggctttt
4261 aggcttgctg ctagcccctg ggggcgcctg gagccacagt gggtgtctgt acacacatac
4321 acactcaaaa ggggccagtg cccctgggca cggcggcccc caccctctgc cctgcctgcc
4381 tggcctcgga ggacccgcat gccccatccg gcagctcctc cggtgtgctc acaggacact
4441 taaaccagga cgaggcatgg ccccgagaca ctggcaggtt tgtgagcctc ttcccacccc
4501 ctgtgccccc acccttgcct ggttcctggt ggctcagggc aaggagtggc cctgggcgcc
4561 cgtgtcggtc ctgtttccgc tgcccttatc tcaaagtccg tggctgtttc cccttcactg
4621 actcagctag accgtaagc ccaccttcc cacagggaac aggctgctcc cacctgggtc
4681 ccgctgtggc cacggtgggc agcccaaaag atcaggggtg gaggggcttc caggctgtac
4741 tcctgccccg tgggccccgt tctagaggtg cccttggcag gaccgtgcag gcagctcccc
4801 tctgtggggc agtatctggt cctgtgcccc agctgccaaa ggagagtggg ggccatgccc
4861 cgcagtcagt gttgggggc tcctgcctac agggagaggg atggtgggga aggggtggag
4921 ctgggggcag ggcagcacag gaatatttt tgtaactaac taactgctgt ggttggagcg
4981 aatggaagtt gggtgatttt aagttattgt tgccaaagag atgtaaagtt tattgttgct
5041 tcgcagggg atttgttttg tgttttgttt gaggcttaga acgctggtgc aatgttttct
5101 tgttccttgt tttttaagag aaatgaagct aagaaaaaag (SEQ ID NO: 14 and 15)
```

Figure 14A (continued)

MQFLEEVQPYRALKHSNLLQCLAQCAEVTPYLLVMEFCPLGDLKGYLRSCRVAESMAP
DPRTLQRMACEVACGVLHLHRNNFVHSDLALRNCLLTADLTVKIGDYGLAHCKYRED
YFVTADQLWVPLRWIAPELVDEVHSNLLVVDQTKSGNVWSLGVTIWELFELGTQPYPQ
HSDQQVLAYTVREQQLKLPKPQLQLTLSDRWYEVMQFCWLQPEQRPTAEEVHLLLSYL
CAKGATEAEEEFERRWRSLRPGGGGVGPGPGAAGPMLGGVVELAAASSFPLLEQFAGD
GFHADGDDVLTVTETSRGLNFEYKWEAGRGAEAFPATLSPGRTARLQELCAPDGAPPG
VVPVLSAHSPSLGSEYFIRLEEAAPAAGHDPDCAGCAPSPPATADQDDDSDGSTAASLA
MEPLLGHGPPVDVPWGRGDHYPRRSLARDPLCPSRSPSPSAGPLSLAEGGAEDADWGV
AAFCPAFFEDPLGTSPLGSSGAPPLPLTGEDELEEVGARRAAQRGHWRSNVSANNNSGS
RCPESWDPVSAGCHAEGCPSPKQTPRASPEPGYPGEPLLGLQAASAQEPGCCPGLPHLCS
AQGLAPAPCLVTPSWTETASSGGDHPQAEPKLATEAEGTTGPRLPLPSVPSPSQEGAPLP
SEEASAPDAPDALPDSPTPATGGEVSAIKLASALNGSSSSPEVEAPSSEDEDTAEATSGIFT
DTSSDGLQARRPDVVPAFRSLQKQVGTPDSLDSLDIPSSASDGGYEVFSPSATGPSGGQP
RALDSGYDTENYESPEFVLKEAQEGCEPQAFAELASEGEGPGPETRLSTSLSGLNEKNPY
RDSAYFSDLEAEAEATSGPEKKCGGDRAPGPELGLPSTGQPSEQVCLRPGVSGEAQGSG
PGEVLPPLLQLEGSSPEPSTCPSGLVPEPPEPQGPAKVRPGPSPSCSQFFLLTPVPLRSEGN
SSEFQGPPGLLSGPAPQKRMGGPGTPRAPLRLALPGLPAALEGRPEEEEEDSEDSDESDE
ELRCYSVQEPSEDSEEEAPAVPVVVAESQSARNLRSLLKMPSLLSETFCEDLERKKKAVS
FFDDVTVYLFDQESPTRELGEPFPGAKESPPTFLRGSPGSPSAPNRPQQADGSPNGSTAEE
GGGFAWDDDFPLMTAKAAFAMALDPAAPAPAAPTPTPAPFSRFTVSPAPTSRFSITHVS
DSDAESKRGPEAGAGGESKEA (SEQ ID NO:16)

Figure 14B

```
GCTCCCTGCCTGGTTACACCCTCCTGGACAGAGACAGCCGGTAGTGGGGGTGACCACCCGCAGGCAGAGCC
CAAGCTTGCCACGGAGGCTGAGGGCACTGCCGGACCCTGTCTGCCCCTTCCTTCCGTCCCCTCCCCATCCC
AGGAGGGAGCCCCACTTCCCTCGGAGGAGGCCAGTGCCCCTGACGCCCCTGATGCCCTGCCTGACTCTCCC
ATGCCTGCTACTGGTGGCGAGGTGTCTGCCATCAAGCTGGCTTCTGTCCTGAATGGCAGCAGCAGCTCTCC
CGAGGTGGAGGCACCCAGCAGCGAGGATGAGGACACGGCTGAGGCCACCTCAGGCATCTTCACCGACACGT
CCAGCGACGGCCTGCAGGCCGAGAGGCTGGATGTGGTGCCAGCCTTCCGCTCTCTGCAGAAGCAGGTGGGG
ACCCCCGACTCCCTGGACTCCCTGGACATCCCATCCTCAGCCAGTGATGGTGGCTATGAGGTCTTCAGCCC
GTCGGCCACTGGCCCCTCTGGAGGGCAGCCCCGAGCGCTGGACAGTGGCTATGACACCGAGAACTATGAGT
CCCCTGAGTTTGTGCTCAAGGAGGCGCAGGAAGGGTGTGAGCCCCAGGCCTTTGAGGAGCTGGCCTCAGAG
GGTGAGGGCCCCGGCCCCGGGCCCGAGACGCGGCTCTCCACCTCCCTCAGTGGCCTCAACGAGAAGAATCC
CTACCGAGACTCTGCCTACTTCTCAGACCTGGAGGCTGAGGCCGAGGCCGAGGCCACCTCAGGCCCAGAGA
AGAAGTGCGGCGGGGACCAAGCCCCCGGGCCAGAGCTGGACCTGCCGAGCACTGGGCAGCCGTCTGAGCAG
GTCTCCCTCAGGCCTGGGGTTTCCGGGGAGGCACAAGGCTCTGGCCCCGGGGAGGTGCTGCCCCCACTGCT
GCGGCTTGAAGGATCCTCCCCAGAGCCCAGCACCTGCCCCTCGGGCCTGGTCCCAGAGCCTCCGGAGCCCC
AAGGCCCAGCCGAGGTGCGGCCTGGGCCCAGCCCCAGCTGCTCCCAGTTTTTCCTGCTGACCCCGGTTCCG
CTGAGATCAGAAGGCAACAGCTCTGAGTTCCAGGGGCCCCAGGACTGTTGTCAGGGCCGGCCCCACAAAA
GCGGATGGGGGGCCTAGGCACCCCCAGAGCCCCACTCCGCCTGGCTCTGCCCGGCCTCCCTGCGGCCTTGG
AGGGCCGGCCGGAGGAGGAGGAGGAGGACAGTGAGGACAGCGGCGAGTCTGACGAGGAGCTCCGCTGCTAC
AGCGTCCAGGAGCCTAGCGAGGACAGCGAAGAGGAGGCGCCGGCGGTGCCCGTGGTGGTGGCTGAGAGCCA
GAGCGCGCGCAACCTGCGCAGCCTGCTCAAGATGCCCAGCCTGCTGTCCGAGGCCTTCTGCGAGGACCTGG
AACGCAAGAAGAAGGCCGTGTCCTTCTTCGACGACGTCACCGTCTACCTCTTTGACCAGGAAAGCCCCACC
TGGGAGCTCGGGGAGCCCTTCCCGGGCGCCAAGGAATCGCCCCCCACGTTCCTTAGGGGGAGCCCCGGCTC
TCCCAGCGCCCCAACCGGCCGCAGCAGGCTGATGGCTCCCCAAATGGCTCCACAGCGGAAGAGGGTGGTG
GGTTCGCGTGGGACGACGACTTCCCGCTGATGCCGGCCAAGGCAGCCTTCGCCATGGCCCTAGACCCGGCC
GCACCCGCCCCGGCTGCGCCCACGCCC*****GCTCCCTTCTCGCGCTTCACGGTGTCGCCCGCGCCCAC
GTCCACGTCCGCTTCTCCATCACGCACGTGTCT       (SEQ ID NO:17)
```

Figure 15A

```
GCTCCCTGCCTGGTTACACCCTCCTGGACAGAGACAGACGGTAGTGGGGGTGACCACCCGCAGGCAGAGCC
CAAGCTTGCCACGGAGGCTGAGGGCACTGCCGGACCCCGCCTGCCCCTTCCTTCCGTCCCCTCCCCATCCC
AGGAGGGAGCCCCACTTCCCTCGGAGGAGGCCAGTGCCCCGACGCCCCTGATGCCCTGCCTGACTCGCCC
ACGCCTGCTACTGGTGGCGAGGTGTCTGCCACCAAGCTGGCTTCCGCCCTGAATGGCAGCAGCAGCTCTCC
CGAGGTGGAGGCACCCAGCAGTGAGGATGAGGACACGGCTGAGGCAACCTCAGGCATCTTCACCGACACGT
CCAGCGACGGCCTGCAGGCCGAGAGGCAGGATGTGGTGCCAGCCTTCCACTCTCTGCAGAAGCAGGTGGGG
ACCCCCGACTCCCTGGACTCCCTGGACATCCCGTCCTCAGCCAGTGATGGTGGCTATGAGGTCTTCAGCCC
GTCGGCCACGGGCCCCTCTGGAGGGCAGCCCCGAGCGCTGGACAGTGGCTATGACACCGAGAACTATGAGT
CCCCTGAGTTTGTGCTCAAGGAGGCGCAGGAAGGGTGTGAGCCCCAGGCCTTTGCGGAGCTGGCCTCAGAG
GGCGAGGGC*****CCCGGGCCCGAGACGCGGCTCTCCACCTCCCTCAGTGGCCTCAACGAGAAGAATCC
CTACCGAGATTCTGCCTACTTCTCAGACCTGGAGGCT*****GAGGCCGAGGCTACCTCAGGCCCAGAGA
AGAAGTGCGGTGGGGACCAAGCCCCCGGGCCAGAGCTGGGCCTGCCGAGCACTGGGCAGCCGTCTGAGCAG
GTCTCCCTCAGTCCTGGGGTTTCCGTGGAGGCACAAGGCTCTGGCCCCGGGGAGGTGCTGCCCCCACTGCT
GCGGCTTGAAGGGTCCTCCCCAGAGCCCAGCACCTGCCCCTCGGGCCTGGTCCCAGAGCCTCCGGAGCCCC
AAGGCCCAGCCGAGGTGCGGCCTGGGCCCAGCCCCAGCTGCTCCCAGTTTTTCCTGCTGACCCCGGTTCCG
CTGAGATCAGAAGGCAACAGCTCTGAGTTCCAGGGGCCCCAGGACTGTTGTCAGGGCCGGCCCCACAAAA
GCGGATGGGGGGCCCAGGCACCCCCAGAGCCCCACACCGCCTGGCTCTGCCCGGCCTCCCTGCGGCCTTGG
AGGGCCGGCCGGAGGAGGAGGAGGAGGACAGTGAGGACAGCGACGAGTCTGACGAGGAGCTCCGCTGCTAC
AGCGTCCAGGAGCCTAGCGAGGACAGCGAAGAGGAGGCGCCGGCGGTGCCCGTGGTGGTGGCTGAGAGCCA
GAGCGCGCGCAACCTGCGCAGCCTGCTCAAGATGCCCAGCCTGCTGTCCGAGGCCTTCTGCGAGGACCTGG
AACGCAAGAAGAAGGCCGTGTCCTTCTTCGACGACGTCACCGTCTACCTCTTTGACCAGGAAAGCCCCACC
CGGGAGCTCGGGGAGCCCTTCCCGGGCGCCAAGGAATCGCCCCCACGTTCCTTAGGGGGAGCCCCGGCTC
TTCCAGCGCCCCAACCGGCCGCAGCAGGCTGATGGCTCCCCAAATGGCTCCACAGCGGAAGAGGGTGGTG
GGTTCGCGTGGGACGACGACTTCCCGCTGATGCCGGCCAAGGCAGCCTTCGCCATGGCCCTAGACCCGGCC
GCACCCGCCCCGGCTGCGCCCACGCCC*****GCTCCCTTCTCGCGCTTCACGGTGTCGCCCGCGCCCAC
GTCC::::::CGCTTCTCCATCACGCACGTGTCT      (SEQ ID NO:18)
```

Figure 15B

```
Hs  ATG GCA GTG ACA ACT CGT TTG ACA TGG TTG CAC GAA AAG ATC CTG  45
Pt  ATG GCA GTG ACA ACT CGT TTG ACA TGG TTG CAT GAA AAG ATC CTG

Hs  CAA AAT CAT TTT GGA GGG AAG CGG CTT AGC CTT CTC TAT AAG GGT   90
Pt  CAA AAT CAT TTT GGA GGG AAG CGG CTT AGC CTT CTC TAT AAG GGT

Hs  AGT GTC CAT GGA TTC CGT AAT GGA GTT TTG CTT GAC AGA TGT TGT  135
Pt  AGT GTC CAT GGA TTC CAT AAT GGA GTT TTG CTT GAC AGA TGT TGT

Hs  AAT CAA GGG CCT ACT CTA ACA GTG ATT TAT AGT GAA GAT CAT ATT  180
Pt  AAT CAA GGG CCT ACT CTA ACA GTG ATT TAT AGT GAA GAT CAT ATT

Hs  ATT GGA GCA TAT GCA GAA GAG AGT TAC CAG GAA GGA AAG TAT GCT  225
Pt  ATT GGA GCA TAT GCA GAA GAG GGT TAC CAG GMA AGA AAG TAT GCT

Hs  TCC ATC ATC CTT TTT GCA CTT CAA GAT ACT AAA ATT TCA GAA TGG  270
Pt  TCC ATC ATC CTT TTT GCA CTT CAA GAG ACT AAA ATT TCA GAA TGG

Hs  AAA CTA GGA CTA TGT ACA CCA GAA ACA CTG TTT TGT TGT GAT GTT  315
Pt  AAA CTA GGA TAT TGT ACA CCA GAA ACA CTG TTT TGT TGT GAC GTT

Hs  ACA AAA TAT AAC TCC CCA ACT AAT TTC CAG ATA GAT GGA AGA AAT  360
Pt  GCA AAA TAT AAC TCC CCA ACT AAT TTC CAG ATA GAT GGA AGA AAT

Hs  AGA AAA GTG ATT ATG GAC TTA AAG ACA ATG GAA AAT CTT GGA CTT  405
Pt  AGA AAA GTG ATT ATG GAC TTA AAG ACA ATG GAA AAT CTT GGA CTT

Hs  GCT CAA AAT TGT ACT ATC TCT ATT CAG GAT TAT GAA GTT TTT CGA  450
Pt  GCT CAA AAT TGT ACT ATC TCT ATT CAG GAT TAT GAA GTT TTT CGA
```

FIGURE 16

| | | | | | | | | | | | | | | |
|---|---|---|---|---|---|---|---|---|---|---|---|---|---|---|
| Hs | TGC | GAA | GAT | TCA | CTG | GAT | GAA | AGA | AAG | ATA | AAA | GGG | GTC | ATT | GAG 495 |
| Pt | TGC | GAA | GAT | TCA | CTG | GAC | GAA | AGA | AAG | ATA | AAA | GGG | GTC | ATT | GAG |
| Hs | CTC | AGG | AAG | AGC | TTA | CTG | TCT | GCC | TTG | AGA | ACT | TAT | GAA | CCA | TAT 540 |
| Pt | CTC | AGG | AAG | AGC | TTA | CTG | TCT | GCC | TTG | AGA | ACT | TAT | GAA | CCA | TAT |
| Hs | GGA | TCC | CTG | GTT | CAA | CAA | ATA | CGA | ATT | CTC | CTG | GGT | CCA | ATT | 585 |
| Pt | GGA | TCC | CTG | GTT | CAA | CAA | ATA | CGA | ATT | CTG | CTG | GGT | CCA | ATT | |
| Hs | GGA | GCT | CCC | AAG | TCC | AGC | TTT | TTC | AAC | TCA | GTG | AGG | TCT | GTT | TTC 630 |
| Pt | GGA | GCT | GGG | AAG | TCT | AGC | TTT | TTC | AAC | TCA | GTG | AGG | TCT | GTT | TTC |
| Hs | CAA | GGG | CAT | GTA | ACG | CAT | CAG | GCT | TTG | GTG | GGC | ACT | AAT | ACA | ACT 675 |
| Pt | CAA | GGG | CAT | GTA | ACG | CAT | CAG | GCT | TTG | GTG | GGC | ACT | AAT | ACA | ACT |
| Hs | GGG | ATA | TCT | GAG | AAG | TAT | AGG | ACA | TAC | TCT | ATT | AGA | GAC | GGG | AAA 720 |
| Pt | GGG | ATA | TCT | GAG | AAG | TAT | AGG | ACA | TAC | TCT | ATT | AGA | GAC | GGG | AAA |
| Hs | GAT | GGC | AAA | TAC | CTG | CCG | TTT | ATT | CTG | TGT | GAC | TCA | CTG | GGG | CTG 765 |
| Pt | GAT | GGC | AAA | TAC | CTG | CCA | TTT | ATT | CTG | TGT | GAC | TCA | CTG | GGG | CTG |
| Hs | AGT | GAG | AAA | GAA | GGC | GGC | CTG | TGC | AGG | GAT | GAC | ATA | TTC | TAT | ATC 810 |
| Pt | AGT | GAG | AAA | GAA | GGC | GGC | CTG | TGC | ATG | GAT | GAC | ATA | TCC | TAC | ATC |
| Hs | TTG | AAC | GGT | AAC | ATT | CGT | GAT | AGA | TAC | CAG | TTT | AAT | CCC | ATG | GAA 855 |
| Pt | TTG | AAC | GGT | AAC | ATT | CGT | GAT | AGA | TAC | CAG | TTT | AAT | CCC | ATG | GAA |
| Hs | TCA | ATC | AAA | TTA | AAT | CAT | CAT | GAC | TAC | ATT | GAT | TCC | CCA | TCG | CTG 900 |
| Pt | TCA | ATC | AAA | TTA | AAT | CAT | CAT | GAC | TAC | ATT | GAT | TCC | CCA | TCG | CTG |

FIGURE 16 (CONT.)

```
Hs  AAG GAC AGA ATT CAT TGT GTG GCA TTT GTA TTT GAT GCC AGC TCT  945
Pt  AAG GAC AGA ATT CAT TGT GTG GCA TTT GTA TTT GAT GCC AGC TCT

Hs  ATT CAA TAC TTC TCC TCT CAG ATG ATA AAG ATC AAA AGA ATT  990
Pt  ATT GAA TAC TTC TCC TCT CAG ATG ATA AAG ATC AAA AGA ATT

Hs  CAA AGG GAG TTG GTA AAC GCT GGT GTG GTA CAT GTG GCT TTG CTC 1035
Pt  CGA AGG GAG TTG GTA AAC GCT GGT GTG GTA CAT GTG GCT TTG CTC

Hs  ACT CAT GTG GAT AGC ATG GAT TTG ATT ACA AAA GGT GAC CTT ATA 1080
Pt  ACT CAT GTG GAT AGC ATG GAT CTG ATT ACA AAA GGT GAC CTT ATA

Hs  GAA ATA GAG AGA TGT GAG CCT GTG AGG TCC AAG CTA GAG GAA GTC 1125
Pt  GAA ATA GAG AGA TGT GTG CCT GTG AGG TCC AAG CTA GAG GAA GTC

Hs  CAA AGA AAA CTT GGA TTT GCT CTT TCT GAC ATC TCG GTT AGC 1170
Pt  CAA AGA AAA CTT GGA TTT GCT CTT TCT GAC ATC TCG GTT AGC

Hs  AAT TAT TCC TCT GAG TGG GAG CTG GAC CCT GTA AAG GAT GTT CTA 1215
Pt  AAT TAT TCC TCT GAG TGG GAG CTG GAC CCT GTA AAG GAT GTT CTA

Hs  ATT CTT TCT GCT CTG AGA CGA ATG CTA TGG GCT GCA GAT GAC TTC 1260
Pt  ATT CTT TCT GCT CTG AGA CGA ATG CTA TGG GCT GCA GAT GAC TTC

Hs  TTA GAG GAT TTG CCT TTT GAG CAA ATA GGG AAT CTA AGG GAG GAA 1305
Pt  TTA GAG GAT TTG CCT TTT GAG CAA ATA GGG AAT CTA AGG GAG GAA

Hs  ATT ATC AAC TGT GCA CAA GGA AAA AAA TAG    (SEQ. ID. NO. 34) 1335
Pt  ATT ATC AAC TGT GCA CAA GGA AAA AAA TAG    (SEQ. ID. NO. 31)
```

METHODS FOR IDENTIFYING AGENTS THAT INCREASE THE P44 FUNCTION OF MICROTUBULE ASSEMBLY OR RESISTANCE TO HCV INFECTION

CROSS-REFERENCE TO RELATED APPLICATIONS

This application is a divisional of U.S. Ser. No. 10/098,600, filed Mar. 14, 2002, which is a continuation-in-part of copending U.S. Ser. No. 09/942,252, filed Aug. 28, 2001, which is a continuation-in-part of U.S. Ser. No. 09/591,435, filed Jun. 9, 2000, now U.S. Pat. No. 6,280,953, which is a continuation-in-part of U.S. patent application Ser. No. 09/240,915, filed Jan. 29, 1999, now U.S. Pat. No. 6,228,586, which claims priority from U.S. Provisional Patent Application Ser. No. 60/098,987, filed Sep. 2, 1998, and U.S. Provisional Patent Application Ser. No. 60/073,263, filed Jan. 30, 1998, each of which is incorporated herein in its entirety by reference.

TECHNICAL FIELD

This invention relates to using molecular and evolutionary techniques to identify polynucleotide and polypeptide sequences corresponding to evolved traits that may be relevant to human diseases or conditions, such as unique or enhanced human brain functions, longer human life spans, susceptibility or resistance to development of infectious disease (such as AIDS and hepatitis C), susceptibility or resistance to development of cancer, and aesthetic traits, such as hair growth, susceptibility or resistance to acne, or enhanced muscle mass.

BACKGROUND OF THE INVENTION

Humans differ from their closest evolutionary relatives, the non-human primates such as chimpanzees, in certain physiological and functional traits that relate to areas important to human health and well-being. For example, (1) humans have unique or enhanced brain function (e.g., cognitive skills, etc.) compared to chimpanzees; (2) humans have a longer life-span than non-human primates; (3) chimpanzees are resistant to certain infectious diseases that afflict humans, such as AIDS and hepatitis C; (4) chimpanzees appear to have a lower incidence of certain cancers than humans; (5) chimpanzees do not suffer from acne or alopecia (baldness); (6) chimpanzees have a higher percentage of muscle to fat; (7) chimpanzees are more resistant to malaria; (8) chimpanzees are less susceptible to Alzheimer=s disease; and (9) chimpanzees have a lower incidence of atherosclerosis. At the present time, the genes underlying the above human/chimpanzee differences are not known, nor, more importantly, are the specific changes that have evolved in these genes to provide these capabilities. Understanding the basis of these differences between humans and our close evolutionary relatives will provide useful information for developing effective treatments for related human conditions and diseases.

Classic evolution analysis, which compares mainly the anatomic features of animals, has revealed dramatic morphological and functional differences between human and non-human primates; yet, the human genome is known to share remarkable sequence similarities with that of other primates. For example, it is generally concluded that human DNA sequence is roughly 98.5% identical to chimpanzee DNA and only slightly less similar to gorilla DNA. McConkey and Goodman (1997) *TIG* 13:350-351. Given the relatively small percentage of genomic difference between humans and closely related primates, it is possible, if not likely, that a relatively small number of changes in genomic sequences may be responsible for traits of interest to human health and well-being, such as those listed above. Thus, it is desirable and feasible to identify the genes underlying these traits and to glean information from the evolved changes in the proteins they encode to develop treatments that could benefit human health and well-being. Identifying and characterizing these sequence changes is crucial in order to benefit from evolutionary solutions that have eliminated or minimized diseases or that provide unique or enhanced functions.

Recent developments in the human genome project have provided a tremendous amount of information on human gene sequences. Furthermore, the structures and activities of many human genes and their protein products have been studied either directly in human cells in culture or in several animal model systems, such as the nematode, fruit fly, zebrafish and mouse. These model systems have great advantages in being relatively simple, easy to manipulate, and having short generation times. Because the basic structures and biological activities of many important genes have been conserved throughout evolution, homologous genes can be identified in many species by comparing macromolecule sequences. Information obtained from lower species on important gene products and functional domains can be used to help identify the homologous genes or functional domains in humans. For example, the homeo domain with DNA binding activity first discovered in the fruit fly *Drosophila* was used to identify human homologues that possess similar activities.

Although comparison of homologous genes or proteins between human and a lower model organism may provide useful information with respect to evolutionarily conserved molecular sequences and functional features, this approach is of limited use in identifying genes whose sequences have changed due to natural selection. With the advent of the development of sophisticated algorithms and analytical methods, much more information can be teased out of DNA sequence changes. The most powerful of these methods, "$K_A/K_S$," involves pairwise comparisons between aligned protein-coding nucleotide sequences of the ratios of nonsynonymous nucleotide substitutions per nonsynonymous site ($K_A$)/synonymous substitutions per synonymous site ($K_S$)

(where nonsynonymous means substitutions that change the encoded amino acid and synonymous means substitutions that do not change the encoded amino acid). "$K_A/K_S$-type methods" includes this and similar methods. These methods have been used to demonstrate the occurrence of Darwinian molecular-level positive selection, resulting in amino acid differences in homologous proteins. Several groups have used such methods to document that a particular protein has evolved more rapidly than the neutral substitution rate, and thus supports the existence of Darwinian molecular-level positive selection. For example, McDonald and Kreitman (1991) *Nature* 351:652-654 propose a statistical test of neutral protein evolution hypothesis based on comparison of the number of amino acid replacement substitutions to synonymous substitutions in the coding region of a locus. When they apply this test to the Adh locus of three *Drosophila* species, they conclude that it shows instead that the locus has undergone adaptive fixation of selectively advantageous mutations and that selective fixation of adaptive mutations may be a viable alternative to the clocklike accumulation of neutral mutations as an explanation for most protein evolution. Jenkins et al. (1995) *Proc. R. Soc. Lond. B* 261:203-207 use the McDonald & Kreitman test to investigate whether adaptive evolution is occurring in sequences controlling transcription (non-coding sequences).

Nakashima et al. (1995) *Proc. Natl. Acad. Sci USA* 92:5606-5609, use the method of Miyata and Yasunaga to perform pairwise comparisons of the nucleotide sequences of ten PLA2 isozyme genes from two snake species; this method involves comparing the number of nucleotide substitutions per site for the noncoding regions including introns ($K_N$) and the $K_A$ and $K_S$. They conclude that the protein coding regions have been evolving at much higher rates than the noncoding regions including introns. The highly accelerated substitution rate is responsible for Darwinian molecular-level evolution of PLA2 isozyme genes to produce new physiological activities that must have provided strong selective advantage for catching prey or for defense against predators. Endo et al. (1996) *Mol. Biol. Evol.* 13(5):685-690 use the method of Nei and Gojobori, wherein $d_N$ is the number of nonsynonymous substitutions and $d_S$ is the number of synonymous substitutions, for the purpose of identifying candidate genes on which positive selection operates. Metz and Palumbi (1996) *Mol. Biol. Evol.* 13(2):397-406 use the McDonald & Kreitman test as well as a method attributed to Nei and Gojobori, Nei and Jin, and Kumar, Tamura, and Nei; examining the average proportions of $P_n$, the replacement substitutions per replacement site, and $P_s$, the silent substitutions per silent site, to look for evidence of positive selection on bindin genes in sea urchins to investigate whether they have rapidly evolved as a prelude to species formation. Goodwin et al. (1996) *Mol. Biol. Evol.* 13(2):346-358 uses similar methods to examine the evolution of a particular murine gene family and conclude that the methods provide important fundamental insights into how selection drives genetic divergence in an experimentally manipulatable system. Edwards et al. (1995) use degenerate primers to pull out MHC loci from various species of birds and an alligator species, which are then analyzed by the Nei and Gojobori methods ($d_N$:$d_S$ ratios) to extend MHC studies to nonmammalian vertebrates. Whitfield et al. (1993) *Nature* 364:713-715 use Ka/Ks analysis to look for directional selection in the regions flanking a conserved region in the SRY gene (that determines male sex). They suggest that the rapid evolution of SRY could be a significant cause of reproductive isolation, leading to new species. Wettsetin et al. (1996) *Mol. Biol. Evol.* 13(1):56-66 apply the MEGA program of Kumar, Tamura and Nei and phylogenetic analysis to investigate the diversification of MHC class I genes in squirrels and related rodents. Parham and Ohta (1996) *Science* 272:67-74 state that a population biology approach, including tests for selection as well as for gene conversion and neutral drift are required to analyze the generation and maintenance of human MHC class I polymorphism. Hughes (1997) *Mol. Biol. Evol.* 14(1):1-5 compared over one hundred orthologous immunoglobulin C2 domains between human and rodent, using the method of Nei and Gojobori ($d_N$:$d_S$ ratios) to test the hypothesis that proteins expressed in cells of the vertebrate immune system evolve unusually rapidly. Swanson and Vacquier (1998) *Science* 281: 710-712 use $d_N$:$d_S$ ratios to demonstrate concerted evolution between the lysin and the egg receptor for lysin and discuss the role of such concerted evolution in forming new species (speciation).

Due to the distant evolutionary relationships between humans and these lower animals, the adaptively valuable genetic changes fixed by natural selection are often masked by the accumulation of neutral, random mutations over time. Moreover, some proteins evolve in an episodic manner; such episodic changes could be masked, leading to inconclusive results, if the two genomes compared are not close enough. Messier and Stewart (1997) *Nature* 385:151-154. In fact, studies have shown that the occurrence of adaptive selection in protein evolution is often underestimated when predominantly distantly related sequences are compared. Endo et al. (1996) *Mol. Biol. Evol.* 37:441-456; Messier and Stewart (1997) *Nature* 385:151-154.

Molecular evolution studies within the primate family have been reported, but these mainly focus on the comparison of a small number of known individual genes and gene products to assess the rates and patterns of molecular changes and to explore the evolutionary mechanisms responsible for such changes. See generally, Li, *Molecular Evolution*, Sinauer Associates, Sunderland, Mass., 1997. Furthermore, sequence comparison data are used for phylogenetic analysis, wherein the evolution history of primates is reconstructed based on the relative extent of sequence similarities among examined molecules from different primates. For example, the DNA and amino acid sequence data for the enzyme lysozyme from different primates were used to study protein evolution in primates and the occurrence of adaptive selection within specific lineages. Malcolm et al. (1990) *Nature* 345:86-89; Messier and Stewart (1997). Other genes that have been subjected to molecular evolution studies in primates include hemoglobin, cytochrome c oxidase, and major histocompatibility complex (MHC). Nei and Hughes in: *Evolution at the Molecular Level*, Sinauer Associates, Sunderland, Mass. 222-247, 1991; Lienert and Parham (1996) *Immunol. Cell Biol.* 74:349-356; Wu et al. (1997) *J. Mol. Evol.* 44:477-491. Many non-coding sequences have also been used in molecular phylogenetic analysis of primates. Li, *Molecular Evolution*, Sinauer Associates, Sunderland, Mass. 1997. For example, the genetic distances among primate lineages were estimated from orthologous non-coding nucleotide sequences of beta-type globin loci and their flanking regions, and the evolution tree constructed for the nucleotide sequence orthologues depicted a branching pattern that is largely congruent with the picture from phylogenetic analyses of morphological characters. Goodman et al. (1990) *J. Mol. Evol.* 30:260-266.

Zhou and Li (1996) *Mol. Biol. Evol.* 13(6):780-783 applied $K_A/K_S$ analysis to primate genes. It had previously been reported that gene conversion events likely have occurred in introns 2 and 4 between the red and green retinal pigment genes during human evolution. However, intron 4 sequences of the red and green retinal pigment genes from one European human were completely identical, suggesting a recent gene conversion event. In order to determine if the gene conversion event occurred in that individual, or a common ancestor of Europeans, or an even earlier hominid ancestor, the authors sequenced intron 4 of the red and green pigment gene from a male Asian human, a male chimpanzee, and a male baboon, and applied $K_A/K_S$ analysis. They observed that the divergence between the two genes is significantly lower in intron 4 than in surrounding exons, suggesting that strong natural selection has acted against sequence homogenization.

Wolinsky et al. (1996) *Science* 272:537-542 used comparisons of nonsynonymous to synonymous base substitutions to demonstrate that the HIV virus itself (i.e., not the host species) is subject to adaptive evolution within individual human patients. Their goal was simply to document the occurrence of positive selection in a short time frame (that of a human patient=s course of disease). Niewiesk and Bangham (1996) *J Mol Evol* 42:452-458 used the $D_n/D_s$ approach to ask a related question about the HTLV-1 virus, i.e., what are the selective forces acting on the virus itself. Perhaps because of an insufficient sample size, they were unable to resolve the nature of the selective forces. In both of these cases, although $K_A/K_S$-type methods were used in relation to a human virus, no attempt was made to use these methods for therapeutic goals (as in the present application), but rather to pursue narrow academic goals.

As can be seen from the papers cited above, analytical methods of molecular evolution to identify rapidly evolving genes ($K_A/K_S$-type methods) can be applied to achieve many different purposes, most commonly to confirm the existence of Darwinian molecular-level positive selection, but also to assess the frequency of Darwinian molecular-level positive selection, to understand phylogenetic relationships, to elucidate mechanisms by which new species are formed, or to establish single or multiple origin for specific gene polymorphisms. What is clear is from the papers cited above and others in the literature is that none of the authors applied $K_A/K_S$-type methods to identify evolutionary solutions, specific evolved changes, that could be mimicked or used in the development of treatments to prevent or cure human conditions or diseases or to modulate unique or enhanced human functions. They have not used $K_A/K_S$ type analysis as a systematic tool for identifying human or non-human primate genes that contain evolutionarily significant sequence changes and exploiting such genes and the identified changes in the development of treatments for human conditions or diseases.

The identification of human genes that have evolved to confer unique or enhanced human functions compared to homologous chimpanzee genes could be applied to developing agents to modulate these unique human functions or to restore function when the gene is defective. The identification of the underlying chimpanzee (or other non-human primate) genes and the specific nucleotide changes that have evolved, and the further characterization of the physical and biochemical changes in the proteins encoded by these evolved genes, could provide valuable information, for example, on what determines susceptibility and resistance to infectious viruses, such as HIV and HCV, what determines susceptibility or resistance to the development of certain cancers, what determines susceptibility or resistance to acne, how hair growth can be controlled, and how to control the formation of muscle versus fat. This valuable information could be applied to developing agents that cause the human proteins to behave more like their chimpanzee homologues.

All references cited herein are hereby incorporated by reference in their entirety.

SUMMARY OF THE INVENTION

The present invention provides methods for identifying polynucleotide and polypeptide sequences having evolutionarily significant changes which are associated with physiological conditions, including medical conditions. The invention applies comparative primate genomics to identify specific gene changes which may be associated with, and thus responsible for, physiological conditions, such as medically or commercially relevant evolved traits, and using the information obtained from these evolved genes to develop human treatments. The non-human primate sequences employed in the methods described herein may be any non-human primate, and are preferably a member of the hominoid group, more preferably a chimpanzee, bonobo, gorilla and/or orangutan, and most preferably a chimpanzee.

In one preferred embodiment, a non-human primate polynucleotide or polypeptide has undergone natural selection that resulted in a positive evolutionarily significant change (i.e., the non-human primate polynucleotide or polypeptide has a positive attribute not present in humans). In this embodiment the positively selected polynucleotide or polypeptide may be associated with susceptibility or resistance to certain diseases or with other commercially relevant traits. Examples of this embodiment include, but are not limited to, polynucleotides and polypeptides that are positively selected in non-human primates, preferably chimpanzees, that may be associated with susceptibility or resistance to infectious diseases and cancer. An example of a commercially relevant trait may include aesthetic traits such as hair growth, muscle mass, susceptibility or resistance to acne. An example of the disease resistance/susceptibility embodiment includes polynucleotides and polypeptides associated with the susceptibility or resistance to HIV dissemination, propagation and/or development of AIDS. The present invention can thus be useful in gaining insight into the molecular mechanisms that underlie resistance to HIV dissemination, propagation and/or development of AIDS, providing information that can also be useful in discovering and/or designing agents such as drugs that prevent and/or delay development of AIDS. Specific genes that have been positively selected in chimpanzees that may relate to AIDS or other infectious diseases are ICAM-1, ICAM-2, ICAM-3, MIP-1-α, CD59 and DC-SIGN. 17-β-hydroxysteroid dehydrogenase Type IV is a specific gene has been positively selected in chimpanzees that may relate to cancer. Additionally, the p44 gene is a gene that has been positively selected in chimpanzees and is believed to contribute to their HCV resistance.

In another preferred embodiment, a human polynucleotide or polypeptide has undergone natural selection that resulted in a positive evolutionarily significant change (i.e., the human polynucleotide or polypeptide has a positive attribute not present in non-human primates). One example of this embodiment is that the polynucleotide or polypeptide may be associated with unique or enhanced functional capabilities of the human brain compared to non-human primates. Another is the longer life-span of humans compared to non-human primates. A third is a commercially important aesthetic trait (e.g., normal or enhanced breast development). The present invention can thus be useful in gaining insight into the molecular mechanisms that underlie unique or enhanced human functions or physiological traits, providing information which can also be useful in designing agents such as drugs that modulate such unique or enhanced human functions or traits, and in designing treatment of diseases or conditions related to humans. As an example, the present invention can thus be useful in gaining insight into the molecular mechanisms that underlie human cognitive function, providing information which can also be useful in designing agents such as drugs that enhance human brain function, and in designing treatment of diseases related to the human brain. A specific example of a human gene that has positive evolutionarily significant changes when compared to non-human primates is a tyrosine kinase gene, the KIAA0641 or NM_004920 gene.

Accordingly, in one aspect, the invention provides methods for identifying a polynucleotide sequence encoding a polypeptide, wherein said polypeptide may be associated with a physiological condition (such as a medically or commercially relevant positive evolutionarily significant change). The positive evolutionarily significant change can be found in humans or in non-human primates. In a preferred embodiment the invention provides a method for identifying a human AATYK polynucleotide sequence encoding a human AATYK polypeptide associated with an evolutionarily significant change. In another preferred embodiment, the invention provides a method for identifying a p44 polynucleotide and polypeptide that are associated with enhanced HCV resistance in chimpanzees relative to humans.

For any embodiment of this invention, the physiological condition may be any physiological condition, including those listed herein, such as, for example, disease (including susceptibility or resistance to disease) such as cancer, infectious disease (including viral diseases such as AIDS or HCV-associated chronic hepatitis); life span; brain function, including cognitive function or developmental sculpting; and aesthetic or cosmetic qualities, such as enhanced breast development.

In one aspect of the invention, methods are provided for identifying a polynucleotide sequence encoding a human polypeptide, wherein said polypeptide may be associated with a physiological condition that is present in human(s), comprising the steps of: a) comparing human protein-coding polynucleotide sequences to protein-coding polynucleotide sequences of a non-human primate, wherein the non-human primate does not have the physiological condition (or has it to a lesser degree); and b) selecting a human polynucleotide sequence that contains a nucleotide change as compared to corresponding sequence of the non-human primate, wherein said change is evolutionarily significant. In some embodiments, the human protein coding sequence (and/or the polypeptide encoded therein) may be associated with development and/or maintenance of a physiological condition or trait or a biological function. In some embodiments, the physiological condition or biological function may be life span, brain or cognitive function, or breast development (including adipose, gland and duct development). Methods used to assess the nucleotide change, and the nature(s) of the nucleotide change, are described herein, and apply to any and all embodiments. In a preferred embodiment, the method is a method for identifying a human AATYK polynucleotide sequence encoding a human AATYK polypeptide.

In other embodiments, methods are provided that comprise the steps of: (a) comparing human protein-coding nucleotide sequences to protein-coding nucleotide sequences of a non-human primate, preferably a chimpanzee, that is resistant to a particular medically relevant disease state, wherein the human protein coding sequence is or is believed to be associated with development of the disease; and (b) selecting a non-human polynucleotide sequence that contains at least one nucleotide change as compared to the corresponding sequence of the human, wherein the change is evolutionarily significant. The sequences identified by these methods may be further characterized and/or analyzed to confirm that they are associated with the development of the disease state or condition. The most preferred disease states that are applicable to these methods are cancer and infectious diseases, including AIDS, hepatitis C and leprosy.

In one embodiment, chimpanzee polynucleotide sequences are compared to human polynucleotide sequences to identify a p44 sequence that is evolutionarily significant. The p44 protein is (or is believed to be) associated with the enhanced HCV resistance of chimpanzees relative to humans.

In another aspect, methods are provided for identifying an evolutionarily significant change in a human brain polypeptide-coding polynucleotide sequence, comprising the steps of a) comparing human brain polypeptide-coding polynucleotide sequences to corresponding sequences of a non-human primate; and b) selecting a human polynucleotide sequence that contains a nucleotide change as compared to corresponding sequence of the non-human primate, wherein said change is evolutionarily significant. In some embodiments, the human brain polypeptide coding nucleotide sequences correspond to human brain cDNAs. In preferred embodiments, the human brain polypeptide-coding polynucleotide sequence is an AATYK sequence.

Another aspect of the invention includes methods for identifying a positively selected human evolutionarily significant change. These methods comprise the steps of: (a) comparing human polypeptide-coding nucleotide sequences to polypeptide-coding nucleotide sequences of a non-human primate; and (b) selecting a human polynucleotide sequence that contains at least one (i.e., one or more) nucleotide change as compared to corresponding sequence of the non-human primate, wherein said change is evolutionarily significant. The sequences identified by this method may be further characterized and/or analyzed for their possible association with biologically or medically relevant functions or traits unique or enhanced in humans. In preferred embodiments, the human polypeptide-coding nucleotide sequence is an AATYK sequence.

Another embodiment of the present invention is a method for large scale sequence comparison between human polypeptide-coding polynucleotide sequences and the polypeptide-coding polynucleotide sequences from a non-human primate, e.g., chimpanzee, comprising: (a) aligning the human polynucleotide sequences with corresponding polynucleotide sequences from non-human primate according to sequence homology; and (b) identifying any nucleotide changes within the human sequences as compared to the homologous sequences from the non-human primate, wherein the changes are evolutionarily significant. In some embodiments, the protein coding sequences are from brain.

In some embodiments, a nucleotide change identified by any of the methods described herein is a non-synonymous substitution. In some embodiments, the evolutionary significance of the nucleotide change is determined according to the non-synonymous substitution rate ($K_A$) of the nucleotide sequence. In some embodiments, the evolutionarily significant changes are assessed by determining the $K_A/K_S$ ratio between the human gene and the homologous gene from non-human primate (such as chimpanzee), and preferably that ratio is at least about 0.75, more preferably greater than about 1 (unity) (i.e., at least about 1), more preferably at least about 1.25, more preferably at least about 1.50, and more preferably at least about 2.00. In other embodiments, once a positively selected gene has been identified between human and a non-human primate (such as chimpanzee or gorilla), further comparisons are performed with other non-human primates to confirm whether the human or the non-human primate (such as chimpanzee or gorilla) gene has undergone positive selection.

In another aspect, the invention provides methods for correlating an evolutionarily significant human nucleotide change to a physiological condition in a human (or humans), which comprise analyzing a functional effect (which includes determining the presence of a functional effect), if any, of (the presence or absence of) a polynucleotide sequence identified by any of the methods described herein, wherein presence of a functional effect indicates a correlation between the evolutionarily significant nucleotide change and the physiological condition. Alternatively, in these methods, a functional effect (if any) may be assessed using a polypeptide sequence (or a portion of the polypeptide sequence) encoded by a nucleotide sequence identified by any of the methods described herein.

In a preferred embodiment, the polynucleotide sequence or polypeptide sequence is a human or chimpanzee p44 polynucleotide sequence (SEQ ID NO. 34 OR 31) or polypeptide sequence (SEQ ID NO. 36 OR 33). In a more preferred embodiment, the p44 polynucleotide sequences are the exon 2 sequences having nucleotides 1-457 of SEQ ID NO:34 (human), and nucleotides 1-457 of SEQ ID NO:31 (chimpanzee), or fragments thereof containing the exon 2 evolutionarily significant chimpanzee nucleotides or the corresponding human nucleotides. Such fragments are preferably between 18 and 225 nucleotides in length.

The present invention also provides comparison of the identified polypeptides by physical and biochemical methods widely used in the art to determine the structural or biochemical consequences of the evolutionarily significant changes. Physical methods are meant to include methods that are used to examine structural changes to proteins encoded by genes found to have undergone adaptive evolution. Side-by-side comparison of the three-dimensional structures of a protein (either human or non-human primate) and the evolved homologous protein (either non-human primate or human, respectively) will provide valuable information for developing treatments for related human conditions and diseases. For example, using the methods of the present invention, the chimpanzee ICAM-1 gene was identified as having positive evolutionary changes compared to human ICAM-1. In a three-dimensional model of two functional domains of the human ICAM-1 protein it can be seen that five of the six amino acids that have been changed in chimpanzees are immediately adjacent to (i.e., physically touching) amino acid residues known to be crucial for binding to the ICAM-1 counter-receptor, LFA-1; in each case, the human amino acid has been replaced by a larger amino acid in the chimpanzee ICAM-1. Such information allows insight into designing appropriate therapeutic intervention(s). Accordingly, in another aspect, the invention provides methods for identifying a target site (which includes one or more target sites) which may be suitable for therapeutic intervention, comprising comparing a human polypeptide (or a portion of the polypeptide) encoded in a sequence identified by any of the methods described herein, with a corresponding non-human polypeptide (or a portion of the polypeptide), wherein a location of a molecular difference, if any, indicates a target site.

Likewise, human and chimpanzee p44 polypeptide computer models or x-ray crystallography structures can be compared to determine how the evolutionarily significant amino acid changes of the chimpanzee p44 exon 2 alter the protein's structure, and how agents might be designed to interact with human p44 in such a manner that permits it to mimic chimpanzee p44 structure and/or function.

In another aspect, the invention provides methods for identifying a target site (which includes one or more target sites) which may be suitable for therapeutic intervention, comprising comparing a human polypeptide (or a portion of the polypeptide) encoded in a sequence identified by any of the methods described herein, with a corresponding non-human primate polypeptide (or a portion of the polypeptide), wherein a location of a molecular difference, such as an amino acid difference, if any, indicates a target site. Target sites can also be nonsynonymous nucleotide changes observed between a positively selected polynucleotide identified by any of the methods described herein and its corresponding sequence in the human or non-human primate. In preferred embodiments, the target site is a site on a human p44 polypeptide.

Biochemical methods are meant to include methods that are used to examine functional differences, such as binding specificity, binding strength, or optimal binding conditions, for a protein encoded by a gene that has undergone adaptive evolution. Side-by-side comparison of biochemical characteristics of a protein (either human or non-human primate) and the evolved homologous protein (either non-human primate or human, respectively) will reveal valuable information for developing treatments for related human conditions and diseases.

In another aspect, the invention provides methods of identifying an agent which may modulate a physiological condition, said method comprising contacting an agent (i.e., at least one agent to be tested) with a cell that has been transfected with a polynucleotide sequence identified by any of the methods described herein, wherein an agent is identified by its ability to modulate function of the polynucleotide sequence. In other embodiments, the invention provides methods of identifying an agent which may modulate a physiological condition, said method comprising contacting an agent (i.e., at least one agent) to be tested with a polypeptide (or a fragment of a polypeptide and/or a composition comprising a polypeptide or fragment of a polypeptide) encoded in or within a polynucleotide identified by any of the methods described herein, wherein an agent is identified by its ability to modulate function of the polypeptide. In preferred embodiments of these methods the polynucleotide sequence is an evolutionarily significant chimpanzee p44 polynucleotide sequence or its corresponding human polynucleotide. In more preferred embodiments, the polynucleotide sequence is nucleotides 1-457 of SEQ ID NO:31 (chimpanzee), and nucleotides 1-458 of SEQ ID NO:34 (human), or fragments thereof containing preferably 18-225 nucleotides and at least one of the chimpanzee evolutionarily significant nucleotides or corresponding human nucleotides. The invention also provides agents which are identified using the screening methods described herein.

In another aspect, the invention provides methods of screening agents which may modulate the activity of the human polynucleotide or polypeptide to either modulate a unique or enhanced human function or trait or to mimic the non-human primate trait of interest, such as susceptibility or resistance to development of a disease, such as HCV-associated chronic hepatitis or AIDS. These methods comprise contacting a cell which has been transfected with a polynucleotide sequence with an agent to be tested, and identifying agents based on their ability to modulate function of the polynucleotide or contacting a polypeptide preparation with an agent to be tested and identifying agents based upon their ability to modulate function of the polypeptide. In preferred embodiments, the polynucleotide sequence is an evolutionarily significant chimpanzee p44 polynucleotide sequence or its corresponding human polynucleotide sequence. In more preferred embodiments, the polynucleotide sequence is nucleotides 1-457 of SEQ ID NO: 31 (chimpanzee), or nucleotides 1-457 of SEQ ID NO:34 (human), or fragments thereof containing preferably 18-225 nucleotides and at least one of the chimpanzee evolutionarily significant nucleotides or corresponding human nucleotides.

In another aspect of the invention, methods are provided for identifying candidate polynucleotides that may be associated with decreased resistance to development of a disease in humans, comprising comparing the human polynucleotide sequence with the corresponding non-human primate polynucleotide sequence to identify any nucleotide changes; and determining whether the human nucleotide changes are evolutionarily significant. It has been observed that human polynucleotides that are evolutionarily significant may, in some instances, be associated with increased susceptibility or decreased resistance to the development of human diseases such as cancer. As is described herein, the strongly positively selected BRCA1 gene's exon 11 is also the location of a number of mutations associated with breast, ovarian and/or prostate cancer. Thus, this phenomenon may represent a trade-off between enhanced development of one trait and loss or reduction in another trait in polynucleotides encoding polypeptides of multiple functions. In this way, identification of positively selected human polynucleotides can serve to identify a pool of genes that are candidates for susceptibility to human diseases.

Human candidate evolutionarily significant polynucleotides that are identified in this manner can be evaluated for their role in conferring susceptibility to diseases by analyzing the functional effect of the evolutionarily significant nucleotide change in the candidate polynucleotide in a suitable model system. The presence of a functional effect in the model system indicates a correlation between the nucleotide change in the candidate polynucleotide and the decreased resistance to development of the disease in humans. For example, if an evolutionarily significant polynucleotide containing all the evolutionarily significant nucleotide changes, or a similar polynucleotide with a lesser number of nucleotide changes, is found to increase the susceptibility to the disease at issue in a non-human primate model, this would be a functional effect that correlates the nucleotide change and the disease.

Alternatively, human candidate evolutionarily significant polynucleotides may, in some individuals, have mutations aside from the evolutionarily significant nucleotide changes, that confer the increased susceptibility to the disease. These mutations can be tested in a suitable model system for a functional effect, such as conversion to a neoplastic phenotype, to correlate the mutation to the disease.

Further, the subject method includes a diagnostic method to determine whether a human patient is predisposed to decreased resistance to the development of a disease, by assaying the patient's nucleic acids for the presence of a mutation in an evolutionarily significant polynucleotide, where the presence of the mutation in the polynucleotide has been determined by methods described herein as being diagnostic for decreased resistance to the development of the disease. In one embodiment, the polynucleotide is BRCA1 exon 11, and the disease is breast, prostate or ovarian cancer.

BRIEF DESCRIPTION OF THE DRAWINGS

FIG. 2 (SEQ ID NOS:1-3) is a nucleotide sequence alignment between human and chimpanzee ICAM-1 sequences (GenBank® accession numbers X06990 and X86848, respectively). The amino acid translation of the chimpanzee sequence is shown below the alignment.

FIG. 3 shows the nucleotide sequence of gorilla ICAM-1 (SEQ ID NO:4).

FIG. 4 shows the nucleotide sequence of orangutan ICAM-1 (SEQ ID NO:5).

FIGS. 5(A)-(E) show the polypeptide sequence alignment of ICAM-1 from several primate species (SEQ ID NO:6).

FIGS. 6(A)-(B) show the polypeptide sequence alignment of ICAM-2 from several primate species (SEQ ID NO:7).

FIGS. 7(A)-(D) show the polypeptide sequence alignment of ICAM-3 from several primate species (SEQ ID NO:8).

FIG. 11 shows the coding sequence of human DC-SIGN (Genbank Acc. No. M98457) (SEQ. ID. NO. 9).

FIG. 12 shows the coding sequence of chimpanzee DC-SIGN (SEQ. ID. NO. 10).

FIG. 13 shows the coding sequence of gorilla DC-SIGN (SEQ. ID. NO. 11).

FIG. 14A shows the nucleotide sequence of the human AATYK gene. Start and stop codons are underlined (SEQ ID NO:14).

FIG. 14B shows an 1207 amino acid sequence of the human AATYK gene (SEQ ID NO:16).

FIG. 15A shows an 1806 base-pair region of the chimp AATYK gene (SEQ ID NO:17).

FIG. 15B shows an 1785 base-pair region of the gorilla AATYK gene (SEQ ID NO:18).

FIG. 16 shows a 1335 nucleotide region of the aligned chimpanzee (SEQ ID NO:31) and human (SEQ IS NO:34) p44 gene coding region. The underlined portion is exon 2, which was determined to be evolutionarily significant. Nonsynonymous differences between the two sequences are indicated in bold, synonymous differences in italics. Chimpanzee has a single heterozygous base (position 212), shown as M (IUPAC code for A or C. The C base represents a nonsynonymous difference from human, while A is identical to the same position in the human homolog. Thus, these two chimpanzee alleles differ slightly in the $K_A/K_S$ ratios relative to human p44.

DETAILED DESCRIPTION OF THE INVENTION

Figure 1:
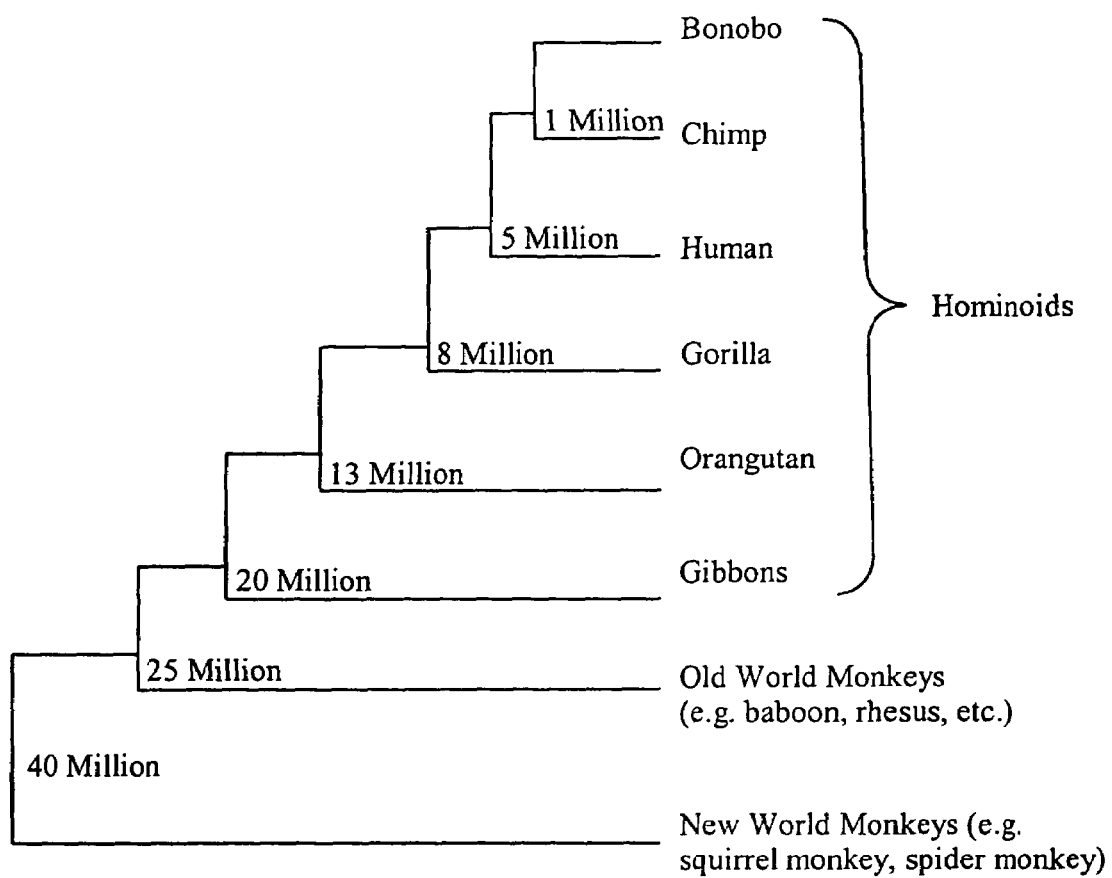
FIG. 1 depicts a phylogenetic tree for primates within the hominoid group. The branching orders are based on well-supported mitochondrial DNA phylogenies. Messier and Stewart (1997) *Nature* 385:151-154.
Figure 8:
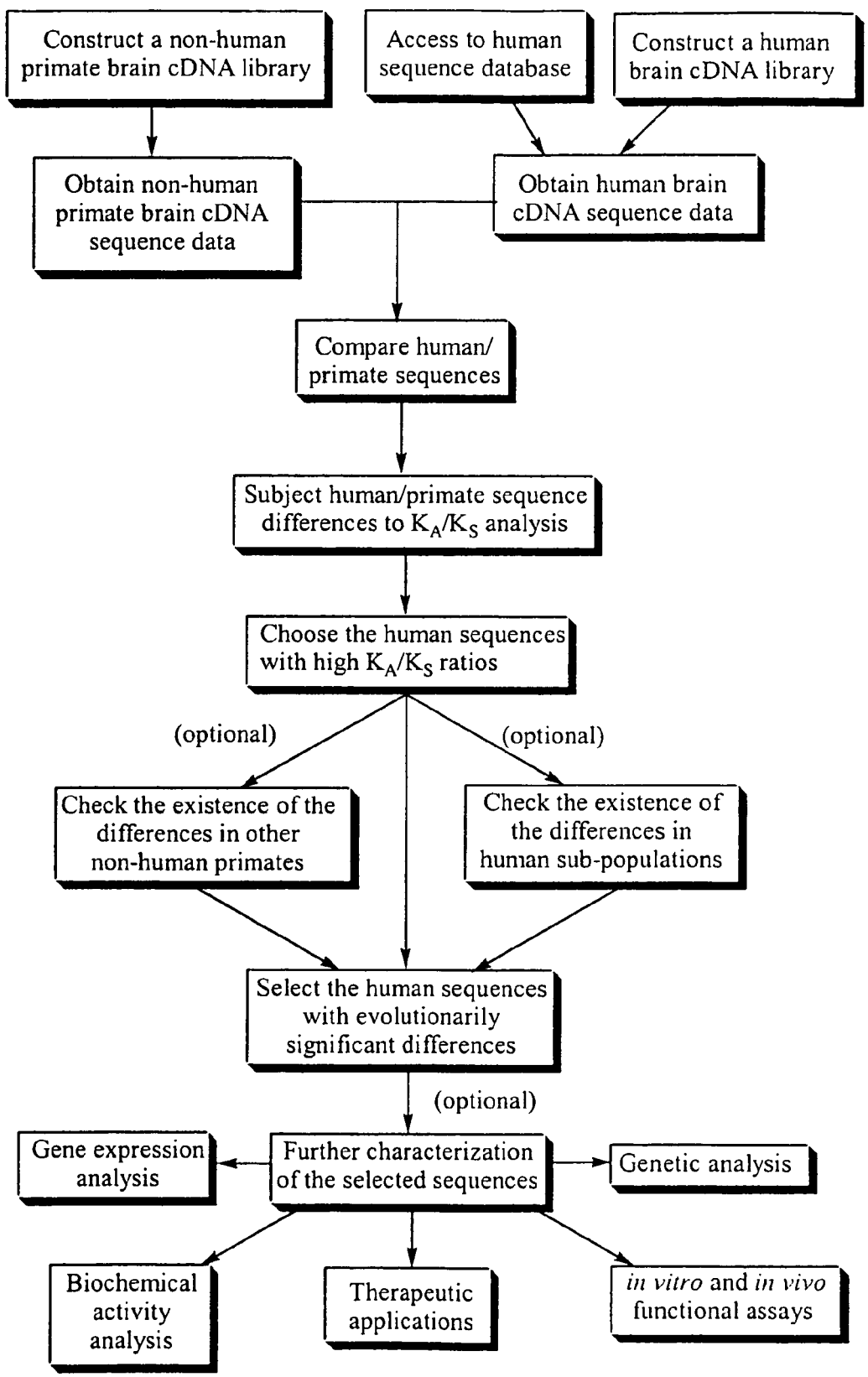
FIG. 8 depicts a schematic representation of a procedure for comparing human/primate brain polynucleotides, selecting sequences with evolutionarily significant changes, and further characterizing the selected sequences. The diagram of FIG. 8 illustrates a preferred embodiment of the invention and together with the description serves to explain the principles of the invention, along with elaboration and optional additional steps. It is understood that any human/primate polynucleotide sequence can be compared by a similar procedure and that the procedure is not limited to brain polynucleotides.

The present invention applies comparative genomics to identify specific gene changes which are associated with, and thus may contribute to or be responsible for, physiological conditions, such as medically or commercially relevant evolved traits. The invention comprises a comparative genomics approach to identify specific gene changes responsible for differences in functions and diseases distinguishing humans from other non-humans, particularly primates, and most preferably chimpanzees, including the two known species, common chimpanzees and bonobos (pygmy chimpanzees). For example, chimpanzees and humans are 98.5% identical at the DNA sequence level and the present invention can identify the adaptive molecular changes underlying differences between the species in a number of areas, including unique or enhanced human cognitive abilities or physiological traits and chimpanzee resistance to HCV, AIDS and certain cancers. Unlike traditional genomics, which merely identifies genes, the present invention provides exact information on evolutionary solutions that eliminate disease or provide unique or enhanced functions or traits. The present invention identifies genes that have evolved to confer an evolutionary advantage and the specific evolved changes.

The present invention results from the observation that human protein-coding polynucleotides may contain sequence changes that are found in humans but not in other evolutionarily closely related species such as non-human primates, as a result of adaptive selection during evolution.

The present invention further results from the observation that the genetic information of non-human primates may contain changes that are found in a particular non-human primate but not in humans, as a result of adaptive selection during evolution. In this embodiment, a non-human primate polynucleotide or polypeptide has undergone natural selection that resulted in a positive evolutionarily significant change (i.e., the non-human primate polynucleotide or polypeptide has a positive attribute not present in humans). In this embodiment the positively selected polynucleotide or polypeptide may be associated with susceptibility or resistance to certain diseases or other commercially relevant traits. Medically relevant examples of this embodiment include, but are not limited to, polynucleotides and polypeptides that are positively selected in non-human primates, preferably chimpanzees, that may be associated with susceptibility or resistance to infectious diseases and cancer. An example of this embodiment includes polynucleotides and polypeptides associated with the susceptibility or resistance to progression from HIV infection to development of AIDS. The present invention can thus be useful in gaining insight into the molecular mechanisms that underlie resistance to progression from HIV infection to development of AIDS, providing information that can also be useful in discovering and/or designing agents such as drugs that prevent and/or delay development of AIDS. Likewise, the present invention can be useful in gaining insight into the underlying mechanisms for HCV resistance in chimpanzees as compared to humans. Commercially relevant examples include, but are not limited to, polynucleotides and polypeptides that are positively selected in non-human primates that may be associated with aesthetic traits, such as hair growth, absence of acne or muscle mass.

Positively selected human evolutionarily significant changes in polynucleotide and polypeptide sequences may be attributed to human capabilities that provide humans with competitive advantages, particularly when compared to the closest evolutionary relative, chimpanzee, such as unique or enhanced human brain functions. The present invention identifies human genes that evolved to provide unique or enhanced human cognitive abilities and the actual protein changes that confer functional differences will be quite useful in therapeutic approaches to treat cognitive deficiencies as well as cognitive enhancement for the general population.

Other positively selected human evolutionarily significant changes include those sequences that may be attributed to human physiological traits or conditions that are enhanced or unique relative to close evolutionary relatives, such as the chimpanzee, including enhanced breast development. The present invention provides a method of determining whether a polynucleotide sequence in humans that may be associated with enhanced breast development has undergone an evolutionarily significant change relative to a corresponding polynucleotide sequence in a closely related non-human primate. The identification of evolutionarily significant changes in the human polynucleotide that is involved in the development of unique or enhanced human physiological traits is important in the development of agents or drugs that can modulate the activity or function of the human polynucleotide or its encoded polypeptide.

The practice of the present invention employs, unless otherwise indicated, conventional techniques of molecular biology, genetics and molecular evolution, which are within the skill of the art. Such techniques are explained fully in the literature, such as: "Molecular Cloning: A Laboratory Manual", second edition (Sambrook et al., 1989); "Oligonucleotide Synthesis" (M. J. Gait. ed., 1984); "Current Protocols in Molecular Biology" (F. M. Ausubel et al., eds., 1987); "PCR: The Polymerase Chain Reaction", (Mullis et al., eds., 1994); "Molecular Evolution", (Li, 1997).

Definitions

As used herein, a "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides. The terms "polynucleotide" and "nucleotide sequence" are used interchangeably.

As used herein, a "gene" refers to a polynucleotide or portion of a polynucleotide comprising a sequence that encodes a protein. It is well understood in the art that a gene also comprises non-coding sequences, such as 5= and 3= flanking sequences (such as promoters, enhancers, repressors, and other regulatory sequences) as well as introns.

The terms "polypeptide," "peptide," and "protein" are used interchangeably herein to refer to polymers of amino acids of any length. These terms also include proteins that are post-translationally modified through reactions that include glycosylation, acetylation and phosphorylation.

A "physiological condition" is a term well-understood in the art and means any condition or state that can be measured and/or observed. A "physiological condition" includes, but is not limited to, a physical condition, such as degree of body fat, alopecia (baldness), acne or enhanced breast development; life-expectancy; disease states (which include susceptibility and/or resistance to diseases), such as cancer or infectious diseases. Examples of physiological conditions are provided below (see, e.g., definitions of "human medically relevant medical condition", "human commercially relevant condition", "medically relevant evolved trait", and "commercially relevant evolved trait") and throughout the specification, and it is understood that these terms and examples refer to a physiological condition. A physiological condition may be, but is not necessarily, the result of multiple factors, any of which in turn may be considered a physiological condition. A physiological condition which is "present" in a human or non-human primate occurs within a given population, and includes those physiological conditions which are unique and/or enhanced in a given population when compared to another population.

The terms "human medically relevant condition" or "human commercially relevant condition" are used herein to refer to human conditions for which medical or non-medical intervention is desired.

The term "medically relevant evolved trait" is used herein to refer to traits that have evolved in humans or non-human primates whose analysis could provide information (e.g., physical or biochemical data) relevant to the development of a human medical treatment.

The term "commercially relevant evolved trait" is used herein to refer to traits that have evolved in humans or non-human primates whose analysis could provide information (e.g., physical or biochemical data) relevant to the development of a medical or non-medical product or treatment for human use.

The term "$K_A/K_S$-type methods" means methods that evaluate differences, frequently (but not always) shown as a ratio, between the number of nonsynonymous substitutions and synonymous substitutions in homologous genes (including the more rigorous methods that determine non-synonymous and synonymous sites). These methods are designated using several systems of nomenclature, including but not limited to $K_A/K_S$, $d_N/d_S$, $D_N/D_S$.

The terms "evolutionarily significant change" or "adaptive evolutionary change" refers to one or more nucleotide or peptide sequence change(s) between two species that may be attributed to a positive selective pressure. One method for determining the presence of an evolutionarily significant change is to apply a $K_A/K_S$-type analytical method, such as to measure a $K_A/K_S$ ratio. Typically, a $K_A/K_S$ ratio at least about 0.75, more preferably at least about 1.0, more preferably at least about 1.25, more preferably at least about 1.5 and most preferably at least about 2.0 indicates the action of positive selection and is considered to be an evolutionarily significant change.

Strictly speaking, only $K_A/K_S$ ratios greater than 1.0 are indicative of positive selection. It is commonly accepted that the ESTs in GenBank® and other public databases often suffer from some degree of sequencing error, and even a few incorrect nucleotides can influence $K_A/K_S$ scores. Thus, all pairwise comparisons that involve public ESTs must be undertaken with care. Due to the errors inherent in the publicly available databases, it is possible that these errors could depress a $K_A/K_S$ ratio below 1.0. For this reason, $K_A/K_S$ ratios between 0.75 and 1.0 should be examined carefully in order to determine whether or not a sequencing error has obscured evidence of positive selection. Such errors may be discovered through sequencing methods that are designed to be highly accurate.

The term "positive evolutionarily significant change" means an evolutionarily significant change in a particular species that results in an adaptive change that is positive as compared to other related species. Examples of positive evolutionarily significant changes are changes that have resulted in enhanced cognitive abilities or enhanced or unique physiological conditions in humans and adaptive changes in chimpanzees that have resulted in the ability of the chimpanzees infected with HIV or HCV to be resistant to progression of the infection.

The term "enhanced breast development" refers to the enlarged breasts observed in humans relative to non-human primates. The enlarged human breast has increased adipose, duct and/or gland tissue relative to other primates, and develops prior to first pregnancy and lactation.

The term "resistant" means that an organism, such as a chimpanzee, exhibits an ability to avoid, or diminish the extent of, a disease condition and/or development of the disease, preferably when compared to non-resistant organisms, typically humans. For example, a chimpanzee is resistant to certain impacts of HCV, HIV and other viral infections, and/or it does not develop the ultimate disease (chronic hepatitis or AIDS, respectively).

The term "susceptibility" means that an organism, such as a human, fails to avoid, or diminish the extent of, a disease condition and/or development of the disease condition, preferably when compared to an organism that is known to be resistant, such as a non-human primate, such as chimpanzee. For example, a human is susceptible to certain impacts of HCV, HIV and other viral infections and/or development of the ultimate disease (chronic hepatitis or AIDS).

It is understood that resistance and susceptibility vary from individual to individual, and that, for purposes of this invention, these terms also apply to a group of individuals within a species, and comparisons of resistance and susceptibility generally refer to overall, average differences between species, although intra-specific comparisons may be used.

The term "homologous" or "homologue" or "ortholog" is known and well understood in the art and refers to related sequences that share a common ancestor and is determined based on degree of sequence identity. These terms describe the relationship between a gene found in one species and the corresponding or equivalent gene in another species. For purposes of this invention homologous sequences are compared. "Homologous sequences" or "homologues" or "orthologs" are thought, believed, or known to be functionally related. A functional relationship may be indicated in any one of a number of ways, including, but not limited to, (a) degree of sequence identity; (b) same or similar biological function. Preferably, both (a) and (b) are indicated. The degree of sequence identity may vary, but is preferably at least 50% (when using standard sequence alignment programs known in the art), more preferably at least 60%, more preferably at least about 75%, more preferably at least about 85%. Homology can be determined using software programs readily available in the art, such as those discussed in *Current Protocols in Molecular Biology* (F. M. Ausubel et al., eds., 1987) Supplement 30, section 7.718, Table 7.71. Preferred alignment programs are MacVector (Oxford Molecular Ltd, Oxford, U.K.) and ALIGN Plus (Scientific and Educational Software, Pa.). Another preferred alignment program is Sequencher (Gene Codes, Ann Arbor, Mich.), using default parameters.

The term "nucleotide change" refers to nucleotide substitution, deletion, and/or insertion, as is well understood in the art.

The term "human protein-coding nucleotide sequence" which is "associated with susceptibility to AIDS" as used herein refers to a human nucleotide sequence that encodes a protein that is associated with HIV dissemination (within the organism, i.e., intra-organism infectivity), propagation and/or development of AIDS. Due to the extensive research in the mechanisms underlying progression from HIV infection to the development of AIDS, a number of candidate human genes are believed or known to be associated with one or more of these phenomena. A polynucleotide (including any polypeptide encoded therein) sequence associated with susceptibility to AIDS is one which is either known or implicated to play a role in HIV dissemination, replication, and/or subsequent progression to full-blown AIDS. Examples of such candidate genes are provided below.

"AIDS resistant" means that an organism, such as a chimpanzee, exhibits an ability to avoid, or diminish the extent of, the result of HIV infection (such as propagation and dissemination) and/or development of AIDS, preferably when compared to AIDS-susceptible humans.

"Susceptibility" to AIDS means that an organism, such as a human, fails to avoid, or diminish the extent of; the result of HIV infection (such as propagation and dissemination) and/or development of AIDS, preferably when compared to an organism that is known to be AIDS resistant, such as a non-human primate, such as chimpanzee.

The term "human protein-coding nucleotide sequence" which is "associated with susceptibility to HCV infection" as used herein refers to a human nucleotide sequence that encodes a polypeptide that is associated with HCV dissemination (within the organism, i.e., intra-organism infectivity), propagation and/or development of chronic hepatitis. Candidate human genes are believed or known to be associated with human susceptibility to HCV infection. A polynucleotide (including any polypeptide encoded therein) sequence associated with susceptibility to chronic hepatitis is one which is either known or implicated to play a role in HCV dissemination, replication, and/or subsequent progression to chronic hepatitis or hepatocellular carcinoma. One example of a polynucleotide associated with susceptibility is human p44 exon 2.

"HCV resistant" means that an organism, such as a chimpanzee, exhibits an ability to avoid, or diminish the extent of, the result of HCV infection (such as propagation and dissemination) and/or development of chronic hepatitis, preferably when compared to HCV-susceptible humans.

"Susceptibility" to HCV infection means that an organism, such as a human, fails to avoid, or diminish the extent of, the result of HCV infection (such as propagation and dissemination) and/or development of chronic hepatitis, preferably when compared to an organism that is known to be HCV infection resistant, such as a non-human primate, such as chimpanzee.

The term "brain protein-coding nucleotide sequence" as used herein refers to a nucleotide sequence expressed in the brain that encodes a protein. One example of the "brain protein-coding nucleotide sequence" is a brain cDNA sequence.

As used herein, the term "brain functions unique or enhanced in humans" or "unique functional capabilities of the human brain" or "brain functional capability that is unique or enhanced in humans" refers to any brain function, either in kind or in degree, that is identified and/or observed to be enhanced in humans compared to other non-human primates. Such brain functions include, but are not limited to high capacity information processing, storage and retrieval capabilities, creativity, memory, language abilities, brain-mediated emotional response, locomotion, pain/pleasure sensation, olfaction, and temperament.

"Housekeeping genes" is a term well understood in the art and means those genes associated with general cell function, including but not limited to growth, division, stasis, metabolism, and/or death. "Housekeeping" genes generally perform functions found in more than one cell type. In contrast, cell-specific genes generally perform functions in a particular cell type (such as neurons) and/or class (such as neural cells).

The term "agent", as used herein, means a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic and inorganic compounds based on various core structures, and these are also included in the term "agent". In addition, various natural sources can provide compounds for screening, such as plant or animal extracts, and the like. Compounds can be tested singly or in combination with one another.

The term "to modulate function" of a polynucleotide or a polypeptide means that the function of the polynucleotide or polypeptide is altered when compared to not adding an agent. Modulation may occur on any level that affects function. A polynucleotide or polypeptide function may be direct or indirect, and measured directly or indirectly.

A "function of a polynucleotide" includes, but is not limited to, replication; translation; and expression pattern(s). A polynucleotide function also includes functions associated with a polypeptide encoded within the polynucleotide. For example, an agent which acts on a polynucleotide and affects protein expression, conformation, folding (or other physical characteristics), binding to other moieties (such as ligands), activity (or other functional characteristics), regulation and/or other aspects of protein structure or function is considered to have modulated polynucleotide function.

A "function of a polypeptide" includes, but is not limited to, conformation, folding (or other physical characteristics), binding to other moieties (such as ligands), activity (or other functional characteristics), and/or other aspects of protein structure or functions. For example, an agent that acts on a polypeptide and affects its conformation, folding (or other physical characteristics), binding to other moieties (such as ligands), activity (or other functional characteristics), and/or other aspects of protein structure or functions is considered to have modulated polypeptide function. The ways that an effective agent can act to modulate the function of a polypeptide include, but are not limited to 1) changing the conformation, folding or other physical characteristics; 2) changing the binding strength to its natural ligand or changing the specificity of binding to ligands; and 3) altering the activity of the polypeptide.

The terms "modulate susceptibility to development of AIDS" and "modulate resistance to development of AIDS", as used herein, include modulating intra-organism cell-to-cell transmission or infectivity of HIV. The terms further include reducing susceptibility to development of AIDS and/or cell-to-cell transmission or infectivity of HIV. The terms further include increasing resistance to development of AIDS and/or cell-to-cell transmission or infectivity of HIV. One means of assessing whether an agent is one that modulates susceptibility or resistance to development of AIDS is to determine whether at least one index of HIV susceptibility is affected, using a cell-based system as described herein, as compared with an appropriate control. Indicia of HIV susceptibility include, but are not limited to, cell-to-cell transmission of the virus, as measured by total number of cells infected with HIV and syncytia formation.

The terms "modulate susceptibility to HCV infection" and "modulate resistance to HCV infection", as used herein, include modulating intra-organism cell-to-cell transmission or infectivity of HCV. The terms further include reducing susceptibility to development of chronic hepatitis and/or cell-to-cell transmission or infectivity of HCV. The terms further include increasing resistance to infection by HCV and/or cell-to-cell transmission or infectivity of HCV. One means of assessing whether an agent is one that modulates susceptibility or resistance to development of HCV-associated chronic hepatitis is to determine whether at least one index of HCV susceptibility is affected, using a cell-based system as described herein, as compared with an appropriate control. Indicia of HCV susceptibility include, but are not limited to, cell-to-cell transmission of the virus, as measured by total number of cells infected with HCV.

The term "target site" means a location in a polypeptide which can be one or more amino acids and/or is a part of a structural and/or functional motif, e.g., a binding site, a dimerization domain, or a catalytic active site. It also includes a location in a polynucleotide where there is one or more non-synonymous nucleotide changes in a protein coding region, or may also refer to a regulatory region of a positively selected gene. Target sites may be a useful for direct or indirect interaction with an agent, such as a therapeutic agent.

The term "molecular difference" includes any structural and/or functional difference. Methods to detect such differences, as well as examples of such differences, are described herein.

A "functional effect" is a term well known in the art, and means any effect which is exhibited on any level of activity, whether direct or indirect.

An agent that interacts with human p44 polypeptide to form a complex that "mimics the structure" of chimpanzee or other non-human primate p44 polypeptide means that the interaction of the agent with the human p44 polypeptide results in a complex whose three-dimensional structure more closely approximates the three-dimensional structure of the chimpanzee or non-human p44 polypeptide, relative to the human p44 polypeptide alone.

An agent that interacts with human p44 polypeptide to form a complex that "mimics the function" of chimpanzee or other non-human primate p44 polypeptide means that the complex of human p44 polypeptide and agent attain a biological function or enhance a biological function that is characteristic of the chimpanzee or other non-human primate p44 polypeptide, relative to the human p44 polypeptide alone. Such biological function of chimpanzee p44 polypeptide includes, without limitation, microtubule assembly following HCV infection, and resistance to HCV infection of hepatocytes.

General Procedures Known in the Art

For the purposes of this invention, the source of the human and non-human polynucleotide can be any suitable source, e.g., genomic sequences or cDNA sequences. Preferably, cDNA sequences from human and a non-human primate are compared. Human protein-coding sequences can be obtained from public databases such as the Genome Sequence Data Bank and GenBank. These databases serve as repositories of the molecular sequence data generated by ongoing research efforts. Alternatively, human protein-coding sequences may be obtained from, for example, sequencing of cDNA reverse transcribed from mRNA expressed in human cells, or after PCR amplification, according to methods well known in the art. Alternatively, human genomic sequences may be used for sequence comparison. Human genomic sequences can be obtained from public databases or from a sequencing of commercially available human genomic DNA libraries or from genomic DNA, after PCR.

The non-human primate protein-coding sequences can be obtained by, for example, sequencing cDNA clones that are randomly selected from a non-human primate cDNA library. The non-human primate cDNA library can be constructed from total mRNA expressed in a primate cell using standard techniques in the art. In some embodiments, the cDNA is prepared from mRNA obtained from a tissue at a determined developmental stage, or a tissue obtained after the primate has been subjected to certain environmental conditions. cDNA libraries used for the sequence comparison of the present invention can be constructed using conventional cDNA library construction techniques that are explained fully in the literature of the art. Total mRNAs are used as templates to reverse-transcribe cDNAs. Transcribed cDNAs are subcloned into appropriate vectors to establish a cDNA library. The established cDNA library can be maximized for full-length cDNA contents, although less than full-length cDNAs may be used. Furthermore, the sequence frequency can be normalized according to, for example, Bonaldo et al. (1996) *Genone Research* 6:791-806. cDNA clones randomly selected from the constructed cDNA library can be sequenced using standard automated sequencing techniques. Preferably, full-length cDNA clones are used for sequencing. Either the entire or a large portion of cDNA clones from a cDNA library may be sequenced, although it is also possible to practice some embodiments of the invention by sequencing as little as a single cDNA, or several cDNA clones.

In one preferred embodiment of the present invention, non-human primate cDNA clones to be sequenced can be pre-selected according to their expression specificity. In order to select cDNAs corresponding to active genes that are specifically expressed, the cDNAs can be subject to subtraction hybridization using mRNAs obtained from other organs, tissues or cells of the same animal. Under certain hybridization conditions with appropriate stringency and concentration, those cDNAs that hybridize with non-tissue specific mRNAs and thus likely represent "housekeeping" genes will be excluded from the cDNA pool. Accordingly, remaining cDNAs to be sequenced are more likely to be associated with tissue-specific functions. For the purpose of subtraction hybridization, non-tissue-specific mRNAs can be obtained from one organ, or preferably from a combination of different organs and cells. The amount of non-tissue-specific mRNAs are maximized to saturate the tissue-specific cDNAs.

Alternatively, information from online public databases can be used to select or give priority to cDNAs that are more likely to be associated with specific functions. For example, the non-human primate cDNA candidates for sequencing can be selected by PCR using primers designed from candidate human cDNA sequence. Candidate human cDNA sequences are, for example, those that are only found in a specific tissue, such as brain or breast, or that correspond to genes likely to be important in the specific function, such as brain function or breast tissue adipose or glandular development. Such human tissue-specific cDNA sequences can be obtained by searching online human sequence databases such as GenBank, in which information with respect to the expression profile and/or biological activity for cDNA sequences are specified.

Sequences of non-human primate (for example, from an AIDS- or HCV-resistant non-human primate) homologue(s) to a known human gene may be obtained using methods standard in the art, such as from public databases such as GenBank or PCR methods (using, for example, GeneAmp PCR System 9700 thermocyclers (Applied Biosystems, Inc.)). For example non-human primate cDNA candidates for sequencing can be selected by PCR using primers designed from candidate human cDNA sequences.

For PCR, primers may be made from the human sequences using standard methods in the art, including publicly available primer design programs such as PRIMER7 (Whitehead Institute). The sequence amplified may then be sequenced using standard methods and equipment in the art, such as automated sequencers (Applied Biosystems, Inc.).

General Methods of the Invention

The general method of the invention is as follows. Briefly, nucleotide sequences are obtained from a human source and a non-human source. The human and non-human nucleotide sequences are compared to one another to identify sequences that are homologous. The homologous sequences are analyzed to identify those that have nucleic acid sequence differences between the two species. Then molecular evolution analysis is conducted to evaluate quantitatively and qualitatively the evolutionary significance of the differences. For genes that have been positively selected between two species, e.g., human and chimp, it is useful to determine whether the difference occurs in other non-human primates. Next, the sequence is characterized in terms of molecular/genetic identity and biological function. Finally, the information can be used to identify agents useful in diagnosis and treatment of human medically or commercially relevant conditions.

The general methods of the invention entail comparing human protein-coding nucleotide sequences to protein-coding nucleotide sequences of a non-human, preferably a primate, and most preferably a chimpanzee. Examples of other non-human primates are bonobo, gorilla, orangutan, gibbon. Old World monkeys, and New World monkeys. A phylogenetic tree for primates within the hominoid group is depicted in FIG. 1. Bioinformatics is applied to the comparison and sequences are selected that contain a nucleotide change or changes that is/are evolutionarily significant change(s). The invention enables the identification of genes that have evolved to confer some evolutionary advantage and the identification of the specific evolved changes.

Protein-coding sequences of human and another non-human primate are compared to identify homologous sequences. Protein-coding sequences known to or suspected of having a specific biological function may serve as the starting point for the comparison. Any appropriate mechanism for completing this comparison is contemplated by this invention. Alignment may be performed manually or by software (examples of suitable alignment programs are known in the art). Preferably, protein-coding sequences from a non-human primate are compared to human sequences via database searches, e.g., BLAST searches. The high scoring "hits," i.e., sequences that show a significant similarity after BLAST analysis, will be retrieved and analyzed. Sequences showing a significant similarity can be those having at least about 60%, at least about 75%, at least about 80%, at least about 85%, or at least about 90% sequence identity. Preferably, sequences showing greater than about 80% identity are further analyzed. The homologous sequences identified via database searching can be aligned in their entirety using sequence alignment methods and programs that are known and available in the art, such as the commonly used simple alignment program CLUSTAL V by Higgins et al. (1992) *CABIOS* 8:189-191.

Alternatively, the sequencing and homologous comparison of protein-coding sequences between human and a non-human primate may be performed simultaneously by using the newly developed sequencing chip technology. See, for example, Rava et al. U.S. Pat. No. 5,545,531.

The aligned protein-coding sequences of human and another non-human primate are analyzed to identify nucleotide sequence differences at particular sites. Again, any suitable method for achieving this analysis is contemplated by this invention. If there are no nucleotide sequence differences, the non-human primate protein coding sequence is not usually further analyzed. The detected sequence changes are generally, and preferably, initially checked for accuracy. Preferably, the initial checking comprises performing one or more of the following steps, any and all of which are known in the art: (a) finding the points where there are changes between the non-human primate and human sequences; (b) checking the sequence fluorogram (chromatogram) to determine if the bases that appear unique to non-human primate correspond to strong, clear signals specific for the called base; (c) checking the human hits to see if there is more than one human sequence that corresponds to a sequence change. Multiple human sequence entries for the same gene that have the same nucleotide at a position where there is a different nucleotide in a non-human primate sequence provides independent support that the human sequence is accurate, and that the change is significant. Such changes are examined using public database information and the genetic code to determine whether these nucleotide sequence changes result in a change in the amino acid sequence of the encoded protein. As the definition of "nucleotide change" makes clear, the present invention encompasses at least one nucleotide change, either a substitution, a deletion or an insertion, in a human protein-coding polynucleotide sequence as compared to corresponding sequence from a non-human primate. Preferably, the change is a nucleotide substitution. More preferably, more than one substitution is present in the identified human sequence and is subjected to molecular evolution analysis.

Any of several different molecular evolution analyses or $K_A/K_S$-type methods can be employed to evaluate quantitatively and qualitatively the evolutionary significance of the identified nucleotide changes between human gene sequences and that of a non-human primate. Kreitman and Akashi (1995) *Annu. Rev. Ecol. Syst.* 26:403-422; Li, *Molecular Evolution*, Sinauer Associates, Sunderland, Mass., 1997. For example, positive selection on proteins (i.e., molecular-level adaptive evolution) can be detected in protein-coding genes by pairwise comparisons of the ratios of nonsynonymous nucleotide substitutions per nonsynonymous site ($K_A$) to synonymous substitutions per synonymous site ($K_S$) (Li et al., 1985; Li, 1993). Any comparison of $K_A$ and $K_S$ may be used, although it is particularly convenient and most effective to compare these two variables as a ratio. Sequences are identified by exhibiting a statistically significant difference between $K_A$ and $K_S$ using standard statistical methods.

Preferably, the $K_A/K_S$ analysis by Li et al. is used to carry out the present invention, although other analysis programs that can detect positively selected genes between species can also be used. Li et al. (1985) *Mol. Biol. Evol.* 2:150-174; Li (1993); see also *J. Mol. Evol.* 36:96-99; Messier and Stewart (1997) *Nature* 385:151-154; Nei (1987) *Molecular Evolutionary Genetics* (New York., Columbia University Press). The $K_A/K_S$ method, which comprises a comparison of the rate of non-synonymous substitutions per non-synonymous site with the rate of synonymous substitutions per synonymous site between homologous protein-coding region of genes in terms of a ratio, is used to identify sequence substitutions that may be driven by adaptive selections as opposed to neutral selections during evolution. A synonymous ("silent") substitution is one that, owing to the degeneracy of the genetic code, makes no change to the amino acid sequence encoded; a non-synonymous substitution results in an amino acid replacement. The extent of each type of change can be estimated as $K_A$ and $K_S$, respectively, the numbers of synonymous substitutions per synonymous site and non-synonymous substitutions per non-synonymous site. Calculations of $K_A/K_S$ may be performed manually or by using software. An example of a suitable program is MEGA (Molecular Genetics Institute, Pennsylvania State University).

For the purpose of estimating $K_A$ and $K_S$, either complete or partial human protein-coding sequences are used to calculate total numbers of synonymous and non-synonymous substitutions, as well as non-synonymous and synonymous sites. The length of the polynucleotide sequence analyzed can be any appropriate length. Preferably, the entire coding sequence is compared, in order to determine any and all significant changes. Publicly available computer programs, such as Li93 (Li (1993) *J. Mol. Evol.* 36:96-99) or INA, can be used to calculate the $K_A$ and $K_S$ values for all pairwise comparisons. This analysis can be further adapted to examine sequences in a "sliding window" fashion such that small numbers of important changes are not masked by the whole sequence. "Sliding window" refers to examination of consecutive, overlapping subsections of the gene (the subsections can be of any length).

The comparison of non-synonymous and synonymous substitution rates is represented by the $K_A/K_s$ ratio. $K_A/K_s$ has been shown to be a reflection of the degree to which adaptive evolution has been at work in the sequence under study. Full length or partial segments of a coding sequence can be used for the $K_A/K_S$ analysis. The higher the $K_A/K_S$ ratio, the more likely that a sequence has undergone adaptive evolution and the non-synonymous substitutions are evolutionarily significant. See, for example, Messier and Stewart (1997). Preferably, the $K_A/K_S$ ratio is at least about 0.75, more preferably at least about 1.0, more preferably at least about 1.25, more preferably at least about 1.50, or more preferably at least about 2.00. Preferably, statistical analysis is performed on all elevated $K_A/K_S$ ratios, including, but not limited to, standard methods such as Student=s t-test and likelihood ratio tests described by Yang (1998) *Mol. Biol Evol.* 37:441-456.

$K_A/K_S$ ratios significantly greater than unity strongly suggest that positive selection has fixed greater numbers of amino acid replacements than can be expected as a result of chance alone, and is in contrast to the commonly observed pattern in which the ratio is less than or equal to one. Nei (1987); Hughes and Hei (1988) *Nature* 335:167-170; Messier and Stewart (1994) *Current Biol.* 4:911-913; Kreitman and Akashi (1995) *Ann. Rev. Ecol. Syst.* 26:403-422; Messier and Stewart (1997). Ratios less than one generally signify the role of negative, or purifying selection: there is strong pressure on the primary structure of functional, effective proteins to remain unchanged.

All methods for calculating $K_A/K_S$ ratios are based on a pairwise comparison of the number of nonsynonymous substitutions per nonsynonymous site to the number of synonymous substitutions per synonymous site for the protein-coding regions of homologous genes from related species. Each method implements different corrections for estimating "multiple hits" (i.e. more than one nucleotide substitution at the same site). Each method also uses different models for how DNA sequences change over evolutionary time. Thus, preferably, a combination of results from different algorithms is used to increase the level of sensitivity for detection of positively-selected genes and confidence in the result.

Preferably, $K_A/K_S$ ratios should be calculated for orthologous gene pairs, as opposed to paralogous gene pairs (i.e. a gene which results from speciation, as opposed to a gene that is the result of gene duplication) Messier and Stewart (1997). This distinction may be made by performing additional comparisons with other non-human primates, such as gorilla and orangutan, which allows for phylogenetic tree-building.

Orthologous genes when used in tree-building will yield the known "species tree", i.e., will produce a tree that recovers the known biological tree. In contrast, paralogous genes will yield trees which will violate the known biological tree.

It is understood that the methods described herein could lead to the identification of human polynucleotide sequences that are functionally related to human protein-coding sequences. Such sequences may include, but are not limited to, non-coding sequences or coding sequences that do not encode human proteins. These related sequences can be, for example, physically adjacent to the human protein-coding sequences in the human genome, such as introns or 5=- and 3=- flanking sequences (including control elements such as promoters and enhancers). These related sequences may be obtained via searching a public human genome database such as GenBank or, alternatively, by screening and sequencing a human genomic library with a protein-coding sequence as probe. Methods and techniques for obtaining non-coding sequences using related coding sequence are well known to one skilled in the art.

The evolutionarily significant nucleotide changes, which are detected by molecular evolution analysis such as the $K_A/K_S$ analysis, can be further assessed for their unique occurrence in humans (or the non-human primate) or the extent to which these changes are unique in humans (or the non-human primate). For example, the identified changes can be tested for presence/absence in other non-human primate sequences. The sequences with at least one evolutionarily significant change between human and one non-human primate can be used as primers for PCR analysis of other non-human primate protein-coding sequences, and resulting polynucleotides are sequenced to see whether the same change is present in other non-human primates. These comparisons allow further discrimination as to whether the adaptive evolutionary changes are unique to the human lineage as compared to other non-human primates or whether the adaptive change is unique to the non-human primates (i.e., chimpanzee) as compared to humans and other non-human primates. A nucleotide change that is detected in human but not other primates more likely represents a human adaptive evolutionary change. Alternatively, a nucleotide change that is detected in a non-human primate (i.e., chimpanzee) that is not detected in humans or other non-human primates likely represents a chimpanzee adaptive evolutionary change. Other non-human primates used for comparison can be selected based on their phylogenetic relationships with human. Closely related primates can be those within the hominoid sublineage, such as chimpanzee, bonobo, gorilla, and orangutan. Non-human primates can also be those that are outside the hominoid group and thus not so closely related to human, such as the Old World monkeys and New World monkeys. Statistical significance of such comparisons may be determined using established available programs, e.g., t-test as used by Messier and Stewart (1997) *Nature* 385:151-154. Those genes showing statistically high $K_A/K_S$ ratios are very likely to have undergone adaptive evolution.

Sequences with significant changes can be used as probes in genomes from different human populations to see whether the sequence changes are shared by more than one human population. Gene sequences from different human populations can be obtained from databases made available by, for example, the Human Genome Project, the human genome diversity project or, alternatively, from direct sequencing of PCR-amplified DNA from a number of unrelated, diverse human populations. The presence of the identified changes in different human populations would further indicate the evolutionary significance of the changes. Chimpanzee sequences with significant changes can be obtained and evaluated using similar methods to determine whether the sequence changes are shared among many chimpanzees.

Sequences with significant changes between species can be further characterized in terms of their molecular/genetic identities and biological functions, using methods and techniques known to those of ordinary skill in the art. For example, the sequences can be located genetically and physically within the human genome using publicly available bio-informatics programs. The newly identified significant changes within the nucleotide sequence may suggest a potential role of the gene in human evolution and a potential association with human-unique functional capabilities. The putative gene with the identified sequences may be further characterized by, for example, homologue searching. Shared homology of the putative gene with a known gene may indicate a similar biological role or function. Another exemplary method of characterizing a putative gene sequence is on the basis of known sequence motifs. Certain sequence patterns are known to code for regions of proteins having specific biological characteristics such as signal sequences, DNA binding domains, or transmembrane domains.

The identified human sequences with significant changes can also be further evaluated by looking at where the gene is expressed in terms of tissue- or cell type-specificity. For example, the identified coding sequences can be used as probes to perform in situ mRNA hybridization that will reveal the expression patterns of the sequences. Genes that are expressed in certain tissues may be better candidates as being associated with important human functions associated with that tissue, for example brain tissue. The timing of the gene expression during each stage of human development can also be determined.

As another exemplary method of sequence characterization, the functional roles of the identified nucleotide sequences with significant changes can be assessed by conducting functional assays for different alleles of an identified gene in a model system, such as yeast, nematode, *Drosophila*, and mouse. Model systems may be cell-based or in vivo, such as transgenic animals or animals with chimeric organs or tissues. Preferably, the transgenic mouse or chimeric organ mouse system is used. Methods of making cell-based systems and/or transgenic/chimeric animal systems are known in the art and need not be described in detail herein.

As another exemplary method of sequence characterization, the use of computer programs allows modeling and visualizing the three-dimensional structure of the homologous proteins from human and chimpanzee. Specific, exact knowledge of which amino acids have been replaced in a primate's protein(s) allows detection of structural changes that may be associated with functional differences. Thus, use of modeling techniques is closely associated with identification of functional roles discussed in the previous paragraph. The use of individual or combinations of these techniques constitutes part of the present invention. For example, chimpanzee ICAM-3 contains a glutamine residue (Q101) at the site in which human ICAM-3 contains a proline (P101). The human protein is known to bend sharply at this point. Replacement of the proline by glutamine in the chimpanzee protein is likely to result in a much less sharp bend at this point. This has clear implications for packaging of the ICAM-3 chimpanzee protein into HIV virions.

Likewise, chimpanzee p44 has been found to contain an exon (exon2) having several evolutionarily significant nucleotide changes relative to human p44 exon 2. The nonsynonymous changes and corresponding amino acid changes in chimpanzee p44 polypeptide are believed to confer HCV resistance to the chimpanzee. The mechanism may involve enhanced p44 microtubule assembly in hepatocytes.

The sequences identified by the methods described herein have significant uses in diagnosis and treatment of medically or commercially relevant human conditions. Accordingly, the present invention provides methods for identifying agents that are useful in modulating human-unique or human-enhanced functional capabilities and/or correcting defects in these capabilities using these sequences. These methods employ, for example, screening techniques known in the art, such as in vivo systems, cell-based expression systems and transgenic/chimeric animal systems. The approach provided by the present invention not only identifies rapidly evolved genes, but indicates modulations that can be made to the protein that may not be too toxic because they exist in another species.

Screening Methods

The present invention also provides screening methods using the polynucleotides and polypeptides identified and characterized using the above-described methods. These screening methods are useful for identifying agents which may modulate the function(s) of the polynucleotides or polypeptides in a manner that would be useful for a human treatment. Generally, the methods entail contacting at least one agent to be tested with either a cell that has been transfected with a polynucleotide sequence identified by the methods described above, or a preparation of the polypeptide encoded by such polynucleotide sequence, wherein an agent is identified by its ability to modulate function of either the polynucleotide sequence or the polypeptide.

As used herein, the term "agent" means a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic and inorganic compounds based on various core structures, and these are also included in the term "agent". In addition, various natural sources can provide compounds for screening, such as plant or animal extracts, and the like. Compounds can be tested singly or in combination with one another.

To "modulate function" of a polynucleotide or a polypeptide means that the function of the polynucleotide or polypeptide is altered when compared to not adding an agent. Modulation may occur on any level that affects function. A polynucleotide or polypeptide function may be direct or indirect, and measured directly or indirectly. A "function" of a polynucleotide includes, but is not limited to, replication, translation, and expression pattern(s). A polynucleotide function also includes functions associated with a polypeptide encoded within the polynucleotide. For example, an agent which acts on a polynucleotide and affects protein expression, conformation, folding (or other physical characteristics), binding to other moieties (such as ligands), activity (or other functional characteristics), regulation and/or other aspects of protein structure or function is considered to have modulated polynucleotide function. The ways that an effective agent can act to modulate the expression of a polynucleotide include, but are not limited to 1) modifying binding of a transcription factor to a transcription factor responsive element in the polynucleotide; 2) modifying the interaction between two transcription factors necessary for expression of the polynucleotide; 3) altering the ability of a transcription factor necessary for expression of the polynucleotide to enter the nucleus; 4) inhibiting the activation of a transcription factor involved in transcription of the polynucleotide; 5) modifying a cell-surface receptor which normally interacts with a ligand and whose binding of the ligand results in expression of the polynucleotide; 6) inhibiting the inactivation of a component of the signal transduction cascade that leads to expression of the polynucleotide; and 7) enhancing the activation of a transcription factor involved in transcription of the polynucleotide.

A "function" of a polypeptide includes, but is not limited to, conformation, folding (or other physical characteristics), binding to other moieties (such as ligands), activity (or other functional characteristics), and/or other aspects of protein structure or functions. For example, an agent that acts on a polypeptide and affects its conformation, folding (or other physical characteristics), binding to other moieties (such as ligands), activity (or other functional characteristics), and/or other aspects of protein structure or functions is considered to have modulated polypeptide function. The ways that an effective agent can act to modulate the function of a polypeptide include, but are not limited to 1) changing the conformation, folding or other physical characteristics; 2) changing the binding strength to its natural ligand or changing the specificity of binding to ligands; and 3) altering the activity of the polypeptide.

A "function" of a polynucleotide includes its expression, i.e., transcription and/or translation. It can also include (without limitation) its conformation, folding and binding to other moieties.

Generally, the choice of agents to be screened is governed by several parameters, such as the particular polynucleotide or polypeptide target, its perceived function, its three-dimensional structure (if known or surmised), and other aspects of rational drug design. Techniques of combinatorial chemistry can also be used to generate numerous permutations of candidates. Those of skill in the art can devise and/or obtain suitable agents for testing.

The in vivo screening assays described herein may have several advantages over conventional drug screening assays: 1) if an agent must enter a cell to achieve a desired therapeutic effect, an in vivo assay can give an indication as to whether the agent can enter a cell; 2) an in vivo screening assay can identify agents that, in the state in which they are added to the assay system are ineffective to elicit at least one characteristic which is associated with modulation of polynucleotide or polypeptide function, but that are modified by cellular components once inside a cell in such a way that they become effective agents; 3) most importantly, an in vivo assay system allows identification of agents affecting any component of a pathway that ultimately results in characteristics that are associated with polynucleotide or polypeptide function.

In general, screening can be performed by adding an agent to a sample of appropriate cells which have been transfected with a polynucleotide identified using the methods of the present invention, and monitoring the effect, i.e., modulation of a function of the polynucleotide or the polypeptide encoded within the polynucleotide. The experiment preferably includes a control sample which does not receive the candidate agent. The treated and untreated cells are then compared by any suitable phenotypic criteria, including but not limited to microscopic analysis, viability testing, ability to replicate, histological examination, the level of a particular RNA or polypeptide associated with the cells, the level of enzymatic activity expressed by the cells or cell lysates, the interactions of the cells when exposed to infectious agents, such as HIV, and the ability of the cells to interact with other cells or compounds. For example, the transfected cells can be exposed to the agent to be tested and, before, during, or after treatment with the agent, the cells can be infected with a virus, such as HCV or HIV, and tested for any indication of susceptibility of the cells to viral infection, including, for example, susceptibility of the cells to cell-to-cell viral infection, replication of the virus, production of a viral protein, and/or syncytia formation following infection with the virus. Differences between treated and untreated cells indicate effects attributable to the candidate agent. Optimally, the agent has a greater effect on experimental cells than on control cells. Appropriate host cells include, but are not limited to, eukaryotic cells, preferably mammalian cells. The choice of cell will at least partially depend on the nature of the assay contemplated.

To test for agents that upregulate the expression of a polynucleotide, a suitable host cell transfected with a polynucleotide of interest, such that the polynucleotide is expressed (as used herein, expression includes transcription and/or translation) is contacted with an agent to be tested. An agent would be tested for its ability to result in increased expression of mRNA and/or polypeptide. Methods of making vectors and transfection are well known in the art. "Transfection" encompasses any method of introducing the exogenous sequence, including, for example, lipofection, transduction, infection or electroporation. The exogenous polynucleotide may be maintained as a non-integrated vector (such as a plasmid) or may be integrated into the host genome.

To identify agents that specifically activate transcription, transcription regulatory regions could be linked to a reporter gene and the construct added to an appropriate host cell. As used herein, the term "reporter gene" means a gene that encodes a gene product that can be identified (i.e., a reporter protein). Reporter genes include, but are not limited to, alkaline phosphatase, chloramphenicol acetyltransferase, $\beta$-galactosidase, luciferase and green fluorescence protein (GFP). Identification methods for the products of reporter genes include, but are not limited to, enzymatic assays and fluorimetric assays. Reporter genes and assays to detect their products are well known in the art and are described, for example in Ausubel et al. (1987) and periodic updates. Reporter genes, reporter gene assays, and reagent kits are also readily available from commercial sources. Examples of appropriate cells include, but are not limited to, fungal, yeast, mammalian, and other eukaryotic cells. A practitioner of ordinary skill will be well acquainted with techniques for transfecting eukaryotic cells, including the preparation of a suitable vector, such as a viral vector; conveying the vector into the cell, such as by electroporation; and selecting cells that have been transformed, such as by using a reporter or drug sensitivity element. The effect of an agent on transcription from the regulatory region in these constructs would be assessed through the activity of the reporter gene product.

Besides the increase in expression under conditions in which it is normally repressed mentioned above, expression could be decreased when it would normally be maintained or increased. An agent could accomplish this through a decrease in transcription rate and the reporter gene system described above would be a means to assay for this. The host cells to assess such agents would need to be permissive for expression.

Cells transcribing mRNA (from the polynucleotide of interest) could be used to identify agents that specifically modulate the half-life of mRNA and/or the translation of mRNA. Such cells would also be used to assess the effect of an agent on the processing and/or post-translational modification of the polypeptide. An agent could modulate the amount of polypeptide in a cell by modifying the turnover (i.e., increase or decrease the half-life) of the polypeptide. The specificity of the agent with regard to the mRNA and polypeptide would be determined by examining the products in the absence of the agent and by examining the products of unrelated mRNAs and polypeptides. Methods to examine mRNA half-life, protein processing, and protein turn-over are well know to those skilled in the art.

In vivo screening methods could also be useful in the identification of agents that modulate polypeptide function through the interaction with the polypeptide directly. Such agents could block normal polypeptide-ligand interactions, if any, or could enhance or stabilize such interactions. Such agents could also alter a conformation of the polypeptide. The effect of the agent could be determined using immunoprecipitation reactions. Appropriate antibodies would be used to precipitate the polypeptide and any protein tightly associated with it. By comparing the polypeptides immunoprecipitated from treated cells and from untreated cells, an agent could be identified that would augment or inhibit polypeptide-ligand interactions, if any. Polypeptide-ligand interactions could also be assessed using cross-linking reagents that convert a close, but noncovalent interaction between polypeptides into a covalent interaction. Techniques to examine protein-protein interactions are well known to those skilled in the art. Techniques to assess protein conformation are also well known to those skilled in the art.

It is also understood that screening methods can involve in vivo methods, such as cell-free transcription or translation systems. In those systems, transcription or translation is allowed to occur, and an agent is tested for its ability to modulate function. For an assay that determines whether an agent modulates the translation of mRNA or a polynucleotide, an in vitro transcription/translation system may be used. These systems are available commercially and provide an in vitro means to produce mRNA corresponding to a polynucleotide sequence of interest. After mRNA is made, it can be translated in vitro and the translation products compared. Comparison of translation products between an in vitro expression system that does not contain any agent (negative control) with an in vitro expression system that does contain an agent indicates whether the agent is affecting translation. Comparison of translation products between control and test polynucleotides indicates whether the agent, if acting on this level, is selectively affecting translation (as opposed to affecting translation in a general, non-selective or non-specific fashion). The modulation of polypeptide function can be accomplished in many ways including, but not limited to, the in vivo and in vitro assays listed above as well as in in vitro assays using protein preparations. Polypeptides can be extracted and/or purified from natural or recombinant sources to create protein preparations. An agent can be added to a sample of a protein preparation and the effect monitored; that is whether and how the agent acts on a polypeptide and affects its conformation, folding (or other physical characteristics), binding to other moieties (such as ligands), activity (or other functional characteristics), and/or other aspects of protein structure or functions is considered to have modulated polypeptide function.

In an example for an assay for an agent that binds to a polypeptide encoded by a polynucleotide identified by the methods described herein, a polypeptide is first recombinantly expressed in a prokaryotic or eukaryotic expression system as a native or as a fusion protein in which a polypeptide (encoded by a polynucleotide identified as described above) is conjugated with a well-characterized epitope or protein. Recombinant polypeptide is then purified by, for instance, immunoprecipitation using appropriate antibodies or anti-epitope antibodies or by binding to immobilized ligand of the conjugate. An affinity column made of polypeptide or fusion protein is then used to screen a mixture of compounds which have been appropriately labeled. Suitable labels include, but are not limited to fluorochromes, radioisotopes, enzymes and chemiluminescent compounds. The unbound and bound compounds can be separated by washes using various conditions (e.g. high salt, detergent ) that are routinely employed by those skilled in the art. Non-specific binding to the affinity column can be minimized by pre-clearing the compound mixture using an affinity column containing merely the conjugate or the epitope. Similar methods can be used for screening for an agent(s) that competes for binding to polypeptides. In addition to affinity chromatography, there are other techniques such as measuring the change of melting temperature or the fluorescence anisotropy of a protein which will change upon binding another molecule. For example, a BIAcore assay using a sensor chip (supplied by Pharmacia Biosensor, Stitt et al. (1995) *Cell* 80: 661-670) that is covalently coupled to polypeptide may be performed to determine the binding activity of different agents.

It is also understood that the in vitro screening methods of this invention include structural, or rational, drug design, in which the amino acid sequence, three-dimensional atomic structure or other property (or properties) of a polypeptide provides a basis for designing an agent which is expected to bind to a polypeptide. Generally, the design and/or choice of agents in this context is governed by several parameters, such as side-by-side comparison of the structures of a human and homologous non-human primate polypeptides, the perceived function of the polypeptide target, its three-dimensional structure (if known or surmised), and other aspects of rational drug design. Techniques of combinatorial chemistry can also be used to generate numerous permutations of candidate agents.

Also contemplated in screening methods of the invention are transgenic animal systems and animal models containing chimeric organs or tissues, which are known in the art.

The screening methods described above represent primary screens, designed to detect any agent that may exhibit activity that modulates the function of a polynucleotide or polypeptide. The skilled artisan will recognize that secondary tests will likely be necessary in order to evaluate an agent further. For example, a secondary screen may comprise testing the agent(s) in an infectivity assay using mice and other animal models (such as rat), which are known in the art. In addition, a cytotoxicity assay would be performed as a further corroboration that an agent which tested positive in a primary screen would be suitable for use in living organisms. Any assay for cytotoxicity would be suitable for this purpose, including, for example the MTT assay (Promega).

The invention also includes agents identified by the screening methods described herein.

Methods Useful for Identifying Positively Selected Non-Human Traits

In one aspect of the invention, a non-human primate polynucleotide or polypeptide has undergone natural selection that resulted in a positive evolutionarily significant change (i.e., the non-human primate polynucleotide or polypeptide has a positive attribute not present in humans). In this aspect of the invention, the positively selected polynucleotide or polypeptide may be associated with susceptibility or resistance to certain diseases or with other commercially relevant traits. Examples of this embodiment include, but are not limited to, polynucleotides and polypeptides that have been positively selected in non-human primates, preferably chimpanzees, that may be associated with susceptibility or resistance to infectious diseases, cancer, or acne or may be associated with aesthetic conditions of interest to humans, such as hair growth or muscle mass. An example of this embodiment includes polynucleotides and polypeptides associated with the susceptibility or resistance to HIV progression to AIDS. The present invention can thus be useful in gaining insight into the molecular mechanisms that underlie resistance to HIV infection progressing to development of AIDS, providing information that can also be useful in discovering and/or designing agents such as drugs that prevent and/or delay development of AIDS. For example, CD59, which has been identified as a leukocyte and erythrocyte protein whose function is to protect these cells from the complement arm of the body=s MAC (membrane attack complex) defense system (Meri et al. (1996) *Biochem. J.* 616:923-935), has been found to be positively selected in the chimpanzee (see Example 16). It is believed that the CD59 found in chimpanzees confers a resistance to the progression of AIDS that is not found in humans. Thus, the positively selected chimpanzee CD59 can serve in the development of agents or drugs that are useful in arresting the progression of AIDS in humans, as is described in the Examples.

Another example involves the p44 polynucleotides and polypeptides associated with resistance to HCV infection in chimpanzees. This discovery can be useful in discerning the molecular mechanisms that underlie resistance to HCV infection progression to chronic hepatitis and/or hepatocellular carcinoma in chimpanzees, and in providing information useful in the discovery and/or design of agents that prevent and/or delay chronic hepatitis or hepatocellular carcinoma.

Commercially relevant examples include, but are not limited to, polynucleotides and polypeptides that are positively selected in non-human primates that may be associated with aesthetic traits, such as hair growth, acne, or muscle mass. Accordingly, in one aspect, the invention provides methods for identifying a polynucleotide sequence encoding a polypeptide, wherein said polypeptide may be associated with a medically or commercially relevant positive evolutionarily significant change. The method comprises the steps of: (a) comparing human protein-coding nucleotide sequences to protein-coding nucleotide sequences of a non-human primate; and (b) selecting a non-human primate polynucleotide sequence that contains at least one nucleotide change as compared to corresponding sequence of the human, wherein said change is evolutionarily significant. The sequences identified by this method may be further characterized and/or analyzed for their possible association with biologically or medically relevant functions unique or enhanced in non-human primates.

Methods Useful for Identifying Positively Selected Human Traits

This invention specifically provides methods for identifying human polynucleotide and polypeptide sequences that may be associated with unique or enhanced functional capabilities or traits of the human, for example, brain function or longer life span. More particularly, these methods identify those genetic sequences that may be associated with capabilities that are unique or enhanced in humans, including, but not limited to, brain functions such as high capacity information processing, storage and retrieval capabilities, creativity, and language abilities. Moreover, these methods identify those sequences that may be associated to other brain functional features with respect to which the human brain performs at enhanced levels as compared to other non-human primates; these differences may include brain-mediated emotional response, locomotion, pain/pleasure sensation, olfaction, temperament and longer life span.

In this method, the general methods of the invention are applied as described above. Generally, the methods described herein entail (a) comparing human protein-coding polynucleotide sequences to that of a non-human primate; and (b) selecting those human protein-coding polynucleotide sequences having evolutionarily significant changes that may be associated with unique or enhanced functional capabilities of the human as compared to that of the non-human primate.

In this embodiment, the human sequence includes the evolutionarily significant change (i.e., the human sequence differs from more than one non-human primate species sequence in a manner that suggests that such a change is in response to a selective pressure). The identity and function of the protein encoded by the gene that contains the evolutionarily significant change is characterized and a determination is made whether or not the protein can be involved in a unique or enhanced human function. If the protein is involved in a unique or enhanced human function, the information is used in a manner to identify agents that can supplement or otherwise modulate the unique or enhanced human function.

As a non-limiting example of the invention, identifying the genetic (i.e., nucleotide sequence) differences underlying the functional uniqueness of human brain may provide a basis for designing agents that can modulate human brain functions and/or help correct functional defects. These sequences could also be used in developing diagnostic reagents and/or biomedical research tools. The invention also provides methods for a large-scale comparison of human brain protein-coding sequences with those from a non-human primate.

The identified human sequence changes can be used in establishing a database of candidate human genes that may be involved in human brain function. Candidates are ranked as to the likelihood that the gene is responsible for the unique or enhanced functional capabilities found in the human brain compared to chimpanzee or other non-human primates. Moreover, the database not only provides an ordered collection of candidate genes, it also provides the precise molecular sequence differences that exist between human and chimpanzee (and other non-human primates), and thus defines the changes that underlie the functional differences. This information can be useful in the identification of potential sites on the protein that may serve as useful targets for pharmaceutical agents.

Accordingly, the present invention also provides methods for correlating an evolutionarily significant nucleotide change to a brain functional capability that is unique or enhanced in humans, comprising (a) identifying a human nucleotide sequence according to the methods described above; and (b) analyzing the functional effect of the presence or absence of the identified sequence in a model system.

Further studies can be carried out to confirm putative function. For example, the putative function can be assayed in appropriate in vitro assays using transiently or stably transfected mammalian cells in culture, or using mammalian cells transfected with an antisense clone to inhibit expression of the identified polynucleotide to assess the effect of the absence of expression of its encoded polypeptide. Studies such as one-hybrid and two-hybrid studies can be conducted to determine, for example, what other macromolecules the polypeptide interacts with. Transgenic nematodes or *Drosophila* can be used for various functional assays, including behavioral studies. The appropriate studies depend on the nature of the identified polynucleotide and the polypeptide encoded within the polynucleotide, and would be obvious to those skilled in the art.

The present invention also provides polynucleotides and polypeptides identified by the methods of the present invention. In one embodiment, the present invention provides an isolated AATYK nucleotide sequence selected from the group consisting of nucleotides 2180-2329 of SEQ ID NO:14, nucleotides 2978-3478 of SEQ ID NO:14, and nucleotides 3380-3988 of SEQ ID NO:14; and an isolated nucleotide sequence having at least 85% homology to a nucleotide sequence of any of the preceding sequences.

In another embodiment, the invention provides an isolated AATYK polypeptide selected from the group consisting of a polypeptide encoded by a nucleotide sequence selected from the group consisting of SEQ ID NO:17 and SEQ ID NO:18; wherein said encoding is based on the open reading frame (ORF) of SEQ ID NO:14, and a polypeptide encoded by a nucleotide sequence having at least 85% homology to a nucleotide sequence selected from the group consisting of SEQ ID NO:17 and SEQ ID NO:18; wherein said encoding is based on the open reading frame of SEQ ID NO:14.

In a further embodiment, the present invention provides an isolated AATYK polypeptide selected from the group consisting of a polypeptide encoded by a nucleotide sequence selected from the group consisting of nucleotides 1-501 of SEQ ID NO:17, nucleotides 1-150 of SEQ ID NO:17, nucleotides 100-249 of SEQ ID NO:17, nucleotides 202-351 of SEQ ID NO:17, nucleotides 301-450 of SEQ ID NO:17, nucleotides 799-948 of SEQ ID NO:17, nucleotides 901-1050 of SEQ ID NO:17, nucleotides 799-1299 of SEQ ID NO:17, and nucleotides 1201-1809 of SEQ ID NO:17; wherein said encoding is based on the open reading frame of SEQ ID NO:14; and a polypeptide encoded by a nucleotide sequence having at least 85% homology to any of the preceding nucleotide sequences.

In still another embodiment, the invention provides an isolated polypeptide selected from the group consisting of a polypeptide encoded by a nucleotide sequence selected from the group consisting of nucleotides 1-501 of SEQ ID NO:18, nucleotides 799-1299 of SEQ ID NO:18, and nucleotides 1201-1809 of SEQ ID NO:18; wherein said encoding is based on the open reading frame of SEQ ID NO:14; and a polypeptide encoded by a nucleotide sequence having at least 85% homology to nucleotides 1-501 of SEQ ID NO:18. nucleotides 799-1299 of SEQ ID NO:18, and nucleotides 1201-1809 of SEQ ID NO:18.

In another embodiment, the invention provides an isolated polynucleotide comprising SEQ ID NO:17, wherein the coding capacity of the nucleic acid molecule is based on the open reading frame of SEQ ID NO:14. In a preferred embodiment, the polynucleotide is a *Pan troglodytes* polynucleotide.

In another embodiment, the invention provides an isolated polynucleotide comprising SEQ ID NO:18, wherein the coding capacity of the nucleic acid molecule is based on the open reading frame of SEQ ID NO:14. In a preferred embodiment, the polynucleotide is a *Gorilla gorilla* polynucleotide.

In some embodiments, the polynucleotide or polypeptide having 85% homology to an isolated AATYK polynucleotide or polypeptide of the present invention is a homolog, which, when compared to a non-human primate, yields a $K_A/K_S$ ratio of at least 0.75, at least 1.00, at least 1.25, at least 1.50, or at least 2.00.

In other embodiments, the polynucleotide or polypeptide having 85% homology to an isolated AATYK polynucleotide or polypeptide of the present invention is a homolog which is capable of performing the function of the natural AATYK polynucleotide or polypeptide in a functional assay. Suitable assays for assessing the function of an ATTYK polynucleotide or polypeptide include a neuronal differentiation assay such as that described by Raghunath, et al., *Brain Res Mol Brain Res.* (2000) 77:151-62, or a tyrosine phosphorylation assay such as that described in Tomomura, et al., *Oncogene* (2001) 20(9):1022-32. The phrase "capable of performing the function of the natural AATYK polynucleotide or polypeptide in a functional assay" means that the polynucleotide or polypeptide has at least about 10% of the activity of the natural polynucleotide or polypeptide in the functional assay. In other preferred embodiments, has at least about 20% of the activity of the natural polynucleotide or polypeptide in the functional assay. In other preferred embodiments, has at least about 30% of the activity of the natural polynucleotide or polypeptide in the functional assay. In other preferred embodiments, has at least about 40% of the activity of the natural polynucleotide or polypeptide in the functional assay. In other preferred embodiments, has at least about 50% of the activity of the natural polynucleotide or polypeptide in the functional assay. In other preferred embodiments, the polynucleotide or polypeptide has at least about 60% of the activity of the natural polynucleotide or polypeptide in the functional assay. In more preferred embodiments, the polynucleotide or polypeptide has at least about 70% of the activity of the natural polynucleotide or polypeptide in the functional assay. In more preferred embodiments, the polynucleotide or polypeptide has at least about 80% of the activity of the natural polynucleotide or polypeptide in the functional assay. In more preferred embodiments, the polynucleotide or polypeptide has at least about 90% of the activity of the natural polynucleotide or polypeptide in the functional assay.

Description of the AIDS Embodiment (an Example of a Positively Selected Non-Human Trait)

The AIDS (Acquired Immune Deficiency Syndrome) epidemic has been estimated to threaten 30 million people world-wide (UNAIDS/WHO, 1998, "Report on the global HIV/AIDS epidemic"). Well over a million people are infected in developed countries, and in parts of sub-Saharan Africa, 1 in 4 adults now carries the virus (UNAIDS/WHO, 1998). Although efforts to develop vaccines are underway, near term prospects for successful vaccines are grim. Balter and Cohen (1998) *Science* 281:159-160; Baltimore and Heilman (1998) *Scientific Am.* 279:98-103. Further complicating the development of therapeutics is the rapid mutation rate of HIV (the human immunodeficiency virus which is responsible for AIDS), which generates rapid changes in viral proteins. These changes ultimately allow the virus to escape current therapies, which target viral proteins. Dobkin (1998) *Inf. Med.* 15(3):159. Even drug cocktails which initially showed great promise are subject to the emergence of drug-resistant mutants. Balter and Cohen (1998); Dobkin (1998). Thus, there is still a serious need for development of therapies which delay or prevent progression of AIDS in HIV-infected individuals. Chun et al. (1997) *Proc. Natl. Acad. Sci. USA* 94:13193-13197; Dobkin (1998).

Human=s closest relatives, chimpanzees (*Pan troglodytes*), have unexpectedly proven to be poor models for the study of the disease processes following infection with HIV-1. Novembre et al. (1997); *J. Virol.* 71(5):4086-4091. Once infected with HIV-1, chimpanzees display resistance to progression of the disease. To date, only one chimpanzee individual is known to have developed full-blown AIDS, although more than 100 captive chimpanzees have been infected. Novembre et al. (1997); Villinger et al. (1997) *J. Med. Primatol.* 26(1-2):11-18. Clearly, an understanding of the mechanism(s) that confer resistance to progression of the disease in chimpanzees may prove invaluable for efforts to develop therapeutic agents for HIV-infected humans.

It is generally believed that wild chimpanzee populations harbored the HIV-1 virus (perhaps for millennia) prior to its recent cross-species transmission to humans. Dube et al., (1994); *Virology* 202:379-389: Zhu and Ho (1995) *Nature* 374:503-504; Zhu et al. (1998); Quinn (1994) *Proc. Natl. Acad. Sci USA* 91:2407-2414. During this extended period, viral/host co-evolution has apparently resulted in accommodation, explaining chimpanzee resistance to AIDS progression. Burnet and White (1972); *Natural History of Infectuous Disease* (Cambridge, Cambridge Univ. Press); Ewald (1991) *Hum. Nat.* 2(i):1-30. All references cited herein are hereby incorporated by reference in their entirety.

One aspect of this invention arises from the observations that (a) because chimpanzees (*Pan troglodytes*) have displayed resistance to development of AIDS although susceptible to HIV infection (Alter et al. (1984) *Science* 226:549-552; Fultz et al. (1986) *J. Virol.* 58:116-124; Novembre et al. (1997) *J. Virol.* 71(5):4086-4091), while humans are susceptible to developing this devastating disease, certain genes in chimpanzees may contribute to this resistance; and (b) it is possible to evaluate whether changes in human genes when compared to homologous genes from other species (such as chimpanzee) are evolutionarily significant (i.e., indicating positive selective pressure). Thus, protein coding polynucleotides may contain sequence changes that are found in chimpanzees (as well as other AIDS-resistant primates) but not in humans, likely as a result of positive adaptive selection during evolution. Furthermore, such evolutionarily significant changes in polynucleotide and polypeptide sequences may be attributed to an AIDS-resistant non-human primate=s (such as chimpanzee) ability to resist development of AIDS. The methods of this invention employ selective comparative analysis to identify candidate genes which may be associated with susceptibility or resistance to AIDS, which may provide new host targets for therapeutic intervention as well as specific information on the changes that evolved to confer resistance. Development of therapeutic approaches that involve host proteins (as opposed to viral proteins and/or mechanisms) may delay or even avoid the emergence of resistant viral mutants. The invention also provides screening methods using the sequences and structural differences identified.

This invention provides methods for identifying human polynucleotide and polypeptide sequences that may be associated with susceptibility to post-infection development of AIDS. Conversely, the invention also provides methods for identifying polynucleotide and polypeptide sequences from an AIDS-resistant non-human primate (such as chimpanzee) that may be associated with resistance to development of AIDS. Identifying the genetic (i.e., nucleotide sequence) and the resulting protein structural and biochemical differences underlying susceptibility or resistance to development of AIDS will likely provide a basis for discovering and/or designing agents that can provide prevention and/or therapy for HIV infection progressing to AIDS. These differences could also be used in developing diagnostic reagents and/or biomedical research tools. For example, identification of proteins which confer resistance may allow development of diagnostic reagents or biomedical research tools based upon the disruption of the disease pathway of which the resistant protein plays a part.

Generally, the methods described herein entail (a) comparing human protein-coding polynucleotide sequences to that of an AIDS resistant non-human primate (such as chimpanzee), wherein the human protein coding polynucleotide sequence is associated with development of AIDS; and (b) selecting those human protein-coding polynucleotide sequences having evolutionarily significant changes that may be associated with susceptibility to development of AIDS. In another embodiment, the methods entail (a) comparing human protein-coding polynucleotide sequences to that of an AIDS-resistant non-human primate (such as chimpanzee), wherein the human protein coding polynucleotide sequence is associated with development of AIDS; and (b) selecting those non-human primate protein-coding polynucleotide sequences having evolutionarily significant changes that may be associated with resistance to development of AIDS.

As is evident, the methods described herein can be applied to other infectious diseases. For example, the methods could be used in a situation in which a non-human primate is known or believed to have harbored the infectious disease for a significant period (i.e., a sufficient time to have allowed positive selection) and is resistant to development of the disease. Thus, in other embodiments, the invention provides methods for identifying a polynucleotide sequence encoding a polypeptide, wherein said polypeptide may be associated with resistance to development of an infectious disease, comprising the steps of: (a) comparing infectious disease-resistant non-human primate protein coding sequences to human protein coding sequences, wherein the human protein coding sequence is associated with development of the infectious disease; and (b) selecting an infectious disease-resistant non-human primate sequence that contains at least one nucleotide change as compared to the corresponding human sequence, wherein the nucleotide change is evolutionarily significant. In another embodiment, the invention provides methods for identifying a human polynucleotide sequence encoding a polypeptide, wherein said polypeptide may be associated with susceptibility to development of an infectious disease, comprising the steps of: (a) comparing human protein coding sequences to protein-coding polynucleotide sequences of an infectious disease-resistant non-human primate, wherein the human protein coding sequence is associated with development of the infectious disease; and (b) selecting a human polynucleotide sequence that contains at least one nucleotide change as compared to the corresponding sequence of an infectious disease-resistant non-human primate, wherein the nucleotide change is evolutionarily significant.

In the present invention, human sequences to be compared with a homologue from an AIDS-resistant non-human primate are selected based on their known or implicated association with HIV propagation (i.e., replication), dissemination and/or subsequent progression to AIDS. Such knowledge is obtained, for example, from published literature and/or public databases (including sequence databases such as GenBank). Because the pathway involved in development of AIDS (including viral replication) involves many genes, a number of suitable candidates may be tested using the methods of this invention. Table 1 contains a exemplary list of genes to be examined. The sequences are generally known in the art.

TABLE 1

Sample List of Human Genes to be/have been Examined

| Gene | Function |
|---|---|
| eIF-5A | initiation factor |
| hPC6A | protease |
| hPC6B | protease |
| P56$^{lck}$ | Signal transduction |
| FK506-binding protein | Immunophilin |
| calnexin | ? |
| Bax | PCD promoter |
| bcl-2 | apoptosis inhibitor |
| lck | tyrosine kinase |
| MAPK (mitogen activated protein kinase) | protein kinase |
| CD43 | sialoglycoprotein |
| CCR2B | chemokine receptor |
| CCR3 | chemokine receptor |
| Bonzo | chemokine receptor |
| BOB | chemokine receptor |
| GPR1 | chemokine receptor |
| stromal-derived factor-1 (SDF-1) | chemokine |
| tumor-necrosis factor-α (TNF-α) | PCD promoter |
| TNF-receptor II (TNFRII) | receptor |
| interferon γ (IFN-γ) | cytokine |
| interleukin 1 α(IL-1 α) | cytokine |
| interleukin 1β(IL-1 β) | cytokine |
| interleukin 2 (IL-2) | cytokine |
| interleukin 4 (IL-4) | cytokine |
| interleukin 6 (IL-6) | cytokine |
| interleukin 10 (IL-10) | cytokine |
| interleukin 13 (IL-13) | cytokine |
| B7 | signaling protein |

TABLE 1-continued

Sample List of Human Genes to be/have been Examined

| Gene | Function |
| --- | --- |
| macrophage colony-stimulating factor (M-CSF) | cytokine |
| granulocyte-macrophage colony-stimulating factor | cytokine |
| phosphatidylinositol 3-kinase (PI 3-kinase) | kinase |
| phosphatidylinositol 4-kinase (PI 4-kinase) | kinase |
| HLA class I α chain | histocompatibility antigen |
| β$_2$ microglobulin | lymphocyte antigen |
| CD55 | decay-accelerating factor |
| CD63 | glycoprotein antigen |
| CD71 | ? |
| interferon α (IFN- α) | cytokine |
| CD44 | cell adhesion |
| CD8 | glycoprotein |
| Genes already examined (13) | |
| ICAM-1 | Immune system |
| ICAM-2 | Immune system |
| ICAM-3 | Immune system |
| leukocyte associated function 1 molecule α (LFA-1) | Immune system |
| leukocyte associated function 1 molecule β (LFA-1) | Immune system |
| Mac-1 α | Immune system |
| Mac-1 β (equivalent to LFA-1β) | Immune system |
| DC-SIGN | Immune system |
| CD59 | complement protein |
| CXCR4 | chemokine receptor |
| CCR5 | chemokine receptor |
| MIP-1α | chemokine |
| MIP-1β | chemokine |
| RANTES | chemokine |

Aligned protein-coding sequences of human and an AIDS resistant non-human primate such as chimpanzee are analyzed to identify nucleotide sequence differences at particular sites. The detected sequence changes are generally, and preferably, initially checked for accuracy as described above. The evolutionarily significant nucleotide changes, which are detected by molecular evolution analysis such as the $K_A/K_S$ analysis, can be further assessed to determine whether the non-human primate gene or the human gene has been subjected to positive selection. For example, the identified changes can be tested for presence/absence in other AIDS-resistant non-human primate sequences. The sequences with at least one evolutionarily significant change between human and one AIDS-resistant non-human primate can be used as primers for PCR analysis of other non-human primate protein-coding sequences, and resulting polynucleotides are sequenced to see whether the same change is present in other non-human primates. These comparisons allow further discrimination as to whether the adaptive evolutionary changes are unique to the AIDS-resistant non-human primate (such as chimpanzee) as compared to other non-human primates. For example, a nucleotide change that is detected in chimpanzee but not other primates more likely represents positive selection on the chimpanzee gene. Other non-human primates used for comparison can be selected based on their phylogenetic relationships with human. Closely related primates can be those within the hominoid sublineage, such as chimpanzee, bonobo, gorilla, and orangutan. Non-human primates can also be those that are outside the hominoid group and thus not so closely related to human, such as the Old World monkeys and New World monkeys. Statistical significance of such comparisons may be determined using established available programs, e.g., t-test as used by Messier and Stewart (1997) *Nature* 385:151-154.

Furthermore, sequences with significant changes can be used as probes in genomes from different humans to see whether the sequence changes are shared by more than one individual. For example, certain individuals are slower to progress to AIDS ("slow progressers") and comparison (a) between a chimpanzee sequence and the homologous sequence from the slow-progresser human individual and/or (b) between an AIDS-susceptible individual and a slow-progresser individual would be of interest. Gene sequences from different human populations can be obtained from databases made available by, for example, the human genome diversity project or, alternatively, from direct sequencing of PCR-amplified DNA from a number of unrelated, diverse human populations. The presence of the identified changes in human slow progressers would further indicate the evolutionary significance of the changes.

As is exemplified herein, the CD59 protein, which has been associated with the chimpanzee=s resistance to the progression of AIDS, exhibits an evolutionarily significant nucleotide change relative to human CD59. CD59 (also known as protectin, 1F-5Ag, H19, HRF20, MACIF, MIRL and P-18) is expressed on peripheral blood leukocytes and erythrocytes, and functions to restrict lysis of human cells by complement (Meri et al. (1996) *Biochem. J.* 316:923). More specifically, CD59 acts as an inhibitor of membrane attack complexes, which are complement proteins that make hole-like lesions in the cell membranes. Thus, CD59 protects the cells of the body from the complement arm of its own defense system (Meri et al, supra). The chimpanzee homolog of this protein was examined because the human homolog has been implicated in the progression of AIDS in infected individuals. It has been shown that CD59 is one of the host cell derived proteins that is selectively taken up by HIV virions (Frank et al. (1996) *AIDS* 10:1611). Additionally, it has been shown that HIV virions that have incorporated host cell CD59 are protected from the action of complement. Thus, in humans, HIV uses CD59 to protect itself from attack by the victim=s immune system, and thus to further the course of infection. As is theorized in the examples, positively-selected chimpanzee CD59 may constitute the adaptive change that inhibits disease progression. The virus may be unable to usurp the chimpanzee=s CD59 protective role, thereby rendering the virus susceptible to the chimpanzee=s immune system.

As is further exemplified herein, the DC-SIGN protein has also been determined to be positively selected in the chimpanzee as compared to humans and gorilla. DC-SIGN is expressed on dendritic cells and has been documented to provide a mechanism for travel of the HIV-1 virus to the lymph nodes where it infects undifferentiated T cells (Geijtenbeek, T. B. H. et al. (2000) Cell 100:587-597). Infection of the T cells ultimately leads to compromise of the immune system and subsequently to full-blown AIDS. The HIV-1 virus binds to the extracellular portion of DC-SIGN, and then gains access to the T cells via their CD4 proteins. DC-SIGN has as its ligand ICAM-3, which has a very high $K_A/K_S$ ratio. It may be that the positive selection on chimpanzee ICAM-3 was a result of compensatory changes to permit continued binding to DC-SIGN. As is theorized in the examples, positively-selected chimpanzee DC-SIGN may constitute another adaptive change that inhibits disease progression. Upon resolution of the three-dimensional structure of chimpanzee DC-SIGN and identification of the mechanism by which HIV-1 is prevented from binding to DC-SIGN, it may be possible to design drugs to mimic the effects of chimpanzee DC-SIGN without disrupting the normal functions of human DC-SIGN.

Description of the HCV Embodiment (an Example of a Positively Selected Non-Human Trait)

Some four million Americans are infected with the hepatitis C virus (HCV), and worldwide, the number approaches 40 million (Associated Press, Mar. 11, 1999). Many of these victims are unaware of the infection, which can lead to hepatocellular carcinoma. This disease is nearly always fatal. Roughly 14,500 Americans die each year as a result of the effects of hepatocellular carcinoma (Associated Press, Mar. 11, 1999). Thus identification of therapeutic agents that can ameliorate the effects of chronic infection are valuable both from an ethical and commercial viewpoint.

The chimpanzee is the only organism, other than humans, known to be susceptible to HCV infection (Lanford, R. E. et al. (1991) J. Med. Virol. 34:148-153). While the original host population for HCV has not yet been documented, it is likely that the virus must have originated in either humans or chimpanzees, the only two known susceptible species. It is known that the continent-of-origin for HCV is Africa (personal communication, A. Siddiqui, University of Colorado Health Science Center, Denver). If the chimpanzee population were the original host for HCV, as many HCV researchers believe (personal communication, A. Siddiqui, University of Colorado Health Science Center), then, as is known to be true for the HIV virus, chimpanzees would likely have evolved resistance to the virus. This hypothesis is supported by the well-documented observation that HCV-infected chimpanzees are refractory to the hepatic damage that often occurs in hepatitis C-infected humans (Walker. C. M (1997) Springer Semin. Immunopathol. 19:85-98; McClure, H. M., pp. 121-133 in *The Role of the Chimpanzee in Research*, ed. by Eder, G. et al., 1994, Basel: Karger; Agnello, V. et al. (1998) Hepatology 28:573-584). In fact, although in 2% of HCV-infected humans, the disease course leads to hepatocellular carcinoma, HCV-infected chimpanzees do not develop these tumors (Walker, C. M (1997) Springer Semin. lmmunopathol. 19:85-98). Further support for the hypothesis that chimpanzees were the original host population, and that they have, as a result of prolonged experience with the virus, evolved resistance to the ravages of HCV-induced disease, is added by the observation that HCV-infected chimpanzees in general have a milder disease course (i.e., not simply restricted to hepatic effects) than do humans (Lanford, R. E. et al. (1991) J. Med. Virol. 34:148-153; and Walker, C. M (1997) Springer Semin. Immunopathol. 19:85-98).

As is exemplified herein, the p44 gene in chimpanzees has been positively selected relative to its human homolog. The p44 protein was first identified in liver tissues of chimpanzees experimentally infected with HCV (Shimizu, Y. et al. (1985) PNAS USA 82:2138).

The p44 gene, and the protein it codes for, represents a potential therapeutic target, or alternatively a route to a therapeutic, for humans who are chronically infected with hepatitis C. The protein coded for by this gene in chimpanzees is known to be up-regulated in chimpanzee livers after experimental infection of captive chimpanzees (Takahashi, K. et al. (1990) J. Gen. Virol. 71:2005-2011). The p44 gene has been shown to be a member of the family of $\alpha/\beta$ interferon inducible genes (Kitamura, A. et al. (1994) Eur. J. Biochem. 224:877-883). It is suspected that the p44 protein is a mediator in the antiviral activities of interferon.

This is most suggestive, since as noted above, HCV-infected chimpanzees have been documented to be refractory to the hepatic damage that often occurs in HCV-infected humans. The combination of the observations that this protein is only expressed in chimpanzee livers after hepatitis C infection, the fact that chimpanzees are refractory to the hepatic damage that can occur in humans (Agnello, V. et al. (1998) Hepatology 28:573-584), the observation that HCV-infected chimpanzees in general have a milder disease course than do humans, and that the p44 gene has been positively selected in chimpanzees, strongly suggest that the chimpanzee p44 protein confers resistance to hepatic damage in chimpanzees. Whether the protein is responsible for initiating some type of cascade in chimpanzees that fails to occur in infected humans, or whether the selected chimpanzee homolog differs in some critical biochemical functions from its human homolog, is not yet clear. It has been speculated that the milder disease course observed in chimpanzees may be due in part to lower levels of viral replication (Lanford, R. E. et al. (1991) J. Med. Virol. 34:148-153).

This invention includes the medical use of the specific amino acid residues by which chimpanzee p44 differs from human p44. These residues that were positively selected during the period in which chimpanzees evolved an accommodation to the virus, allow the intelligent design of an effective therapeutic approach for chronically HCV-infected humans. Several methods to induce a chimpanzee-like response in infected humans will be apparent to one skilled in the art. Possibilities include the intelligent design of a small molecule therapeutic targeted to the human homolog of the specific amino acid residues selected in chimpanzee evolution. Use of molecular modeling techniques might be valuable here, as one could design a small molecule that causes the human protein to mimic the three-dimensional structure of the chimpanzee protein. Another approach would be the design of a small molecule therapeutic that induces a chimpanzee-like functional response in human p44. Again, this could only be achieved by use of the knowledge obtained by this invention. i.e., which amino acid residues were positively selected to confer resistance to HCV in chimpanzees. Other possibilities will be readily apparent to one skilled in the art.

In addition to screening candidate agents for those that may favorably interact with the human p44 (exon 2) polypeptide so that it may mimic the structure and/or function of chimpanzee p44, the subject invention also concerns the screening of candidate agents that interact with the human p44 polynucleotide promoter, whereby the expression of human p44 may be increased so as to improve the human patient's resistance to HCV infection. Thus, the subject invention includes a method for identifying an agent that modulates expression of a human's p44 polynucleotide, by contacting at least one candidate agent with the human's p44 polynucleotide promoter, and observing whether expression of the human p44 polynucleotide is enhanced. The human p44 promoter has been published in Kitamura et al. (1994) Eur. J. Biochem. 224:877 (FIG. 4).

Description of the Breast Enhancement Embodiment (an Example of a Positively Selected Human Trait)

Relative to non-human primates, female humans exhibit pre-pregnancy, pre-lactation expanded breast tissue. As is discussed in the Examples, this secondary sex characteristic is believed to facilitate evolved behaviors in humans associated with long term pair bonds and long-term rearing of infants. One aspect of this invention concerns identifying those human genes that have been positively selected in the development of enlarged breasts. Specifically, this invention includes a method of determining whether a human polynucleotide sequence which has been associated with enlarged breasts in humans has undergone evolutionarily significant change relative to a non-human primate that does not manifest enlarged breasts, comprising: a) comparing the human polynucleotide sequence with the corresponding non-human primate polynucleotide sequence to identify any nucleotide changes; and b) determining whether the human nucleotide changes are evolutionarily significant.

It has been found that the human BRCA1 gene, which has been associated with normal breast development in humans, has been positively selected relative to the BRCA1 gene of chimpanzees and other non-human primates. The identified evolutionarily significant nucleotide changes could be useful in developing agents that can modulate the function of the BRCA1 gene or protein.

Therapeutic Compositions that Comprise Agents

As described herein, agents can be screened for their capacity to increase or decrease the effectiveness of the positively selected polynucleotide or polypeptide identified according to the subject methods. For example, agents that may be suitable for enhancing breast development may include those which interact directly with the BRCA1 protein or its ligand, or which block inhibitors of BRCA1 protein. Alternatively, an agent may enhance breast development by increasing BRCA1 expression. As the mechanism of BRCA1 is further elucidated, strategies for enhancing its efficacy can be devised.

In another example, agents that may be suitable for reducing the progression of AIDS could include those which directly interact with the human CD59 protein in a manner to make the protein unusable to the HIV virion, possibly by either rendering the human CD59 unsuitable for packing in the virion particle or by changing the orientation of the protein with respect to the cell membrane (or via some other mechanism). The candidate agents can be screened for their capacity to modulate CD59 function using an assay in which the agents are contacted with HIV infected cells which express human CD59, to determine whether syncytia formation or other indicia of the progression of AIDS are reduced. The assay may permit the detection of whether the HIV virion can effectively pack the CD59 and/or utilize the CD59 to inhibit attack by MAC complexes.

One agent that may slow AIDS progression is a human CD59 that has been modified to have multiple GPI links. As described herein, chimp CD59, which contains three GPI links as compared to the single GPI link found in human CD59, slows progression of HIV infections in chimps. Preferably, the modified human CD59 contains three GPI links in tandem.

Another example of an agent that may be suitable for reducing AIDS progression is a compound that directly interacts with human DC-SIGN to reduce its capacity to bind to HIV-1 and transport it to the lymph nodes. Such an agent could bind directly to the HIV-1 binding site on DC-SIGN. The candidate agents can be contacted with dendritic cells expressing DC-SIGN or with a purified extracellular fragment of DC-SIGN and tested for their capacity to inhibit HIV-1 binding.

Various delivery systems are known in the art that can be used to administer agents identified according to the subject methods. Such delivery systems include aqueous solutions, encapsulation in liposomes, microparticles or microcapsules or conjugation to a moiety that facilitates intracellular admission.

Therapeutic compositions comprising agents may be administered parenterally by injection, although other effective administration forms, such as intra-articular injection, inhalant mists, orally-active formulations, transdermal iontophoresis or suppositories are also envisioned. The carrier may contain other pharmacologically-acceptable excipients for modifying or maintaining the pH, osmolarity, viscosity, clarify, color, sterility, stability, rate of dissolution, or odor of the formulation. The carrier may also contain other pharmacologically-acceptable excipients for modifying or maintaining the stability, rate of dissolution, release or absorption of the agent. Such excipients are those substances usually and customarily employed to formulate dosages for parenteral administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing agents for systemic delivery may be via subcutaneous, intramuscular, intravenous, intranasal or vaginal or rectal suppository. Alternatively, the formulations may be administered directly to the target organ (e.g., breast).

The amount of agent which will be effective in the treatment of a particular disorder or condition will depend on the nature of the disorder or condition, which can be determined by standard clinical techniques. In addition, in vitro or in vivo assays may optionally be employed to help identify optimal dosage ranges. The precise dose to be employed in the formulation will also depend on the route of administration, and the seriousness or advancement of the disease or condition, and should be decided according to the practitioner and each patient's circumstances. Effective doses may be extrapolated from dose-response curves derived from in vitro or animal model test systems. For example, an effective amount of an agent identified according to the subject methods is readily determined by administering graded doses of a bivalent compound of the invention and observing the desired effect.

Description of a Method for Obtaining Candidate Polynucleotides that may be Associated with Human Diseases, and Diagnostic Methods Derived Therefrom According to the subject invention, BRCA1 exon 11 is an evolutionarily significant polynucleotide that has undergone positive selection in humans relative to chimpanzees, and is associated with the enhanced breast development observed in humans relative to chimpanzees (see Example 14). Exon 11 has also been found to have mutations that are associated with the development of breast cancer. BRCA1 exon 11 mutations are known to be associated with both familial and spontaneous breast cancers (Kachhap, S. K. et al. (2001) Indian J. Exp. Biol. 39(5):391-400; Hadjisavvas, A. et al. (2002) Oncol. Rep. 9(2):383-6; Khoo, U. S. et al. (1999) Oncogene 18(32): 4643-6).

Encompassed within the subject invention are methods that are based on the principle that human polynucleotides that are evolutionarily significant relative to a non-human primate, and which are associated with a improved physiological condition in the human, may also be associated with decreased resistance or increased susceptibility to one or more diseases. In one embodiment, mutations in positively selected human BRCA1 polynucleotide exon 11 may be linked to elevated risk of breast, ovarian and/or prostate cancer. This phenomenon may represent a trade-off between enhanced development of one trait and loss or reduction in another trait in polynucleotides encoding polypeptides of multiple functions. In this way, identification of positively selected human polynucleotides can serve to identify a pool of genes that are candidates for susceptibility to human diseases.

Thus, in one embodiment, the subject invention provides a method for obtaining a pool of candidate polynucleotides that are useful in screening for identification of polynucleotides associated with increased susceptibility or decreased resistance to one or more human diseases. The method of identifying the candidate polynucleotides comprises comparing the human polynucleotide sequences with non-human primate polynucleotide sequences to identify any nucleotide changes, and determining whether those nucleotide changes are evolutionarily significant. Evolutionary significance can be determined by any of the methods described herein including the $K_A/K_S$ method. Because evolutionary significance involves the number of non-silent nucleotide changes over a defined length of polynucleotide, it is the polynucleotide containing the group of nucleotide changes that is referred to herein as "evolutionarily significant." That is, a single nucleotide change in a human polynucleotide relative to a non-human primate cannot be analyzed for evolutionary significance without considering the length of the polynucleotide and the existence or (non-existence) of other non-silent nucleotide changes in the defined polynucleotide. Thus, in referring to an "evolutionarily significant polynucleotide" and the nucleotide changes therein, the size of the polynucleotide is generally considered to be between about 30 and the total number of nucleotides encompassed in the polynucleotide or gene sequence (e.g., up to 3,000-5,000 nucleotides or longer). Further, while individual nucleotide changes cannot be analyzed in isolation as to their evolutionary significance, nucleotide changes that contribute to the evolutionary significance of a polynucleotide are referred to herein as "evolutionarily significant nucleotide changes."

The subject method further comprises a method of correlating an evolutionarily significant nucleotide change in a candidate polynucleotide to decreased resistance to development of a disease in humans, comprising identifying evolutionarily significant candidate polynucleotides as described herein, and further analyzing the functional effect of the evolutionarily significant nucleotide change(s) in one or more of the candidate polynucleotides in a suitable model system, wherein the presence of a functional effect indicates a correlation between the evolutionarily significant nucleotide change in the candidate polynucleotide and the decreased resistance to development of the disease in humans. As discussed herein, model systems may be cell-based or in vivo. For example, the evolutionarily significant human BRCA1 exon 11 (or variations thereof having fewer evolutionarily significant nucleotide changes) could be transfected or knock-out genomically inserted into mice or non-human primates (e.g., chimpanzees) to determine if it induces the functional effect of breast, ovarian or prostate cancer in the test animals. Such test results would indicate whether specific evolutionarily significant changes in exon 11 are associated with increased incidence of breast, ovarian or prostate cancer.

In addition to evaluating the evolutionarily significant nucleotide changes in candidate polynucleotides for their relevance to development of disease, the subject invention also includes the evaluation of other nucleotide changes of candidate human polynucleotides, such as alleles or mutant polynucleotides, that may be responsible for the development of the disease. For example, the evolutionarily significant BRCA1 exon 11 has a number of allelic or mutant exon 11s in human populations that have been found to be associated with breast, ovarian or prostate cancer (Rosen, E. M. et al. (2001) Cancer Invest. 19(4):396-412; Elit, L. et al. (2001) Int. J. Gynecol. Cancer I 1(3):241-3; Shen, D. et al. (2000) J. Natl. Med. Assoc. 92(1):29-35; Khoo, U.S. et al. (1999) Oncogene 18(32):4643-6; Presneau, N. et al. (1998) Hum. Genet. 103 (3):334-9; Dong, J. et al. (1998) Hum. Genet. 103(2):154-61; and Xu, C. F. et al. (1997) Genes Chromosomes 18(2):102-10). For example, Grade, K. et al. (1996) J. Cancer Res. Clin. Oncol. 122(11):702-6, report that of 127 human BRCA1 mutations published by 1996, 55% of them are localized in exon 11. Many of the cancer-causing mutations in BRCA1 exon 11 are not considered to be predominantly present in humans, and are therefore not considered to contribute to the evolutionary significance of BRCA1 exon 11. Polynucleotides that are strongly positively selected for the development of one trait in humans may be hotspots for nucleotide changes (evolutionarily significant or otherwise) that are associated with the development of a disease. Thus, according to the subject invention, identification of candidate polynucleotides that have been positively selected, is a very efficient start to identifying corresponding mutant or allelic polynucleotides associated with a disease.

To identify whether mutants or alleles of evolutionarily significant polynucleotides in humans can be correlated to decreased resistance or increased susceptibility to the disease, the variant polynucleotide can be tested in a suitable model, such as the MCF10a normal human epithelial cell line (Favy, D A et al. (2001) Biochem. Biophys. Res. Commun. 274(1):73-8). This model system for breast cancer can involve transfection of or knock-out genomic insertion into the MCF10a normal human breast epithelial cell line with mutant or allelic BRCA1 exon 11 polynucleotides to determine whether the nucleotide changes in the mutant or allelic polynucleotides result in conversion of the cell line to a neoplastic phenotype, i.e., a phenotype similar to cancer cell lines MCF-7, MDA-MB231 or HBL100 (Favy et al., supra). Additionally, mutants of candidate polynucleotides can be compared to patient genetic data to determine whether, for example, BRCA1 exon 11 mutant nucleotide changes are present in familial and/or sporadic breast, ovarian and/or prostate tumors. In this way, mutations in candidate evolutionarily significant human polynucleotides can be evaluated for their functional effect and their correlation to development of breast, ovarian and/or prostate cancer in humans.

The following examples are provided to further assist those of ordinary skill in the art. Such examples are intended to be illustrative and therefore should not be regarded as limiting the invention. A number of exemplary modifications and variations are described in this application and others will become apparent to those of skill in this art. Such variations are considered to fall within the scope of the invention as described and claimed herein.

EXAMPLES

Example 1 cDNA Library Construction

A chimpanzee cDNA library is constructed using chimpanzee tissue. Total RNA is extracted from the tissue (RNeasy kit, Quiagen; RNAse-free Rapid Total RNA kit, 5 Prime-3 Prime, Inc.) and the integrity and purity of the RNA are determined according to conventional molecular cloning methods. Poly A+ RNA is isolated (Mini-Oligo(dT) Cellulose Spin Columns, 5 Prime-3 Prime, Inc.) and used as template for the reverse-transcription of cDNA with oligo (dT) as a primer. The synthesized cDNA is treated and modified for cloning using commercially available kits. Recombinants are then packaged and propagated in a host cell line. Portions of the packaging mixes are amplified and the remainder retained prior to amplification. The library can be normalized and the numbers of independent recombinants in the library is determined.

Example 2

Sequence Comparison

Suitable primers based on a candidate human gene are prepared and used for PCR amplification of chimpanzee cDNA either from a cDNA library or from cDNA prepared from mRNA. Selected chimpanzee cDNA clones from the cDNA library are sequenced using an automated sequencer, such as an ABI 377. Commonly used primers on the cloning vector such as the M13 Universal and Reverse primers are used to carry out the sequencing. For inserts that are not completely sequenced by end sequencing. dye-labeled terminators are used to fill in remaining gaps.

The detected sequence differences are initially checked for accuracy, for example by finding the points where there are differences between the chimpanzee and human sequences: checking the sequence fluorogram (chromatogram) to determine if the bases that appear unique to human correspond to strong, clear signals specific for the called base; checking the human hits to see if there is more than one human sequence that corresponds to a sequence change; and other methods known in the art, as needed. Multiple human sequence entries for the same gene that have the same nucleotide at a position where there is a different chimpanzee nucleotide provides independent support that the human sequence is accurate, and that the chimpanzee/human difference is real. Such changes are examined using public database information and the genetic code to determine whether these DNA sequence changes result in a change in the amino acid sequence of the encoded protein. The sequences can also be examined by direct sequencing of the encoded protein.

Example 3

Molecular Evolution Analysis

The chimpanzee and human sequences under comparison are subjected to $K_A/K_S$ analysis. In this analysis, publicly available computer programs, such as Li 93 and INA, are used to determine the number of non-synonymous changes per site ($K_A$) divided by the number of synonymous changes per site ($K_S$) for each sequence under study as described above. Full-length coding regions or partial segments of a coding region can be used. The higher the $K_A/K_S$ ratio, the more likely that a sequence has undergone adaptive evolution. Statistical significance of $K_A/K_S$ values is determined using established statistic methods and available programs such as the t-test.

To further lend support to the significance of a high $K_A/K_S$ ratio, the sequence under study can be compared in multiple chimpanzee individuals and in other non-human primates, e.g., gorilla, orangutan, bonobo. These comparisons allow further discrimination as to whether the adaptive evolutionary changes are unique to the human lineage compared to other non-human primates. The sequences can also be examined by direct sequencing of the gene of interest from representatives of several diverse human populations to assess to what degree the sequence is conserved in the human species.

Example 4

Identification of Positively Selected ICAM-1, ICAM-2 and ICAM-3

Using the methods of the invention described herein, the intercellular adhesion molecules ICAM-1, ICAM-2 and ICAM-3 have been shown to have been strongly positively selected. The ICAM molecules are involved in several immune response interactions and are known to play a role in progression to AIDS in HIV infected humans. The ICAM proteins, members of the Ig superfamily, are ligands for the integrin leukocyte associated function 1 molecule (LFA-1). Makgoba et al. (1988) *Nature* 331:86-88. LFA-1 is expressed on the surface of most leukocytes, while ICAMs are expressed on the surface of both leukocytes and other cell types. Larson et al. (1989) *J. Cell Biol.* 108:703-712. ICAM and LFA-1 proteins are involved in several immune response interactions, including T-cell function, and targeting of leukocytes to areas of inflammation. Larson et al. (1989).

Total RNA was prepared using either the RNeasy® kit (Qiagen), or the RNAse-free Rapid Total RNA kit (5 Prime-3 Prime. Inc.) from primate tissues (chimpanzee brain and blood, gorilla blood and spleen, orangutan blood) or from cells harvested from the following B lymphocyte cell lines: CARL (chimpanzee), ROK (gorilla), and PUTI (orangutan). mRNA was isolated from total RNA using the Mini-Oligo (dT) Cellulose Spin Columns (5 Prime-3 Prime, Inc.). cDNA was synthesized from mRNA with oligo dT and/or random priming using the cDNA Synthesis Kit (Stratagene®). The protein-coding region of the primate ICAM-1 gene was amplified from cDNA using primers (concentration=100 nmole/μl) designed by hand from the published human sequence. PCR conditions for ICAM-1 amplification were 94° C. initial pre-melt (4 min), followed by 35 cycles of 94° C. (15 sec), 58° C. (1 min 15 sec), 72° C. (1 min 15 sec), and a final 72° C. extension for 10 minutes. PCR was accomplished using Ready-to-Go™ PCR beads (Amersham Pharmacia Biotech) in a 50 microliter total reaction volume. Appropriately-sized products were purified from agarose gels using the QiaQuick® Gel Extraction kit (Qiagen). Both strands of the amplification products were sequenced directly using the Big Dye Cycle Sequencing Kit and analyzed on a 373A DNA sequencer (ABI BioSystems).

Comparison of the protein-coding portions of the human, gorilla (*Gorilla gorilla*), and orangutan (*Pongo pygmaeus*) ICAM-1 genes to that of the chimpanzee yielded statistically significant $K_A/K_S$ ratios (Table 2). The protein-coding portions of the human and chimpanzee ICAM-1 genes were previously published and the protein-coding portions of gorilla (*Gorilla gorilla*), and orangutan (*Pongo pygmaeus*) ICAM-1 genes are shown in FIGS. 3 and 4, respectively.

For this experiment, pairwise $K_A/K_S$ ratios were calculated for the mature protein using the algorithm of Li (1985; 1993). Statistically significant comparisons (determined by t-tests) are shown in bold. Although the comparison to gorilla and human was sufficient to demonstrate that chimpanzee ICAM-1 has been positively-selected, the orangutan ICAM-1 was compared as well, since the postulated historical range of gorillas in Africa suggests that gorillas could have been exposed to the HIV-1 virus. Nowak and Paradiso (1983) *Walker=s Mammals of the World* (Baltimore, Md., The Johns Hopkins University Press). The orangutan, however, has always been confined to Southeast Asia and is thus unlikely to have been exposed to HIV over an evolutionary time frame. (Nowak and Paradiso, 1983) (Gorillas are most closely-related to humans and chimpanzees, while orangutans are more distantly-related.)

TABLE 2

$K_A/K_S$ Ratios: ICAM-1 Whole Protein Comparisons

| Species Compared | $K_A/K_S$ Ratio |
| --- | --- |
| Chimpanzee to Human | 2.1 ($P < 0.01$) |
| Chimpanzee to Gorilla | 1.9 ($P < 0.05$) |
| Chimpanzee to Orangutan | 1.4 ($P < 0.05$) |
| Human to Gorilla | 1.0 |
| Human to Orangutan | 0.87 |
| Gorilla to Orangutan | 0.95 |

Even among those proteins for which positive selection has been demonstrated, few show $K_A/K_S$ ratios as high as these ICAM-1 comparisons. Lee and Vacquier (1992) Biol. Bull. 182:97-104; Swanson and Vacquier (1995) Proc. Natl. Acad. Sci. USA 92:4957-4961; Messier and Stewart (1997); Sharp (1997) Nature 385:111-112. The results are consistent with strong selective pressure resulting in adaptive changes in the chimpanzee ICAM-1 molecule.

The domains (D1 and D2) of the ICAM-1 molecule which bind to LFA-1 have been documented. Staunton et al. (1990). Cell 61:243-254. Pairwise $K_A/K_S$ comparisons between primate ICAM-1 genes. $K_A/K_S$ ratios were calculated for domains D1 and D2 only, using the algorithm of Li (1985; 1993) (Table 3). Statistically significant comparisons (determined by t-tests) are shown in bold. The very high, statistically significant $K_A/K_S$ ratios for domains D1 and D2 suggest that these regions of the protein were very strongly positively-selected. These regions of chimpanzee ICAM-1 display even more striking $K_A/K_S$ ratios (Table 3) than are seen for the whole protein comparisons, thus suggesting that the ICAM-1/LFA-1 interaction has been subjected to unusually strong selective pressures.

TABLE 3

$K_A/K_S$ Ratios: Domains D1 + D2 of ICAM-1

| Species Compared | $K_A/K_S$ Ratio |
| --- | --- |
| Chimpanzee to Human | 3.1 ($P < 0.01$) |
| Chimpanzee to Gorilla | 2.5 ($P < 0.05$) |
| Chimpanzee to Orangutan | 1.5 ($P < 0.05$) |
| Human to Gorilla | 1.0 |
| Human to Orangutan | 0.90 |
| Gorilla to Orangutan | 1.0 |

Example 5

Characterization of ICAM-1, ICAM-2 and ICAM-3 Positively Selected Sequences A sequence identified by the methods of this invention may be further tested and characterized by cell transfection experiments. For example, human cells in culture, when transfected with a chimpanzee polynucleotide identified by the methods described herein (such as ICAM-1 (or ICAM-2 or ICAM-3); see below), could be tested for reduced viral dissemination and/or propagation using standard assays in the art, and compared to control cells. Other indicia may also be measured, depending on the perceived or apparent functional nature of the polynucleotide/polypeptide to be tested. For example, in the case of ICAM-1 (or ICAM-2 or ICAM-3), syncytia formation may be measured and compared to control (untransfected) cells. This would test whether the resistance arises from prevention of syncytia formation in infected cells.

Cells which are useful in characterizing sequences identified by the methods of this invention and their effects on cell-to-cell infection by HIV-1 are human T-cell lines which are permissive for infection with HIV-1, including, e.g., H9 and HUT78 cell lines, which are available from the ATCC.

For cell transfection assays, ICAM-1 (or ICAM-2 or ICAM-3) cDNA (or any cDNA identified by the methods described herein) can be cloned into an appropriate expression vector. To obtain maximal expression, the cloned ICAM-1 (or ICAM-2 or ICAM-3) coding region is operably linked to a promoter which is active in human T cells, such as, for example, an IL-2 promoter. Alternatively, an ICAM-1 (or ICAM-2 or ICAM-3) cDNA can be placed under transcriptional control of a strong constitutive promoter, or an inducible promoter. Expression systems are well known in the art, as are methods for introducing an expression vector into cells. For example, an expression vector comprising an ICAM-1 (or ICAM-2 or ICAM-3) cDNA can be introduced into cells by DEAE-dextran or by electroporation, or any other known method. The cloned ICAM-1 (or ICAM-2 or ICAM-3) molecule is then expressed on the surface of the cell. Determination of whether an ICAM-1 (or ICAM-2 or ICAM-3) cDNA is expressed on the cell surface can be accomplished using antibody(ies) specific for ICAM-1 (or ICAM-2 or ICAM-3). In the case of chimpanzee ICAM-1 (or ICAM-2 or ICAM-3) expressed on the surface of human T cells, an antibody which distinguishes between chimpanzee and human ICAM-1 (or ICAM-2 or ICAM-3) can be used. This antibody can be labeled with a detectable label, such as a fluorescent dye. Cells expressing chimpanzee ICAM-1 (or ICAM-2 or ICAM-3) on their surfaces can be detected using fluorescence-activated cell sorting and the anti-ICAM-1 (or ICAM-2 or ICAM-3) antibody appropriately labeled, using well-established techniques.

Transfected human cells expressing chimpanzee ICAM-1 (or ICAM-2 or ICAM-3) on their cell surface can then be tested for syncytia formation, and/or for HIV replication, and/or for number of cells infected as an index of cell-to-cell infectivity. The chimpanzee ICAM-1 (or ICAM-2 or ICAM-3)-expressing cells can be infected with HIV-1 at an appropriate dose, for example tissue culture infectious dose 50, i.e., a dose which can infect 50% of the cells. Cells can be plated at a density of about $5\times10^5$ cells/ml in appropriate tissue culture medium, and, after infection, monitored for syncytia formation, and/or viral replication, and/or number of infected cells in comparison to control, uninfected cells. Cells which have not been transfected with chimpanzee ICAM-1 (or ICAM-2 or ICAM-3) also serve as controls. Syncytia formation is generally observed in HIV-1-infected cells (which are not expressing chimpanzee ICAM-1 (or ICAM-2 or ICAM-3)) approximately 10 days post-infection.

To monitor HIV replication, cell supernatants can be assayed for the presence and amount of p24 antigen. Any assay method to detect p24 can be used, including, for example, an ELISA assay in which rabbit anti-p24 antibodies are used as capture antibody, biotinylated rabbit anti-p24 antibodies serve as detection antibody, and the assay is developed with avidin-horse radish peroxidase. To determine the number of infected cells, any known method, including indirect immunofluorescence methods, can be used. In indirect immunofluorescence methods, human HIV-positive serum can be used as a source of anti-HIV antibodies to bind to infected cells. The bound antibodies can be detected using FITC-conjugated anti-human IgG, the cells visualized by fluorescence microscopy and counted.

Another method for assessing the role of a molecule such as ICAM-1 (or ICAM-2 or ICAM-3) involves successive infection of cells with HIV. Human cell lines, preferably those that do not express endogenous ICAM (although cell lines that do express endogenous ICAM may also be used), are transfected with either human or chimpanzee ICAM B1 or B2 or B3. In one set of experiments, HIV is collected from the supernatant of HIV-infected human ICAM-1 (or ICAM-2 or ICAM-3)-expressing cells and used to infect chimpanzee ICAM-1 (or ICAM-2 or ICAM-3)-expressing cells or human ICAM-1 (or ICAM-2 or ICAM-3)-expressing cells. Initial infectivity, measured as described above, of both the chimpanzee ICAM-1 (or ICAM-2 or ICAM-3)- and the human ICAM-1 (or ICAM-2 or ICAM-3)-expressing cells would be expected to be high. After several rounds of replication, cell to cell infectivity would be expected to decrease in the chimpanzee ICAM-1 (or ICAM-2 or ICAM-3) expressing cells, if chimpanzee ICAM-1 (or ICAM-2 or ICAM-3) confers resistance. In a second set of experiments. HIV is collected from the supernatant of HIV-infected chimpanzee ICAM-1 (or ICAM-2 or ICAM-3)-expressing cells, and used to infect human ICAM-1 (or ICAM-2 or ICAM-3)-expressing cells. In this case, the initial infectivity would be expected to be much lower than in the first set of experiments, if ICAM-1 (or ICAM-2 or ICAM-3) is involved in susceptibility to HIV progression. After several rounds of replication, the cell to cell infectivity would be expected to increase.

The identified human sequences can be used in establishing a database of candidate human genes that may be involved in conferring, or contributing to, AIDS susceptibility or resistance. Moreover, the database not only provides an ordered collection of candidate genes, it also provides the precise molecular sequence differences that exist between human and an AIDS-resistant non-human primate (such as chimpanzee) and thus defines the changes that underlie the functional differences.

Example 6

Molecular Modeling of ICAM-1 and ICAM-3

Modeling of the three-dimensional structure of ICAM-1 and ICAM-3 has provided additional evidence for the role of these proteins in explaining chimpanzee resistance to AIDS progression.

In the case of ICAM-1, 5 of the 6 amino acid replacements that are unique to the chimpanzee lineage are immediately adjacent (i.e., physically touching) to those amino acids identified by mutagenic studies as critical to LFA-1 binding. These five amino acid replacements are human L18 to chimp Q18, human K29 to chimp D29, human P45 to chimp G45, human R49 to chimp W49, and human E171 to chimp Q171. This positioning cannot be predicted from the primary structure (i.e., the actual sequence of amino acids). None of the amino acid residues critical for binding has changed in the chimpanzee ICAM-1 protein.

Such positioning argues strongly that the chimpanzee ICAM-1 protein=s basic function is unchanged between humans and chimpanzees; however, evolution has wrought fine-tuned changes that may help confer upon chimpanzees their resistance to progression of AIDS. The nature of the amino acid replacements is being examined to allow exploitation of the three-dimensional structural information for developing agents for therapeutic intervention. Strikingly, 4 of the 5 chimpanzee residues are adjacent to critical binding residues that have been identified as N-linked glycosylation sites. This suggests that differences exist in binding constants (to LFA-1) for human and chimpanzee ICAM-1. These binding constants are being determined. Should the binding constants prove lower in chimpanzee ICAM-1, it is possible to devise small molecule agents to mimic (by way of steric hindrance) the change in binding constants as a potential therapeutic strategy for HIV-infected humans. Similarly, stronger binding constants, if observed for chimpanzee ICAM-1, will suggest alternative strategies for developing therapeutic interventions for HIV-1 infected humans.

In the case of ICAM-3, a critical amino acid residue replacement from proline (observed in seven humans) to glutamine (observed in three chimpanzees) is predicted from our modeling studies to significantly change the positional angle between domains 2 and 3 of human and chimpanzee ICAM-3. The human protein displays an acute angle at this juncture. Klickstein, et al., 1996 J. Biol. Chem. 27:239 20-27. Loss of this sharp angle (bend) is predicted to render chimpanzee ICAM-3 less easily packaged into HIV-1 virions (In infected humans, after ICAMs are packaged into HIV virions, cell-to-cell infectivity dramatically increases. Barbeau, B. et al., 1998 J. Virol. 72:7125-7136). This failure to easily package chimp ICAM-3 into HIV virions could then prevent the increase in cell-to-cell infectivity seen in infected humans. This would then account for chimpanzee resistance to AIDS progression.

A small molecule therapeutic intervention whereby binding of a suitably-designed small molecule to the human proline residue causes (as a result of steric hindrance) the human ICAM-1 protein to mimic the larger (i.e., less-acute) angle of chimpanzee ICAM-3 is possible. Conservation between the 2 proteins of the critical binding residues (and the general resemblance of immune responses between humans and chimpanzees) argues that alteration of this angle will not compromise the basic function of human ICAM-3. However, the human ICAM-3 protein would be rendered resistant to packaging into HIV virions, thus mimicking (in HIV-1 infected humans) the postulated pathway by which infected chimpanzees resist progression to AIDS.

Essentially the same procedures were used to identify positively selected chimpanzee ICAM-2 and ICAM-3 (see Table 4). The ligand binding domain of ICAM-1 has been localized as exhibiting especially striking positive selection in contrast to ICAMs-2 and -3, for which positive selection resulted in amino acid replacements throughout the protein. Thus, this comparative genomic analysis reveals that positive selection on ICAMs in chimpanzees has altered the proteins= primary structure, for example, in important binding domains. These alterations may have conferred resistance to AIDS progression in chimpanzees.

TABLE 4

$K_A/K_S$ Ratios: ICAM-2 and 3 Whole Protein Comparisons

| Species Compared | $K_A/K_S$ Ratio |
| --- | --- |
| Chimpanzee to Human ICAM-2 | 2.1 ($P < 0.01$) |
| Chimpanzee to Human ICAM-3 | 3.7 ($P < 0.01$) |

Binding of ICAM-1, -2, and -3 has been demonstrated to play an essential role in the formation of syncytia (i.e., giant, multi-nucleated cells) in HIV-infected cells in vitro. Pantaleo et al. (1991) J. Ex. Med. 173:511-514. Syncytia formation is followed by the depletion of $CD^+$ cells in vitro. Pantaleo et al. (1991); Levy (1993) Microbiol. Rev. 57:183-189; Butini et al. (1994) Eur. J. Immunol. 24:2191-2195; Finkel and Banda (1994) Curr. Opin. Immunol. 6:605-615. Although syncytia formation is difficult to detect in vivo, clusters of infected cells are seen in lymph nodes of infected individuals. Pantaleo et al., (1993) N. Eng. J. Med. 328:327-335; Finkel and Banda (1994); Embretson et al. (1993) *Nature* 362:359-362; Pantaleo et al. (1993) *Nature* 362:355-358. Syncytia may simply be scavenged from the body too quickly to be detected. Fouchier et al. (1996) *Virology* 219:87-95. Syncytia-mediated loss of CD4+ cells in vivo has been speculated to occur; this could contribute directly to compromise of the immune system, leading to opportunistic infection and full-blown AIDS. Sodrosky et al. (1986) *Nature* 322:470-474; Hildreth and Orentas (1989) *Science* 244:1075-1078; Finkel and Banda (1994). Thus critical changes in chimpanzee ICAM-1, ICAM-2 or ICAM-3 may deter syncytia formation in chimpanzee and help explain chimpanzee resistance to AIDS progression. Because of the polyfunctional nature of ICAMs, these positively selected changes in the ICAM genes may additionally confer resistance to other infectious diseases or may play a role in other inflammatory processes that may also be of value in the development of human therapeutics. The polypeptide sequence alignments of ICAM-1, -2, and -3 are shown in FIGS. 5, 6, and 7, respectively.

Example 7

Identifying Positive Selection of MIP-1α

MIP-1α is a chemokine that has been shown to suppress HIV-1 replication in human cells in vitro (Cocchi, F. et al., 1995 Science 270:1811-1815). The chimpanzee homologue of the human MIP-1α gene was PCR-amplified and sequenced. Calculation of the $K_A/K_S$ ratio (2.1, P<0.05) and comparison to the gorilla homologue reveals that the chimpanzee gene has been positively-selected. As for the other genes discussed herein, the nature of the chimpanzee amino acid replacements is being examined to determine how to exploit the chimpanzee protein for therapeutic intervention.

Example 8

Identifying Positive Selection of 17-β-Hydroxysteroid Dehydrogenase

Using the methods of the present invention, a chimpanzee gene expressed in brain has been positively-selected ($K_A/K_S=1.6$) as compared to its human homologue (GenBank Acc. #X87176) has been identified. The human gene, 17-β hydroxysteroid dehydrogenase type IV, codes for a protein known to degrade the two most potent estrogens, β-estradiol, and 5-diol (Adamski. J. et al. 1995 *Biochem J.* 311:437-443). Estrogen-related cancers (including, for example, breast and prostate cancers) account for some 40% of human cancers. Interestingly, reports in the literature suggest that chimpanzees are resistant to tumorigenesis, especially those that are estrogen-related. This protein may have been positively-selected in chimpanzees to allow more efficient degradation of estrogens, thus conferring upon chimpanzees resistance to such cancers. If so, the specific amino acid replacements observed in the chimpanzee protein may supply important information for therapeutic intervention in human cancers.

Example 9 cDNA Library Construction for Chimpanzee Brain Tissue

A chimpanzee brain cDNA library is constructed using chimpanzee brain tissue. The chimpanzee brain tissue can be obtained after natural death so that no killing of an animal is necessary for this study. In order to increase the chance of obtaining intact mRNAs expressed in brain, however, the brain is obtained as soon as possible after the animal=s death. Preferably, the weight and age of the animal are determined prior to death. The brain tissue used for constructing a cDNA library is preferably the whole brain in order to maximize the inclusion of mRNA expressed in the entire brain. Brain tissue is dissected from the animal following standard surgical procedures.

Total RNA is extracted from the brain tissue and the integrity and purity of the RNA are determined according to conventional molecular cloning methods. Poly A+ RNA is selected and used as template for the reverse-transcription of cDNA with oligo (dT) as a primer. The synthesized cDNA is treated and modified for cloning using commercially available kits. Recombinants are then packaged and propagated in a host cell line. Portions of the packaging mixes are amplified and the remainder retained prior to amplification. The library can be normalized and the numbers of independent recombinants in the library is determined.

Example 10

Sequence Comparison of Chimpanzee and Human Brain cDNA

Randomly selected chimpanzee brain cDNA clones from the cDNA library are sequenced using an automated sequencer, such as the ABI 377. Commonly used primers on the cloning vector such as the M13 Universal and Reverse primers are used to carry out the sequencing. For inserts that are not completely sequenced by end sequencing, dye-labeled terminators are used to fill in remaining gaps.

The resulting chimpanzee sequences are compared to human sequences via database searches, e.g., BLAST searches. The high scoring "hits," i.e., sequences that show a significant (e.g., >80%) similarity after BLAST analysis, are retrieved and analyzed. The two homologous sequences are then aligned using the alignment program CLUSTAL V developed by Higgins et al. Any sequence divergence, including nucleotide substitution, insertion and deletion, can be detected and recorded by the alignment.

The detected sequence differences are initially checked for accuracy by finding the points where there are differences between the chimpanzee and human sequences; checking the sequence fluorogram (chromatogram) to determine if the bases that appear unique to human correspond to strong, clear signals specific for the called base; checking the human hits to see if there is more than one human sequence that corresponds to a sequence change; and other methods known in the art as needed. Multiple human sequence entries for the same gene that have the same nucleotide at a position where there is a different chimpanzee nucleotide provides independent support that the human sequence is accurate, and that the chimpanzee/human difference is real. Such changes are examined using public database information and the genetic code to determine whether these DNA sequence changes result in a change in the amino acid sequence of the encoded protein. The sequences can also be examined by direct sequencing of the encoded protein.

Example 11

Molecular Evolution Analysis of Human Brain Sequences Relative to Other Primates The chimpanzee and human sequences under comparison are subjected to $K_A/K_S$ analysis. In this analysis, publicly available computer programs, such as Li 93 and INA, are used to determine the number of non-synonymous changes per site ($K_A$) divided by the number of synonymous changes per site ($K_S$) for each sequence under study as described above. This ratio, $K_A/K_S$, has been shown to be a reflection of the degree to which adaptive evolution, i.e., positive selection, has been at work in the sequence under study. Typically, full-length coding regions have been used in these comparative analyses. However, partial segments of a coding region can also be used effectively. The higher the $K_A/K_S$ ratio, the more likely that a sequence has undergone adaptive evolution. Statistical significance of $K_A/K_S$ values is determined using established statistic methods and available programs such as the t-test. Those genes showing statistically high $K_A/K_S$ ratios between chimpanzee and human genes are very likely to have undergone adaptive evolution.

To further lend support to the significance of a high $K_A/K_S$ ratio, the sequence under study can be compared in other non-human primates, e.g., gorilla, orangutan, bonobo. These comparisons allow further discrimination as to whether the adaptive evolutionary changes are unique to the human lineage compared to other non-human primates. The sequences can also be examined by direct sequencing of the gene of interest from representatives of several diverse human populations to assess to what degree the sequence is conserved in the human species.

Example 12

Further Sequence Characterization of Selected Human Brain Sequences

Human brain nucleotide sequences containing evolutionarily significant changes are further characterized in terms of their molecular and genetic properties, as well as their biological functions. The identified coding sequences are used as probes to perform in situ mRNA hybridization that reveals the expression pattern of the gene, either or both in terms of what tissues and cell types in which the sequences are expressed, and when they are expressed during the course of development or during the cell cycle. Sequences that are expressed in brain may be better candidates as being associated with important human brain functions. Moreover, the putative gene with the identified sequences are subjected to homologue searching in order to determine what functional classes the sequences belong to.

Furthermore, for some proteins, the identified human sequence changes may be useful in estimating the functional consequence of the change. By using such criteria a database of candidate genes can be generated. Candidates are ranked as to the likelihood that the gene is responsible for the unique or enhanced abilities found in the human brain compared to chimpanzee or other non-human primates, such as high capacity information processing, storage and retrieval capabilities, language abilities, as well as others. In this way, this approach provides a new strategy by which such genes can be identified. Lastly, the database not only provides an ordered collection of candidate genes, it also provides the precise molecular sequence differences that exist between human and chimpanzee (and other non-human primates), and thus defines the changes that underlie the functional differences.

In some cases functional differences are evaluated in suitable model systems, including, but not limited to, in vitro analysis such as indicia of long term potentiation (LTP), and use of transgenic animals or other suitable model systems. These will be immediately apparent to those skilled in the art.

Example 13

Identification of Positive Selection in a Human Tyrosine Kinase Gene

Using the methods of the present invention, a human gene (GenBank Acc. #AB014541), expressed in brain has been identified, that has been positively-selected as compared to its gorilla homologue. This gene, which codes for a tyrosine kinase, is homologous to a well-characterized mouse gene (GenBank Acc. #AF011908) whose gene product, called AATYK, is known to trigger apoptosis (Gaozza, E. et al. 1997 *Oncogene* 15:3127-3135). The literature suggests that this protein controls apoptosis in the developing mouse brain (thus, in effect, "sculpting" the developing brain). The AATYK-induced apoptosis that occurs during brain development has been demonstrated to be necessary for normal brain development.

There is increasing evidence that inappropriate apoptosis contributes to the pathology of human neurodegenerative diseases, including retinal degeneration, Huntington's disease, Alzheimer's disease, Parkinson's disease and spinal muscular atrophy, an inherited childhood motoneuron disease. On the other hand in neural tumour cells, such as neuroblastoma and medulloblastoma cells, apoptotic pathways may be disabled and the cells become resistant to chemotherapeutic drugs that kill cancer cells by inducing apoptosis. A further understanding of apoptosis pathways and the function of apoptosis genes should lead to a better understanding of these conditions and permit the use of AATYKI in diagnosis of such conditions.

Positively-selected human and chimpanzee AATYK may constitute another adaptive change that has implications for disease progression. Upon resolution of the three-dimensional structure of human and chimpanzee AATYK, it may be possible to design drugs to modulate the function of AATYK in a desired manner without disrupting any of the normal functions of human AATTK.

It has been demonstrated that mouse AATYK is an active, non-receptor, cytosolic kinase which induces neuronal differentiation in human adrenergic neuroblastoma (NB):SH-SY5Y cells. AATYK also promotes differentiation induced by other agents, including all-trans retinoic acid (RA), 12-O-Tetradecanoyl phorbol 13-acetate (TPA) and IGF-I. Raghunath, et al., *Brain Res Mol Brain Res*. (2000) 77:151-62. In experiments with rats, it was found that the AATYK protein was expressed in virtually all regions of the adult rat brain in which neurons are present, including olfactory bulb, forebrain, cortex, midbrain, cerebellum and pons. Immunohistochemical labeling of adult brain sections showed the highest levels of AATYK expression in the cerebellum and olfactory bulb. Expression of AATYK was also up-regulated as a function of retinoic acid-induced neuronal differentiation of p19 embryonal carcinoma cells, supporting a role for this protein in mature neurons and neuronal differentiation. Baker, et al., *Oncogene* (2001) 20:1015-21.

Nicolini, et al., *Anticancer Res* (1998) 18:2477-81 showed that retinoic acid (RA) differentiated SH-SY5Y cells were a suitable and reliable model to test the neurotoxicity of chemotherapeutic drugs without the confusing effects of the neurotrophic factors commonly used to induce neuronal differentiation. The neurotoxic effect and the course of the changes is similar to that observed in clinical practice and in in vivo experimental models. Thus, the model is proposed as a screening method to test the neurotoxicity of chemotherapy drugs and the possible effect of neuroprotectant molecules and drugs. Similarly, AATYK differentiated SYSY-5Y cells could be used as a model for screening chemotherapeutic drugs and possible side effects of neuroprotectant molecules and drugs.

It has also been shown that AATYK mRNA is expressed in neurons throughout the adult mouse brain. AATYK possessed tyrosine kinase activity and was autophosphorylated when expressed in 293 cells. AATYK mRNA expression was rapidly induced in cultured mouse cerebellar granule cells during apoptosis induced by KCl. The number of apoptotic granule cells overexpressing wild-type AATYK protein was significantly greater than the number of apoptotic granule cells overexpressing a mutant AATYK that lacked tyrosine kinase activity. These findings suggest that through its tyrosine kinase activity, AATYK is also involved in the apoptosis of mature neurons. Tomomura, et al., *Oncogene* (2001) 20(9):1022-32.

The tyrosine kinase domain of AATYK protein is highly conserved between mouse, chimpanzee, and human (as are most tyrosine kinases). Interestingly, however, the region of the protein to which signaling proteins bind has been positively-selected in humans, but strongly conserved in both chimpanzees and mice. The region of the human protein to which signaling proteins bind has not only been positively-selected as a result of point nucleotide mutations, but additionally displays duplication of several src homology 2 (SH2) binding domains that exist only as single copies in mouse and chimpanzee. This suggests that a different set of signaling proteins may bind to the human protein, which could then trigger different pathways for apoptosis in the developing human brain compared to those in mice and chimpanzees. Such a gene thus may contribute to unique or enhanced human cognitive abilities. Fluman AATYK has been mapped on 25.3 region of chromosome 17. Seki, et al., *J Hum Genet* (1999) 44:141-2.

Chimpanzee DNA was sequenced as part of a high-throughput sequencing project on a MegaBACE 1000 sequencer (AP Biotech). DNA sequences were used as query sequences in a BLAST search of the GenBank database. Two random chimpanzee sequences, termed stch856 and stch610, returned results for two genes in the non-redundant database of GenBank: NM_004920 (human apoptosis-associated tyrosine kinase, AATYK) and AB014541 (human KIAA641, identical nucleotide sequence to NM_004920), shown in FIG. 14A, and also showed a high $K_A/K_S$ ratio compared to these human sequences. Primers were designed for PCR and sequencing of AATYK. Sequence was obtained for the 3 prime end of this gene in chimp and gorilla. The 5 prime end of the gene was difficult to amplify, and no sequence was confirmed in human and gorilla. The human AATYK gene (SEQ ID NO:14) has a coding region of 3624 bp (nucleotides 413-4036 of SEQ ID NO:14), and codes for a protein of 1207 amino acids (SEQ ID NO:16). 1809 bp were sequenced in both chimp and gorilla. See FIGS. 15A and 15B. The partial sequences (SEQ ID NO:17 and SEQ ID NO:18) did not include the start or stop codons, although they were very close to the stop codon on the 3 prime end (21 codons away). These sequences correspond to nucleotides 2170-3976 or 2179-3988 of the corresponding human sequences taking into account the gaps described below.

There were also several pairs of amino acid insertions/deletions among chimp, human and gorilla in the coding region. The following sequences are in reading frame:

```
Chimp         GGTGAGGGCCCCGGCCCCGGGCCC        (SEQ ID NO:19)
Human    2819 GGTGAGGGC::::::CCCGGGCCC 2836   (SEQ ID NO:20)
Gorilla       GGCGAGGGC::::::CCCGGGCCC        (SEQ ID NO:21)

Chimp         CTGGAGGCTGAGGCCGAGGCCGAG        (SEQ ID NO:22)
Human    2912 CTCGAGGCT::::::GAGGCCGAG 2929   (SEQ ID NO:23)
Gorilla       CTGGAGGCT::::::GAGGCCGAG        (SEQ ID NO:24)

Chimp         CCCACGCCC::::::GCTCCCTTC        (SEQ ID NO:25)
Human    3890 CCCACGCCCACGCCCGCTCCCTTC 3913   (SEQ ID NO:26)
Gorilla       CCCACGCCC::::::GCTCCCTTC        (SEQ ID NO:27)

Chimp         CCCACGTCCACGTCCCGCTTCTCC        (SEQ ID NO:28)
Human    3938 CCCACGTCC::::::CGCTTCTCC 3955   (SEQ ID NO:29)
Gorilla       CCCACGTCC::::::CGCTTCTCC        (SEQ ID NO:30)
```

Each of these insertions/deletions affected two amino acids and did not change the reading frame of the sequence. Sliding window $KA/K_S$ for chimp to human, chimp to gorilla, and human to gorilla, excluding the insertion/deletion regions noted above, showed a high Ka/Ks ratio for some areas. See Table 9.

The highest Ka/Ks ratios are human to gorilla and chimp to gorilla, suggesting that both the human and chimp gene have undergone selection, and is consistent with the idea that the two species share some enhanced cognitive abilities relative to the other great apes (gorillas, for example). Such data bolsters the view that this gene may play a role with regard to enhanced cognitive functions. It should also be noted that in general, the human-containing pairwise comparisons are higher than the analogous chimp-containing comparisons.

TABLE 9

$K_A/K_S$ ratios for various windows of AATYK on chimp, human, and gorilla

| AATYK | | $K_A$ | $K_S$ | $K_A/K_S$ | $K_A$ SE | $K_S$ SE | size bp | bp of partial CDS | t | bp of NM 004920 (pub human AATYK) |
|---|---|---|---|---|---|---|---|---|---|---|
| chimp | gorilla | 0.02287 | 0.03243 | 0.705211 | 0.00433 | 0.00832 | 1809 | 1-1809 | 1.019266 | 2180-3988 |
| chimp | human | 0.01538 | 0.01989 | 0.773253 | 0.00366 | 0.0062 | 1809 | 1-1809 | 0.626415 | 2180-3988 |
| human | gorilla | 0.02223 | 0.03204 | 0.69382 | 0.00429 | 0.00848 | 1809 | 1-1809 | 1.032263 | 2180-3988 |
| ch1 | hu1 | 0.03126 | 0.02009 | 1.555998 | 0.01834 | 0.02034 | 150 | 1-150 | 0.407851 | 2180-2329 |

TABLE 9-continued $K_A/K_S$ ratios for various windows of AATYK on chimp, human, and gorilla

| AATYK | | $K_A$ | $K_s$ | $K_A/K_S$ | $K_A$ SE | $K_S$ SE | size bp | bp of partial CDS | t | bp of NM 004920 (pub human AATYK) |
|---|---|---|---|---|---|---|---|---|---|---|
| ch2 | hu2 | 0.03142 | 0.04043 | 0.777146 | 0.01844 | 0.02919 | 150 | 100-249 | 0.260958 | 2279-2428 |
| ch3 | hu3 | 0.02073 | 0.02036 | 1.018173 | 0.01481 | 0.02087 | 150 | 202-351 | 0.014458 | 2381-2530 |
| ch4 | hu4 | 0.02733 | 0.02833 | 0.964702 | 0.01753 | 0.02383 | 150 | 301-450 | 0.033803 | 2480-2629 |
| ch5 | hu5 | 0 | 0.05152 | 0 | 0 | 0.03802 | 150 | 400-549 | 1.355076 | 2579-2728 |
| ch6 | hu6 | 0.00836 | 0.03904 | 0.214139 | 0.00838 | 0.03964 | 150 | 502-651 | 0.75723 | 2681-2830 |
| ch7 | hu7 | 0.00888 | 0.05893 | 0.150687 | 0.0089 | 0.0439 | 150 | 601-750 | 1.11736 | 2780-2929 |
| ch8 | hu8 | 0.02223 | 0.03829 | 0.580569 | 0.01589 | 0.03886 | 150 | 700-849 | 0.382534 | 2879-3028 |
| ch9 | hu9 | 0.04264 | 0.03644 | 1.170143 | 0.02173 | 0.02628 | 150 | 799-948 | 0.181817 | 2978-3127 |
| ch10 | hu10 | 0.02186 | 0.01823 | 1.199122 | 0.01563 | 0.01851 | 150 | 901-1050 | 0.149837 | 3080-3229 |
| ch11 | hu11 | 0.01087 | 0 | #DIV/0! | 0.01093 | 0 | 150 | 1000-1149 | 0.994511 | 3179-3328 |
| ch12 | hu12 | 0.01093 | 0 | #DIV/0! | 0.01099 | 0 | 150 | 1099-1248 | 0.99454 | 3278-3427 |
| ch13 | hu13 | 0.01031 | 0 | #DIV/0! | 0.01036 | 0 | 150 | 1201-1350 | 0.995174 | 3380-3529 |
| ch14 | hu14 | 0.01053 | 0 | #DIV/0! | 0.01058 | 0 | 150 | 1300-1449 | 0.995274 | 3479-3628 |
| ch15 | hu15 | 0.01835 | 0.02006 | 0.914756 | 0.01315 | 0.02057 | 150 | 1399-1548 | 0.070042 | 3578-3727 |
| ch16 | hu16 | 0 | 0.02027 | 0 | 0 | 0.02062 | 150 | 1501-1650 | 0.983026 | 3680-3829 |
| ch17 | hu17 | 0.00666 | 0 | #DIV/0! | 0.00667 | 0 | 210 | 1600-1809 | 0.998501 | 3779-3988 |
| chA | huA | 0.02366 | 0.02618 | 0.903743 | 0.00875 | 0.01251 | 501 | 1-501 | 0.165069 | 2180-2680 |
| chB | huB | 0.01159 | 0.03863 | 0.300026 | 0.00585 | 0.01811 | 501 | 400-900 | 1.420809 | 2579-3079 |
| chC | huC | 0.02212 | 0.0108 | 2.048148 | 0.00846 | 0.00768 | 501 | 799-1299 | 0.990721 | 2978-3478 |
| chD | huD | 0.00851 | 0.00734 | 1.159401 | 0.00458 | 0.00602 | 609 | 1201-1809 | 0.154676 | 3380-3988 |
| chA | gorA | 0.02082 | 0.04868 | 0.427691 | 0.00795 | 0.0191 | 501 | 1-501 | 1.346644 | 2180-2680 |
| chB | gorB | 0.01416 | 0.04039 | 0.350582 | 0.00639 | 0.0172 | 501 | 400-900 | 1.429535 | 2579-3079 |
| chC | gorC | 0.01737 | 0.00538 | 3.228625 | 0.00717 | 0.00542 | 501 | 799-1299 | 1.333991 | 2978-3478 |
| chD | gorD | 0.00644 | 0.00244 | 2.639344 | 0.00408 | 0.00346 | 609 | 1201-1809 | 0.747722 | 3380-3988 |
| huA | gorA | 0.02246 | 0.02759 | 0.814063 | 0.00829 | 0.01523 | 501 | 1-501 | 0.295847 | 2180-2680 |
| huB | gorB | 0.01418 | 0.06809 | 0.208254 | 0.0064 | 0.02388 | 501 | 400-900 | 2.180583 | 2579-3079 |
| huC | gorC | 0.01993 | 0.00541 | 3.683919 | 0.00762 | 0.00544 | 501 | 799-1299 | 1.550854 | 2978-3478 |
| huD | gorD | 0.00723 | 0.00488 | 1.481557 | 0.0042 | 0.0049 | 609 | 1201-1809 | 0.364133 | 3380-3988 |

Example 14

Positively Selected Human BRCA1 Gene

Comparative evolutionary analysis of the BRCA1 genes of several primate species has revealed that the human BRCA1 gene has been subjected to positive selection. Initially, 1141 codons of exon 11 of the human and chimpanzee BRCA1 genes (Hacia et al. (1998) *Nature Genetics* 18:155-158) were compared and a strikingly high $K_A/K_S$ ratio, 3.6, was found when calculated by the method of Li (Li (1993) *J. Mol. Evol.* 36:96-99; Li et al. (1985) *Mol. Biol. Evol.* 2:150-174). In fact, statistically significant elevated ratios were obtained for this comparison regardless of the particular algorithm used (see Table 5A). Few genes (or portions of genes) have been documented to display ratios of this magnitude (Messier et al. (1997) *Nature* 385:151-154; Endo et al. (1996) *Mol. Biol. Evol.* 13:685-690; and Sharp (1997) *Nature* 385:111-112). We thus chose to sequence the complete protein-coding region (5589 bp) of the chimpanzee BRCA1 gene, in order to compare it to the full-length protein-coding sequence of the human gene. In many cases, even when positive selection can be shown to have operated on limited regions of a particular gene, $K_A/K_S$ analysis of the full-length protein-coding sequence fails to reveal evidence of positive selection (Messier et al. (1997), supra). This is presumably because the signal of positive selection can be masked by noise when only small regions of a gene have been positively selected, unless selective pressures are especially strong. However, comparison of the full-length human and chimpanzee BRCA1 sequences still yielded $K_A/K_S$ ratios in excess of one, by all algorithms we employed (Table 5A). This suggests that the selective pressure on BRCA1 was intense. A sliding-window $K_A/K_S$ analysis was also performed, in which intervals of varying lengths (from 150 to 600 bp) were examined, in order to determine the pattern of selection within the human BRCA1 gene. This analysis suggests that positive selection seems to have been concentrated in exon 11.

TABLE 5A

Human-Chimpanzee $K_A/K_S$ Comparisons

| Method | $K_A/K_S$ (exon 11) | $K_A/K_S$ (full-length) |
|---|---|---|
| Li (1993) J. Mol. Evol. 36: 96; Li et al. (1985) Mol. Biol. Evol. 2: 150 | 3.6*** | 2.3* |
| Ina Y. (1995) J. Mol. Evol. 40: 190 | 3.3** | 2.1* |
| Kumar et al., MEGA: Mol. Evol. Gen. Anal. (PA St. Univ, 1993) | 2.2* | 1.2 |

TABLE 5B $K_A/K_S$ for Exon 11 of BRCA1 from Additional Primates

| Comparison | | $K_A$ | $K_S$ | $K_A/K_S$ |
|---|---|---|---|---|
| Human | Chimpanzee | 0.010 | 0.003 | 3.6* |
| | Gorilla | 0.009 | 0.009 | 1.1 |
| | Orangutan | 0.018 | 0.020 | 0.9 |
| Chimpanzee | Gorilla | 0.006 | 0.007 | 0.8 |
| | Orangutan | 0.014 | 0.019 | 0.7 |
| Gorilla | Orangutan | 0.014 | 0.025 | 0.6 |

The Table 5B ratios were calculated according to Li (1993) *J. Mol. Evol.* 36:96; Li et al. (1985) *Mol. Biol. Evol.* 2:150. For all comparisons, statistical significance was calculated by t-tests, as suggested in Zhang et al. (1998) *Proc. Natl. Acad. Sci. USA* 95:3708. Statistically significant comparisons are indicated by one or more asterisks, with P values as follows: *, P<0.05, , P<0.01, *, P<0.005. Exon sequences are from Hacia et al. (1998) *Nature Genetics* 18:155. GenBank accession numbers: human, NM_000058.1, chimpanzee, AF019075, gorilla, AF019076, orangutan, AF019077, rhesus, AF019078.

Figure 9:
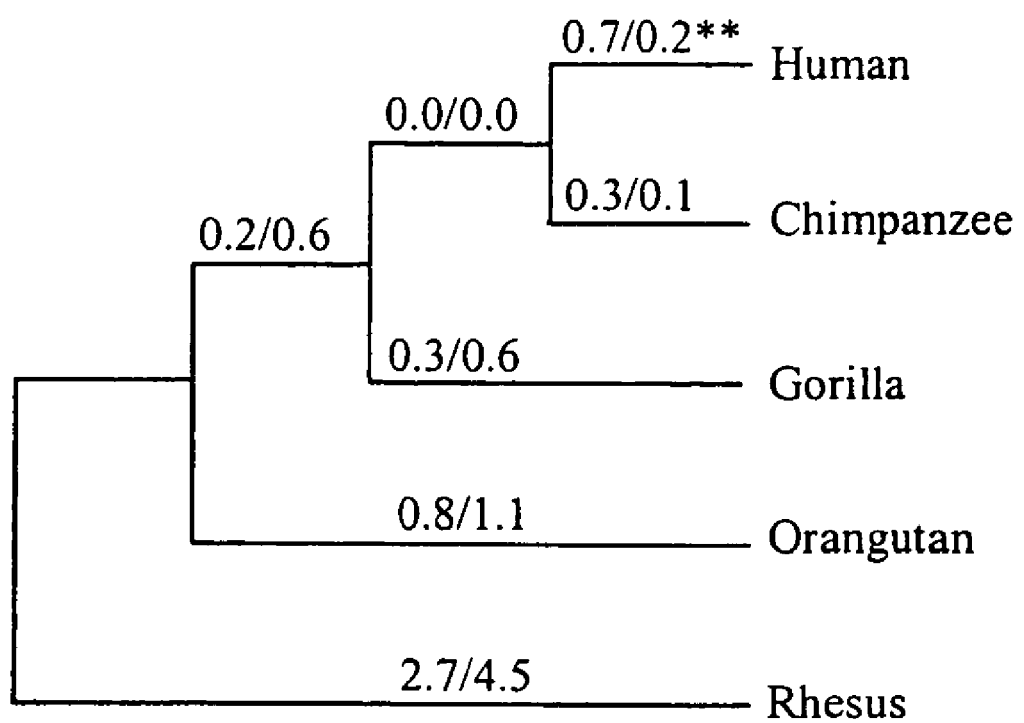
FIG. 9 illustrates the known phylogenetic tree for the species compared in Example 14, with values of $b_N$ and $b_S$ mapped upon appropriate branches. Values of $b_N$ and $b_S$ were calculated by the method described in Zhang et al. (1998) *Proc. Natl. Acad. Sci. USA* 95:3708-3713. Values are shown above the branches; all values are shown 100×, for reasons of clarity. Statistical significance was calculated as for comparisons in Table 5 (Example 14), and levels of statistical significance are as shown as in Table 5. Note that only the branch leading from the human/chimpanzee common ancestor to modern humans shows a statistically significant value for $b_N$-$b_S$.
Figure 10:
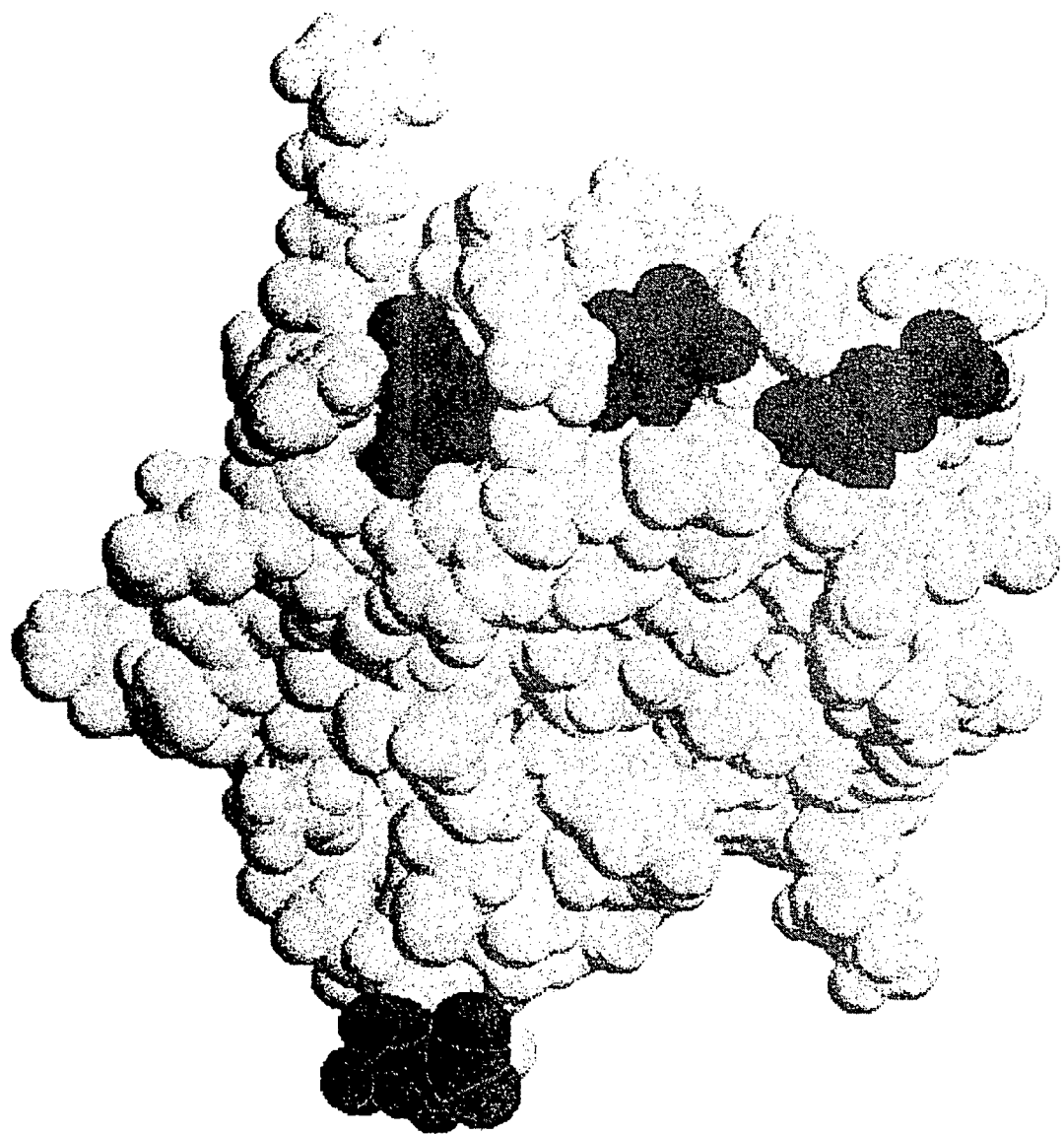
FIG. 10 illustrates a space-filling model of human CD59 with the duplicated GPI link (Asn) indicated by the darkest shading. This GPI link is duplicated in chimpanzees so that chimp CD59 contains 3 GPI links. The three areas of intermediate shading in FIG. 10 are other residues which differ between chimp and human.

The elevated $K_A/K_S$ ratios revealed by pairwise comparisons of the human and chimpanzee BRCA1 sequences demonstrate the action of positive selection, but such comparisons alone do not reveal which of the two genes compared, the human or the chimpanzee, has been positively selected. However, if the primate BRCA1 sequences are considered in a proper phylogenetic framework, only those pairwise comparisons which include the human gene show ratios greater than one, indicating that only the human gene has been positively selected (Table 5B). To confirm that positive selection operated on exon 11 of BRCA1 exclusively within the human lineage, the statistical test of positive selection proposed by Zhang et al. (1998) *Proc. Natl. Acad. Sci. USA* 95:3708-3713, was used. This test is especially appropriate when the number of nucleotides is large, as in the present case (3423 bp). This procedure first determines nonsynonymous nucleotide substitutions per nonsynonymous site ($b_N$) and synonymous substitutions per synonymous site ($b_S$) for each individual branch of a phylogenetic tree (Zhang et al. (1998), supra). Positive selection is supported only on those branches for which $b_N$-$b_S$ can be shown to be statistically significant (Zhang et al. (1998), supra). For BRCA1, this is true for only one branch of the primate tree shown in FIG. 9: the branch which leads from the human/chimpanzee common ancestor to modern humans, where $b_N/b_S$=3.6. Thus, we believe that in the case of the BRCA1 gene, positive selection operated directly and exclusively on the human lineage.

While it is formally possible that elevated $K_A/K_S$ ratios might reflect some locus or chromosomal-specific anomaly (such as suppression of $K_S$ due, for example, to isochoric differences in GC content), rather than the effects of positive selection, this is unlikely in the present case, for several reasons. First, the estimated $K_S$ values for the hominoid BRCA1 genes, including human, were compared to those previously estimated for other well-studied hominoid loci, including lysozyme (Messier et al. (1997), supra) and ECP (Zhang et al. (1998), supra). There is no evidence for a statistically significant difference in these values. This argues against some unusual suppression of $K_S$ in human BRCA1. Second, examination of GC content (Sueoka, N. in *Evolving Genes and Proteins* (eds. Bryson, V. & Vogel, H. J.) 479-496 (Academic Press, NY, 1964)) and codon usage patterns (Sharp et al. (1988) *Nucl. Acids Res.* 16:8207-8211) of the primate BRCA1 genes shows no significant differences from average mammalian values.

This demonstration of strong positive selection on the human BRCA1 gene constitutes the first molecular support for a theory long advanced by anthropologists. Human infants require, and receive, prolonged periods of post-birth care—longer than in any of our close primate relatives. Short, R. V. (1976) *Proc. R. Soc. Lond. B* 195:3-24, first postulated that human females can only furnish such extended care to human infants in the context of a long term pair bond with a male partner who provides assistance. The maintenance of long term pair bonds was strengthened by development of exaggerated (as compared to our close primate relatives) human secondary sex characteristics including enlarged female breasts (Short (1976), supra). Thus, strong selective pressures resulted in development of enlarged human breasts which develop prior to first pregnancy and lactation, contrary to the pattern seen in our hominoid relatives (Dixson, A. F. in *Primate Sexuality: Comparative Studies of the Prosimians, Monkeys, Apes and Human Beings.* 214 (Oxford Univ. Press, Oxford, 1998)).

Evidence suggests that in addition to its function as a tumor suppressor (Xu et al. (1999) *Mol. Cell* 3(3):389-395; Shen et al. (1998) *Oncogene* 17(24):3115-3124; Dennis, C. (1999) *Nature Genetics* 22:10; and Xu et al. (1999) *Nature Genetics* 22:37-43), the BRCA1 protein plays an important role in normal development of breast tissue (Dennis, C. (1999), supra; Xu et al. (1999) *Nature Genetics* 22:37-43; and Thompson et al. (1999) *Nature Genetics* 9:444-450), particularly attainment of typical mammary gland and duct size (Dennis, C. (1999), supra; and Xu et al. (1999) *Nature Genetics* 22:37-43). These facts suggest that positive selection on this gene in humans promoted expansion of the female human breast, and ultimately, helped promote long term care of dependent human infants. This long term dependency of human infants was essential for the development and transmission of complex human culture. Because positive selection seems to have been concentrated upon exon 11 of BRCA1, the prediction follows that the region of the BRCA1 protein encoded by exon 11 specifically plays a role in normal breast development. The data provided here suggests that strong selective pressures during human evolution led to amino acid replacements in BRCA1 that promoted a unique pattern of breast development in human females, which facilitated the evolution of some human behaviors.

Example 15

Characterization of BRCA1 Polynucleotide and Polypeptide

Having identified evolutionarily significant nucleotide changes in the BRCA1 gene and corresponding amino acid changes in the BRCA1 protein, the next step is to test these molecules in a suitable model system to analyze the functional effect of the nucleotide and amino acid changes on the model. For example, the human BRCA1 polynucleotide can be transfected into a cultured host cell such as adipocytes to determine its effect on cell growth or replication.

Example 16

Identification of Positively-Selected CD59

Comparative evolutionary analysis of the CD59 genes of several primate species has revealed that the chimpanzee CD59 gene has been subjected to positive selection. CD59 protein is also known as protectin, 1F-5Ag, H19, HRF20, MACIF, MIRL, and P-18. CD59 is expressed on all peripheral blood leukocytes and erythrocytes (Meri et al. (1996) *Biochem. J.* 316:923-935). Its function is to restrict lysis of human cells by complement (Meri et al. (1996), supra). More specifically, CD59 acts as one of the inhibitors of membrane attack complexes (MACs). MACs are complexes of 20 some complement proteins that make hole-like lesions in cell membranes (Meri et al. (1996), supra). These MACs, in the absence of proper restrictive elements (i.e., CD59 and a few other proteins) would destroy host cells as well as invading pathogens. Essentially then, CD59 protects the cells of the body from the complement arm of its own defense systems (Meri et al. (1996), supra). The chimpanzee homolog of this protein was examined because the human homolog has been implicated in progression to AIDS in infected individuals. It has been shown that CD59 is one of the host cell derived proteins that is selectively taken up by HIV virions (Frank et al. (1996) *AIDS* 10:1611-1620). Additionally, it has been shown (Saifuddin et al. (1995) *J. Exp. Med.* 182:501-509) that HIV virions which have incorporated host cell CD59 are protected from the action of complement. Thus it appears that in humans, HIV uses CD59 to protect itself from attack by the victim=s immune system, and thus to further the course of infection.

To obtain primate CD59 cDNA sequences, total RNA was prepared (using either the RNeasy® kit (Qiagen), or the RNAse-free Rapid Total RNA kit (5 Prime-3 Prime, Inc.)) from primate tissues (whole fresh blood from chimpanzees, gorillas, and orangutans). mRNA was isolated from total RNA using the Mini-Oligo(dT) Cellulose Spin Columns (5 Prime-3 Prime, Inc.). cDNA was synthesized from mRNA with oligo dT and/or random priming using the SuperScript Preamplification System for First Strand cDNA Synthesis (Gibco BRL). The protein-coding region of the primate CD59 gene was amplified from cDNA using primers (concentration=100 nmole/µl) designed from the published human sequence. PCR conditions for CD59 amplification were 94EC initial pre-melt (4 min), followed by 35 cycles of 94EC (15 sec), 58EC (1 min 15 sec), 72EC (1 min 15 sec), and a final 72EC extension for 10 minutes. PCR was accomplished on a Perkin-Elmer GeneAmp7 PCR System 9700 thermocycler, using Ready-to-Go PCR beads (Amersham Pharmacia Biotech) in a 50 µl total reaction volume. Appropriately-sized products were purified from agarose gels using the QiaQuick Gel Extraction kit (Qiagen). Both strands of the amplification products were sequenced directly using the Big Dye Cycle Sequencing Kit and analyzed on a 373A DNA sequencer (ABI BioSystems).

As shown in Table 6, all comparisons to the chimpanzee CD59 sequence display $K_A/K_S$ ratios greater than one, demonstrating that it is the chimpanzee CD59 gene that has been positively-selected.

TABLE 6

$K_A/K_S$ Ratios for Selected Primate CD59 cDNA Sequences

| Genes Compared | $K_A/K_S$ Ratios |
| --- | --- |
| Chimpanzee to Human | 1.8 |
| Chimpanzee to Gorilla | 1.5 |
| Chimpanzee to Orangutan | 2.3 |
| Chimpanzee to Green Monkey | 3.0 |

Example 17

Characterization of CD59 Positively-Selected Sequences

Proceeding on the hypothesis that strong selection pressure has resulted in adaptive changes in the chimpanzee CD59 molecule such that disease progression is retarded because the virus is unable to usurp CD59=s protective role for itself, it then follows that comparisons of the CD59 gene of other closely-related non-human primates to the human gene should display $K_A/K_S$ ratios less than one for those species that have not been confronted by the HIV-1 virus over evolutionary periods. Conversely, all comparisons to the chimpanzee gene should display $K_A/K_S$ ratios greater than one. These two tests, taken together, will definitively establish whether the chimpanzee or human gene was positively selected. Although the gorilla (*Gorilla gorilla*) is the closest relative to humans and chimpanzees, its postulated historical range in Africa suggests that gorillas could have been at some time exposed to the HIV-1 virus. We thus examined the CD59 gene from both the gorilla and the orangutan (*Pongo pyginaeus*). The latter species, confined to Southeast Asia, is unlikely to have been exposed to HIV over an evolutionary time frame. The nucleotide sequences of the human and orangutan genes were determined by direct sequencing of cDNAs prepared from RNA previously isolated from whole fresh blood taken from these two species.

The next step is to determine how chimpanzee CD59 contributes to chimpanzee resistance to progression to full-blown AIDS using assays of HIV replication in cell culture. Human white blood cell lines, transfected with, and expressing, the chimpanzee CD59 protein, should display reduced rates of viral replication (using standard assays familiar to practitioners of the art) as compared to control lines of untransfected human cells. In contrast, chimpanzee white blood cell lines expressing human CD59 should display increased viral loads as compared to control, untransfected chimpanzee cell lines.

Example 18

Molecular Modeling of CD59

Modeling of the inferred chimpanzee protein sequence of CD59 upon the known three-dimensional structure of human (Meri et al. 1996 *Biochem. J.* 316:923-935) has provided additional evidence for the role of this protein in explaining chimpanzee resistance to AIDS progression. It has been shown that in human CD59, residue Asn 77 is the link for the GPI anchor (Meri et al. (1996) *Biochem. J.* 316:923-935), which is essential for function of the protein. The GPI anchor is responsible for anchoring the protein to the cell membrane (Meri et al. (1996), supra). Our sequencing of the chimpanzee CD59 gene reveals that the inferred protein structure of chimpanzee CD59 contains a duplication of the section of the protein that contains the GPI link, i.e., NEQLENGG (see Table 7 and FIG. 10).

TABLE 7

Comparison of Human and Chimpanzee CD59 Amino Acid Sequence

| | | | | | |
|---|---|---|---|---|---|
| Human | SLQCYNCPNP | TADCKTAVNC | SSDFDACLIT | KAGLQVYNKC | (SEQ ID NO:12) |
| Chimpanzee | SLQCYNCPNP | TADCKTAVNC | SSDFDACLIT | KAGLQVYNKC | (SEQ ID NO:13) |

TABLE 7-continued Comparison of Human and Chimpanzee CD59 Amino Acid Sequence

| | | | | |
|---|---|---|---|---|
| Human | WK*F*EHCNF*ND* | *V*TTRLRENEL | TYYCCKKDLC | NFNEQLENGG |
| Chimpanzee | WK*L*EHCNF*KD* | *L*TTRLRENEL | TYYCCKKDLC | NFNEQLENGG |
| Human | ---------------- | TSLS | EKTVLL*L*VTP | PLAAAAWSLHP |
| Chimpanzee | *NEQLENGGNE* | *QLENGG*TSLS | EKTVLL*R*VTP | PLAAAAWSLHP |

Italics/underline indicates variation in amino acids.

This suggests that while the basic function of CD59 is most likely conserved between chimpanzee and human, some changes have probably occurred in the orientation of the protein with respect to the cell membrane. This may render the chimpanzee protein unusable to the HIV virion when it is incorporated by the virion. Alternatively, the chimpanzee protein may not be subject to incorporation by the HIV virion, in contrast to the human CD59. Either of these (testable) alternatives would likely mean that in the chimpanzee, HIV virions are subject to attack by MAC complexes. This would thus reduce amounts of virus available to replicate, and thus contribute to chimpanzee resistance to progression to full-blown AIDS. Once these alternatives have been tested to determine which is correct, then the information can be used to design a therapeutic intervention for infected humans that mimics the chimpanzee resistance to progression to full-blown AIDS.

Example 19

Identification of Positively-Selected DC-SIGN

Comparative evolutionary analyses of DC-SIGN genes of human, chimpanzee and gorilla have revealed that the chimpanzee DC-SIGN gene has been subjected to positive selection. FIGS. 11-13 (SEQ. ID. NOS. 6-8) show the nucleotide sequences of human, chimpanzee and gorilla DC-SIGN genes, respectively. Table 8 provides the $K_A/K_S$ values calculated by pairwise comparison of the human, chimpanzee and gorilla DC-SIGN genes. Note that only those comparisons with chimpanzee show $K_A/K_S$ values greater than one, indicating that the chimpanzee gene has been positively selected.

TABLE 8

$K_A/K_S$ Ratios for Selected Primate DC-SIGN cDNA Sequences

| Genes Compared | $K_A/K_S$ Ratios |
|---|---|
| Chimpanzee to Human | 1.3 |
| Human to Gorilla | 0.87 |
| Chimpanzee to Gorilla | 1.3 |

As discussed herein, DC-SIGN is expressed on dendritic cells and is known to provide a mechanism for transport of HIV-1 virus to the lymph nodes. HIV-1 binds to the extracellular portion of DC-SIGN and infects the undifferentiated T cells in the lymph nodes via their CD4 proteins. This expansion in infection ultimately leads to compromise of the immune system and subsequently to full-blown AIDS. Interestingly, DC-SIGNS's major ligand appears to be ICAM-3. As described herein, chimpanzee ICAM-3 shows the highest $K_A/K_S$ ratio of any known AIDS-related protein. It is not yet clear whether positive selection on chimpanzee ICAM-3 was a result of compensatory changes that allow ICAM-3 to retain its ability to bind to DC-SIGN.

Example 20

Detection of Positive Selection upon Chimpanzee p44

As is often true, whole protein comparisons for human and chimpanzee p44 display $K_A/K_S$ ratios less than one. This is because the accumulated "noise" of silent substitutions in the full-length CDS can obscure the signal of positive selection if it has occurred in a small section of the protein. However, examination of exon 2 of the chimpanzee and human homologs reveals that this portion of the gene (and the polypeptide it codes for) has been positively selected. The $K_A/K_S$ ratio for exon 2 is 1.5 (P<0.05). Use of this invention allowed identification of the specific region of the protein that has been positively selected.

Two alleles of p44 were detected in chimpanzees that differ by a single synonymous substitution (see FIG. 16). For human to chimpanzee, the whole protein $K_A/K_S$ ratio for allele A is 0.42, while the ratio for allele B is 0.45.

In FIG. 16, the CDS of human (Acc. NM_006417) and chimpanzee (Acc. D90034) p44 gene are aligned, with the positively selected exon 2 underlined (note that exon 2 begins at the start of the CDS, as exon 1 is non-coding.). Human is labeled Hs (Homo sapiens), chimpanzee is labeled Pt (*Pan troglodytes*). Nonsynonymous differences between the two sequences are in bold, synonymous differences are in italics. Chimpanzee has a single heterozygous base (position 212), shown as "M", using the IUPAC code to signify either adenine ("A") or cytosine ("C"). Note that one of these ("C") represents a nonsynonymous difference from human, while "A" is identical to the same position in the human homolog. Thus these two chimpanzee alleles differ slightly in their $K_A/K_S$ ratios relative to human p44.

Example 21

Methods for Screening Agents that May be Useful in Treatment of HCV in Humans

Candidate agents can be screened in vitro for interaction with purified p44, especially exon 2. Candidate agents can be designed to interact with human p44 exon 2 so that human p44 can mimic the structure and/or function of chimpanzee p44. Human and chimpanzee p44 are known and can be synthesized using methods known in the art.

Molecular modeling of small molecules to dock with their targets, computer assisted new lead design, and computer assisted drug discovery are well known in the art and are described, e.g., in Cohen, N. C. (ed.) Guidebook on Molecular Modeling in Drug Design, Academic Press (1996). Additionally, there are numerous commercially available molecular modeling software packages.

Affinity chromatography can be used to partition candidate agents that bind in vitro to human p44 (especially exon 2)

from those that do not. It may also be useful to partition candidate agents that no only bind to human p44 exon 2, but also do not bind to chimpanzee p44 exon 2, so as to eliminate those agents that are not specific to the human p44 exon 2.

Optionally, x-ray crystallography structures of p44-agent complexes can be compared to x-ray structures of human p44 and chimpanzee p44 to determine if the human p44-agent complexes more closely resemble x-ray structures of chimpanzee p44 structures.

Further, candidate agents can be screened for favorable interactions with p44 during HCV infection of hepatocytes in vitro. Fournier et al. (1998) J. Gen. Virol. 79:2367 report that adult normal human hepatocytes in primary culture can be successfully infected with HCV and used as an in vitro HCV model (see also Rumin et al. (1999) J. Gen. Virology 80:3007). Favre et al. (2001) CR Acad. Sci. III 324(12):1141-8, report that a robust in vitro infection of hepatocytes with HCV is facilitated by removal of cell-bound lipoproteins prior to addition of viral inocula from human sera. Further, Kitamura et al. (1994) Eur. J. Biochem. 224:877-83, report that IFNα/β induces human p44 gene in hepatocytes in vitro. The p44 protein is produced in vivo in infected human livers (Patzwahl, R. et al. (2000) J. Virology 75(3):1332). While it is presently not clear if p44 is produced by human hepatocytes in vitro during HCV infection, if it is not, IFNα/β could be added to induce p44. This in vitro system could serve as a suitable model for screening candidate agents for their capacity to favorably interact with human p44 in HCV infected hepatocytes.

An assay for favorable interaction of candidate agents with p44 in in vitro cultured cells could be the enhancement of p44 assembly into microtubules in the cultured hepatocytes. Assembled chimpanzee p44 microtubular aggregates associated with NANB hepatitis infection in chimpanzees have been detected by antibodies described in Takahashi, K. et al. (1990) J. Gen. Virology 71 (Pt9):2005-1 1. These antibodies may be useful in detecting human p44 microtubular aggregates. Alternatively, antibodies to human p44 can be made using methods known in the art.

A direct link between enhanced p44 microtubular assembly and increased resistance to HCV infection in chimpanzees or humans is not known at this time. However, the literature does indicate that increased p44 microtubular assembly is associated with HCV infection in chimpanzees, and chimpanzees are able to resist HCV infection. Specifically, Patzwahl, R. et al. (2000) J. Virology 75:1332-38, reports that p44 is a "component of the double-walled membranous tubules which appear as a distinctive alteration in the cytoplasm of hepatocytes after intravenous administration of human non-A, non-B (NANB) hepatitis inocula in chimpanzees." Likewise, Takahashi. K. et al. (1990) J. Gen. Virology 71(Pt9):2005-11, report that p44 is expressed in NANB hepatitis infected chimpanzees and is a host (and not a viral) protein. Additionally, Patzwahl, R. et al. (2000), supra, report that p44 expression is increased in HCV infected human livers; it is not clear whether the human p44 assembles into microtubules. Finally, Kitamura, A. et al. (1994) Eur. J. Biochem. 224:877 suggest at page 882 that "p44 may function as a mediator of anti-viral activity of interferons against hepatitis C . . . infection, through association with the microtubule aggregates."

A suitable control could be in vitro cultured chimpanzee hepatocytes that are infected with HCV, and which presumably would express p44 that assembles into microtubules and resist the HCV infection.

The foregoing in vitro model could serve to identify those candidate agents that interact with human p44 to produce a function (microtubule assembly or HCV resistance) that is characteristic of chimpanzee p44 during HCV infection. Candidate agents can also be screened in in vivo animal models for inhibition of HCV. Several in vivo human HCV models have been described in the literature. Mercer, D. et al. (2001) Nat. Med. 7(8):927-33, report that a suitable small animal model for human HCV is a SCID mouse carrying a plasminogen activator transgene (Alb-uPA) with transplanted normal human hepatocytes. The mice have chimeric human livers, and when HCV is administered via inoculation with infected human serum, serum viral titres increase. HCV viral proteins were localized to the human hepatocyte nodules.

Galun, E. et al. (1995) describe a chimeric mouse model developed from BNX (beige/nude/X-linked immunodeficient) mice preconditioned by total body irradiation and reconstituted with SCID mouse bone marrow cells, into which were implanted HCV-infected liver fragments from human patients, or normal liver incubated with HCV serum.

LaBonte, P. et al. (2002) J. Med. Virol. 66(3):312-9, describe a mouse model developed by orthotopic implantation of human hepatocellular carcinoma cells (HCC) into athymic nude mice. The human tumors produce HCV RNA.

Any of the foregoing mouse models could be treated with IFN-α/β to induce p44 production (if necessary), and candidate agents could be added to detect any inhibition in HCV infection by, e.g., reduction in serum viral titer.

As a control, chimpanzee liver hepatocytes can be implanted into SCID or another suitable mouse to create a chimeric liver, and infected with HCV. Presumably, the chimp livers in the control mouse model would express p44 and be more resistant to HCV infection.

The experimental mice with the human hepatocytes are administered candidate agents and the course of the HCV infection (e.g., viral titres) is then monitored in the control and experimental models. Those agents that improve resistance in the experimental mice to the point where the human p44 function approaches (or perhaps exceeds) the chimpanzee p44 function in the control mouse model, are agents that may be suitable for human clinical trials.

Although the foregoing invention has been described in some detail by way of illustration and example for purposes of clarity and understanding, it will be apparent to those of ordinary skill in the art that certain changes and modifications can be practiced. Therefore, the description and examples should not be construed as limiting the scope of the invention, which is delineated by the appended claims.

SEQUENCE LISTING

<160> NUMBER OF SEQ ID NOS: 36

<210> SEQ ID NO 1
<211> LENGTH: 1518

```
<212> TYPE: DNA
<213> ORGANISM: Homo sapiens

<400> SEQUENCE: 1
cagacatctg tgtccccctc aaaagtcatc ctgccccggg gaggctccgt gctggtgaca      60
tgcagcacct cctgtgacca gcccaagttg ttgggcatag agaccccgtt gcctaaaaag     120
gagttgctcc tgcctgggaa caaccggaag gtgtatgaac tgagcaatgt gcaagaagat     180
agccaaccaa tgtgctattc aaactgccct gatgggcagt caacagctaa aaccttcctc     240
accgtgtact ggactccaga acgggtggaa ctggcacccc tcccctcttg gcagccagtg     300
ggcaagaacc ttaccctacg ctgccaggtg gagggtgggg caccccgggc aacctcacc     360
gtggtgctgc tccgtgggga gaaggagctg aaacgggagc cagctgtggg ggagcccgct     420
gaggtcacga ccacggtgct ggtgaggaga gatcaccatg gagccaattt ctcgtgccgc     480
actgaactgg acctgcggcc caagggctg agctgtttg agaacacctc ggcccccta c     540
cagctccaga cctttgtcct gccagcgact cccccacaac ttgtcagccc cgggtccta     600
gaggtggaca cgcaggggac cgtggtctgt tccctggacg ggctgttccc agtctcggag     660
gcccaggtcc acctggcact gggggaccag aggttgaacc ccacagtcac ctatggcaac     720
gactccttct cggccaaggc ctcagtcagt gtgaccgcag aggacgaggg cacccagcgg     780
ctgacgtgtg cagtaatact ggggaaccag agccaggaga cactgcagac agtgaccatc     840
tacagctttc ggcgcccaa cgtgattctg acgaagccag aggtctcaga agggaccgag     900
gtgacagtga agtgtgaggc ccaccctaga gccaaggtga cgctgaatgg ggttccagcc     960
cagccactgg gcccgaggc ccagctcctg ctgaaggcca ccccagagga caacgggcgc    1020
agcttctcct gctctgcaac cctggaggtg gccggccagc ttatacacaa gaaccagacc    1080
cgggagcttc gtgtcctgta tggcccccga ctggacgaga gggattgtcc gggaaactgg    1140
acgtggccag aaaattccca gcagactcca atgtgccagg cttggggaa cccattgccc    1200
gagctcaagt gtctaaagga tggcactttc ccactgccca tcggggaatc agtgactgtc    1260
actcgagatc ttgagggcac ctacctctgt cgggccagga gcactcaagg ggaggtcacc    1320
cgcgaggtga ccgtgaatgt gctctccccc cggtatgaga ttgtcatcat cactgtggta    1380
gcagccgcag tcataatggg cactgcaggc ctcagcacgt acctctataa ccgcagcgg     1440
aagatcaaga aatacagact acaacaggcc caaaaaggga ccccatgaa accgaacaca    1500
caagccacgc ctccctga                                                 1518

<210> SEQ ID NO 2
<211> LENGTH: 1518
<212> TYPE: DNA
<213> ORGANISM: Pan troglodytes
<220> FEATURE:
<221> NAME/KEY: CDS
<222> LOCATION: (1)..(1518)

<400> SEQUENCE: 2 cag aca tct gtg tcc ccc cca aaa gtc atc ctg ccc cgg gga ggc tcc       48
Gln Thr Ser Val Ser Pro Pro Lys Val Ile Leu Pro Arg Gly Gly Ser
  1               5                  10                  15 gtg cag gtg aca tgc agc acc tcc tgt gac cag ccc gac ttg ttg ggc       96
Val Gln Val Thr Cys Ser Thr Ser Cys Asp Gln Pro Asp Leu Leu Gly
             20                  25                  30 ata gag acc ccg ttg cct aaa aag gag ttg ctt ctg ggt ggg aac aac     144
Ile Glu Thr Pro Leu Pro Lys Lys Glu Leu Leu Leu Gly Gly Asn Asn
         35                  40                  45
```

-continued

```
tgg aag gtg tat gaa ctg agc aat gtg caa gaa gat agc caa cca atg      192
Trp Lys Val Tyr Glu Leu Ser Asn Val Gln Glu Asp Ser Gln Pro Met
 50                  55                  60 tgc tat tca aac tgc cct gat ggg cag tca aca gct aaa acc ttc ctc      240
Cys Tyr Ser Asn Cys Pro Asp Gly Gln Ser Thr Ala Lys Thr Phe Leu
 65                  70                  75                  80 acc gtg tac tgg act cca gaa cgg gtg gaa ctg gca ccc ctc ccc tct      288
Thr Val Tyr Trp Thr Pro Glu Arg Val Glu Leu Ala Pro Leu Pro Ser
                 85                  90                  95 tgg cag cca gtg ggc aag gac ctt acc cta cgc tgc cag gtg gag ggt      336
Trp Gln Pro Val Gly Lys Asp Leu Thr Leu Arg Cys Gln Val Glu Gly
            100                 105                 110 ggg gca ccc cgg gcc aac ctc acc gtg gtg ctc ctc cgt ggg gag aag      384
Gly Ala Pro Arg Ala Asn Leu Thr Val Val Leu Leu Arg Gly Glu Lys
        115                 120                 125 gag ctg aaa cgg gag cca gct gtg ggg gag ccc gct gag gtc acg acc      432
Glu Leu Lys Arg Glu Pro Ala Val Gly Glu Pro Ala Glu Val Thr Thr
    130                 135                 140 acg gtg ctg gtg gag aga gat cac cat gga gcc aat ttc tcg tgc cgc      480
Thr Val Leu Val Glu Arg Asp His His Gly Ala Asn Phe Ser Cys Arg
145                 150                 155                 160 act gaa ctg gac ctg cgg ccc caa ggg ctg cag ctg ttt gag aac acc      528
Thr Glu Leu Asp Leu Arg Pro Gln Gly Leu Gln Leu Phe Glu Asn Thr
                165                 170                 175 tcg gcc ccc cac cag ctc caa acc ttt gtc ctg cca gcg act ccc cca      576
Ser Ala Pro His Gln Leu Gln Thr Phe Val Leu Pro Ala Thr Pro Pro
            180                 185                 190 caa ctt gtc agc ccc cgg gtc cta gag gtg gac acg cag ggg acc gtg      624
Gln Leu Val Ser Pro Arg Val Leu Glu Val Asp Thr Gln Gly Thr Val
        195                 200                 205 gtc tgt tcc ctg gac ggg ctg ttc cca gtc tcg gag gcc cag gtc cac      672
Val Cys Ser Leu Asp Gly Leu Phe Pro Val Ser Glu Ala Gln Val His
    210                 215                 220 ctg gca ctg ggg gac cag agg ttg aac ccc aca gtc acc tat ggc aat      720
Leu Ala Leu Gly Asp Gln Arg Leu Asn Pro Thr Val Thr Tyr Gly Asn
225                 230                 235                 240 gac tcc ttc tcg gcc aag gcc tca gtc agt gtg acc gca gag gac gag      768
Asp Ser Phe Ser Ala Lys Ala Ser Val Ser Val Thr Ala Glu Asp Glu
                245                 250                 255 ggc acc cag cgg ctg acg tgt gca gta ata ctg ggg aac cag agc cgg      816
Gly Thr Gln Arg Leu Thr Cys Ala Val Ile Leu Gly Asn Gln Ser Arg
            260                 265                 270 gag aca ctg cag aca gtg acc atc tac agc ttt ccg gcg ccc aac gtg      864
Glu Thr Leu Gln Thr Val Thr Ile Tyr Ser Phe Pro Ala Pro Asn Val
        275                 280                 285 att ctg acg aag cca gag gtc tca gaa ggg acc gag gtg aca gtg aag      912
Ile Leu Thr Lys Pro Glu Val Ser Glu Gly Thr Glu Val Thr Val Lys
    290                 295                 300 tgt gag gcc cac cct aga gcc aag gtg acg ctg aat ggg gtt cca gcc      960
Cys Glu Ala His Pro Arg Ala Lys Val Thr Leu Asn Gly Val Pro Ala
305                 310                 315                 320 cag cca gtg ggc ccg agg gtc cag ctc ctg ctg aag gcc acc cca gag     1008
Gln Pro Val Gly Pro Arg Val Gln Leu Leu Leu Lys Ala Thr Pro Glu
                325                 330                 335 gac aac ggg cgc agc ttc tcc tgc tct gca acc ctg gag gtg gcc ggc     1056
Asp Asn Gly Arg Ser Phe Ser Cys Ser Ala Thr Leu Glu Val Ala Gly
            340                 345                 350 cag ctt ata cac aag aac cag acc cgg gag ctt cgt gtc ctg tat ggc     1104
Gln Leu Ile His Lys Asn Gln Thr Arg Glu Leu Arg Val Leu Tyr Gly
```

```
                    355                 360                 365
ccc cga ctg gac gag agg gat tgt ccg gga aac tgg acg tgg cca gaa    1152
Pro Arg Leu Asp Glu Arg Asp Cys Pro Gly Asn Trp Thr Trp Pro Glu
    370                 375                 380 aat tcc cag cag act cca atg tgc cag gct tcg ggg aac cca ttg ccc    1200
Asn Ser Gln Gln Thr Pro Met Cys Gln Ala Ser Gly Asn Pro Leu Pro
385                 390                 395                 400 gag ctc aag tgt cta aag gat ggc act ttc cca ctg ccc gtc ggg gaa    1248
Glu Leu Lys Cys Leu Lys Asp Gly Thr Phe Pro Leu Pro Val Gly Glu
            405                 410                 415 tca gtg act gtc act cga gat ctt gag ggc acc tac ctc tgt cgg gcc    1296
Ser Val Thr Val Thr Arg Asp Leu Glu Gly Thr Tyr Leu Cys Arg Ala
                420                 425                 430 agg agc act caa ggg gag gtc acc cgc aag gtg acc gtg aat gtg ctc    1344
Arg Ser Thr Gln Gly Glu Val Thr Arg Lys Val Thr Val Asn Val Leu
                    435                 440                 445 tcc ccc cgg tat gag att gtc atc atc act gtg gta gca gcc gca gtc    1392
Ser Pro Arg Tyr Glu Ile Val Ile Ile Thr Val Val Ala Ala Ala Val
        450                 455                 460 ata atg ggc act gca ggc ctc agc acg tac ctc tat aac cgc cag cgg    1440
Ile Met Gly Thr Ala Gly Leu Ser Thr Tyr Leu Tyr Asn Arg Gln Arg
465                 470                 475                 480 aag atc agg aaa tac aga cta caa cag gct caa aaa ggg acc ccc atg    1488
Lys Ile Arg Lys Tyr Arg Leu Gln Gln Ala Gln Lys Gly Thr Pro Met
            485                 490                 495 aaa ccg aac aca caa gcc acg cct ccc tga                            1518
Lys Pro Asn Thr Gln Ala Thr Pro Pro
                500                 505

<210> SEQ ID NO 3
<211> LENGTH: 505
<212> TYPE: PRT
<213> ORGANISM: Pan troglodytes

<400> SEQUENCE: 3

Gln Thr Ser Val Ser Pro Pro Lys Val Ile Leu Pro Arg Gly Gly Ser
  1               5                  10                  15

Val Gln Val Thr Cys Ser Thr Ser Cys Asp Gln Pro Asp Leu Leu Gly
                 20                  25                  30

Ile Glu Thr Pro Leu Pro Lys Lys Glu Leu Leu Leu Gly Gly Asn Asn
             35                  40                  45

Trp Lys Val Tyr Glu Leu Ser Asn Val Gln Glu Asp Ser Gln Pro Met
         50                  55                  60

Cys Tyr Ser Asn Cys Pro Asp Gly Gln Ser Thr Ala Lys Thr Phe Leu
 65                  70                  75                  80

Thr Val Tyr Trp Thr Pro Glu Arg Val Glu Leu Ala Pro Leu Pro Ser
                 85                  90                  95

Trp Gln Pro Val Gly Lys Asp Leu Thr Leu Arg Cys Gln Val Glu Gly
            100                 105                 110

Gly Ala Pro Arg Ala Asn Leu Thr Val Val Leu Leu Arg Gly Glu Lys
        115                 120                 125

Glu Leu Lys Arg Glu Pro Ala Val Gly Glu Pro Ala Glu Val Thr Thr
    130                 135                 140

Thr Val Leu Val Glu Arg Asp His His Gly Ala Asn Phe Ser Cys Arg
145                 150                 155                 160

Thr Glu Leu Asp Leu Arg Pro Gln Gly Leu Gln Leu Phe Glu Asn Thr
                165                 170                 175
```

```
Ser Ala Pro His Gln Leu Gln Thr Phe Val Leu Pro Ala Thr Pro Pro
            180                 185                 190

Gln Leu Val Ser Pro Arg Val Leu Glu Val Asp Thr Gln Gly Thr Val
            195                 200                 205

Val Cys Ser Leu Asp Gly Leu Phe Pro Val Ser Glu Ala Gln Val His
        210                 215                 220

Leu Ala Leu Gly Asp Gln Arg Leu Asn Pro Thr Val Thr Tyr Gly Asn
225                 230                 235                 240

Asp Ser Phe Ser Ala Lys Ala Ser Val Ser Val Thr Ala Glu Asp Glu
                245                 250                 255

Gly Thr Gln Arg Leu Thr Cys Ala Val Ile Leu Gly Asn Gln Ser Arg
            260                 265                 270

Glu Thr Leu Gln Thr Val Thr Ile Tyr Ser Phe Pro Ala Pro Asn Val
            275                 280                 285

Ile Leu Thr Lys Pro Glu Val Ser Glu Gly Thr Glu Val Thr Val Lys
        290                 295                 300

Cys Glu Ala His Pro Arg Ala Lys Val Thr Leu Asn Gly Val Pro Ala
305                 310                 315                 320

Gln Pro Val Gly Pro Arg Val Gln Leu Leu Lys Ala Thr Pro Glu
                325                 330                 335

Asp Asn Gly Arg Ser Phe Ser Cys Ser Ala Thr Leu Glu Val Ala Gly
            340                 345                 350

Gln Leu Ile His Lys Asn Gln Thr Arg Glu Leu Arg Val Leu Tyr Gly
            355                 360                 365

Pro Arg Leu Asp Glu Arg Asp Cys Pro Gly Asn Trp Thr Trp Pro Glu
        370                 375                 380

Asn Ser Gln Gln Thr Pro Met Cys Gln Ala Ser Gly Asn Pro Leu Pro
385                 390                 395                 400

Glu Leu Lys Cys Leu Lys Asp Gly Thr Phe Pro Leu Pro Val Gly Glu
                405                 410                 415

Ser Val Thr Val Thr Arg Asp Leu Glu Gly Thr Tyr Leu Cys Arg Ala
            420                 425                 430

Arg Ser Thr Gln Gly Glu Val Thr Arg Lys Val Thr Val Asn Val Leu
            435                 440                 445

Ser Pro Arg Tyr Glu Ile Val Ile Ile Thr Val Ala Ala Ala Val
        450                 455                 460

Ile Met Gly Thr Ala Gly Leu Ser Thr Tyr Leu Tyr Asn Arg Gln Arg
465                 470                 475                 480

Lys Ile Arg Lys Tyr Arg Leu Gln Gln Ala Gln Lys Gly Thr Pro Met
                485                 490                 495

Lys Pro Asn Thr Gln Ala Thr Pro Pro
            500                 505

<210> SEQ ID NO 4
<211> LENGTH: 1515
<212> TYPE: DNA
<213> ORGANISM: Gorilla gorilla

<400> SEQUENCE: 4
cagacatctg tgtcccccccc aaaagtcatc ctgccccggg gaggctccgt gctggtgaca    60
tgcagcacct cctgtgacca gcccaccttg ttgggcatag agacccgtt gcctaaaaag    120 gagttgctcc tgcttgggaa caaccagaag gtgtatgaac tgagcaatgt gcaagaagat    180
agccaaccaa tgtgttattc aaactgccct gatgggcagt caacagctaa aaccttcctc    240
```

```
accgtgtact ggactccaga acgggtggaa ctggcacccc tcccctcttg gcagccagtg      300
ggcaaggacc ttaccctacg ctgccaggtg gagggtgggg caccccgggc caacctcatc      360
gtggtgctgc tccgtgggga ggaggagctg aaacgggagc cagctgtggg ggagcccgcc      420
gaggtcacga ccacggtgcc ggtggagaaa gatcaccatg gagccaattt cttgtgccgc      480
actgaactgg acctgcggcc ccaagggctg aagctgtttg agaacacctc ggcccccctac      540 cagctccaaa cctttgtcct gccagcgact cccccacaac ttgtcagccc tcgggtccta      600
gaggtggaca cgcaggggac tgtggtctgt tccctggacg ggctgttccc agtctcggag      660
gcccaggtcc acctggcact gggggaccag aggttgaacc ccacagtcac ctatggcaac      720
gactccttct cagccaaggc ctcagtcagt gtgaccgcag aggacgaggg cacccagtgg      780
ctgacgtgtg cagtaatact ggggaccag agccaggaga cactgcagac agtgaccatc      840
tacagctttc cggcacccaa cgtgattctg acgaagccag aggtctcaga agggaccgag      900
gtgacagtga agtgtgaggc ccaccctaga gccaaggtga cactgaatgg ggttccagcc      960
cagccaccgg gcccgaggac ccagttcctg ctgaaggcca cccagagga caacgggcgc     1020 agcttctcct gctctgcaac cctggaggtg gccggccagc ttatacacaa gaaccagacc     1080
cgggagcttc gtgtcctgta tgccccccga ctggatgaga gggattgtcc gggaaactgg     1140
acgtggccag aaaattccca gcagactcca atgtgccagg cttgggggaa cccattgccc     1200
gagctcaagt gtctaaagga tggcactttc ccactgcccg tcggggaatc agtgactgtc     1260
actcgagatc ttgagggcac ctacctctgt cgggccagga gcactcaagg ggaggtcacc     1320
cgcgaggtga ccgtgaatgt gctctccccc cggtatgagt ttgtcatcat cgctgtggta     1380
gcagccgcag tcataatggg cactgcaggc ctcagcacgt acctctataa ccgccagcgg     1440
aagatcagga aatacagact acaacaggct caaaaaggga cccccatgaa accgaacaca     1500
caagccacgc ctccc                                                     1515

<210> SEQ ID NO 5
<211> LENGTH: 1515
<212> TYPE: DNA
<213> ORGANISM: Pongo pygmaeus

<400> SEQUENCE: 5
cacacatctg tgtcctccgc caacgtcttc ctgccccggg gaggctccgt gctagtgaat       60
tgcagcacct cctgtgacca gcccaccttg ttgggcatag agaccccgtt gcctaaaaag      120
gagttgctcc cggtgggaa caactggaag atgtatgaac tgagcaatgt gcaagaagat      180
agccaaccaa tgtgctattc aaactgccct gatgggcagt cagcagctaa aaccttcctc      240
accgtgtact ggactccaga acgggtggaa ctggcacccc tcccctcttg gcagccagtg      300
ggcaagaacc ttaccctacg ctgccaggtg gagggtgggg caccccgggc caacctcacc      360
gtggtattgc tccgtgggga ggaggagctg agccggcagc cagcggtggg ggagcccgcc      420
gaggtcacgg ccacggtgct ggcgaggaaa gatgaccacg gagccaattt ctcgtgccgc      480
actgaactgg acctgcggcc ccaagggctg agctgtttg agaacacctc ggcccccac      540 cagctccaaa cctttgtcct gccagcgact cccccacaac ttgtcagccc ccgggtccta      600
gaggtggaca cgcaggggac cgtggtctgt tccctggacg ggctgttccc agtctcggag      660
gcccaggtcc acttggcact gggggaccag aggttgaacc ccacagtcac ctatggcgtc      720
gactccctct cggccaaggc ctcagtcagt gtgaccgcag aggaggaggg cacccagtgg      780
ctgtggtgtg cagtgatact gaggaaccag agccaggaga cacggcagac agtgaccatc      840
```

```
tacagctttc ctgcacccaa cgtgactctg atgaagccag aggtctcaga agggaccgag    900
gtgatagtga agtgtgaggc ccaccctgca gccaacgtga cgctgaatgg ggttccagcc    960
cagccgccgg gcccgagggc ccagttcctg ctgaaggcca ccccagagga caacgggcgc   1020
agcttctcct gctctgcaac cctggaggtg gccggccagc ttatacacaa gaaccagacc   1080
cgggagcttc gagtcctgta tggcccccga ctggacgaga gggattgtcc gggaaactgg   1140
acgtggccag aaaactccca gcagactcca atgtgccagg cttgggggaa ccccttgccc   1200
gagctcaagt gtctaaagga tggcactttc ccactgccca tcggggaatc agtgactgtc   1260
actcgagatc ttgagggcac ctacctctgt cgggccagga gcactcaagg ggaggtcacc   1320
cgcgaggtga ccgtgaatgt gctctccccc cggtatgaga ttgtcatcat cactgtggta   1380
gcagccgcag ccatactggg cactgcaggc ctcagcacgt acctctataa ccgccagcgg   1440
aagatcagga tatacagact acaacaggct caaaaggga cccccatgaa accaaacaca   1500
caaaccacgc ctccc                                                   1515
```

<210> SEQ ID NO 6
<211> LENGTH: 505
<212> TYPE: PRT
<213> ORGANISM: Homo sapiens

<400> SEQUENCE: 6

```
Gln Thr Ser Val Ser Pro Ser Lys Val Ile Leu Pro Arg Gly Gly Ser
  1               5                  10                  15

Val Leu Val Thr Cys Ser Thr Ser Cys Asp Gln Pro Lys Leu Leu Gly
                 20                  25                  30

Ile Glu Thr Pro Leu Pro Lys Lys Glu Leu Leu Leu Pro Gly Asn Asn
             35                  40                  45

Arg Lys Val Tyr Glu Leu Ser Asn Val Gln Glu Asp Ser Gln Pro Met
         50                  55                  60

Cys Tyr Ser Asn Cys Pro Asp Gly Gln Ser Thr Ala Lys Thr Phe Leu
 65                  70                  75                  80

Thr Val Tyr Trp Thr Pro Glu Arg Val Glu Leu Ala Pro Leu Pro Ser
                 85                  90                  95

Trp Gln Pro Val Gly Lys Asn Leu Thr Leu Arg Cys Gln Val Glu Gly
                100                 105                 110

Gly Ala Pro Arg Ala Asn Leu Thr Val Val Leu Leu Arg Gly Glu Lys
            115                 120                 125

Glu Leu Lys Arg Glu Pro Ala Val Gly Glu Pro Ala Glu Val Thr Thr
        130                 135                 140

Thr Val Leu Val Arg Arg Asp His His Gly Ala Asn Phe Ser Cys Arg
145                 150                 155                 160

Thr Glu Leu Asp Leu Arg Pro Gln Gly Leu Glu Leu Phe Glu Asn Thr
                165                 170                 175

Ser Ala Pro Tyr Gln Leu Gln Thr Phe Val Leu Pro Ala Thr Pro Pro
            180                 185                 190

Gln Leu Val Ser Pro Arg Val Leu Glu Val Asp Thr Gln Gly Thr Val
        195                 200                 205

Val Cys Ser Leu Asp Gly Leu Phe Pro Val Ser Glu Ala Gln Val His
    210                 215                 220

Leu Ala Leu Gly Asp Gln Arg Leu Asn Pro Thr Val Thr Tyr Gly Asn
225                 230                 235                 240

Asp Ser Phe Ser Ala Lys Ala Ser Val Ser Val Thr Ala Glu Asp Glu
```

```
                245                 250                 255
Gly Thr Gln Arg Leu Thr Cys Ala Val Ile Leu Gly Asn Gln Ser Gln
            260                 265                 270

Glu Thr Leu Gln Thr Val Thr Ile Tyr Ser Phe Pro Ala Pro Asn Val
        275                 280                 285

Ile Leu Thr Lys Pro Glu Val Ser Glu Gly Thr Glu Val Thr Val Lys
    290                 295                 300

Cys Glu Ala His Pro Arg Ala Lys Val Thr Leu Asn Gly Val Pro Ala
305                 310                 315                 320

Gln Pro Leu Gly Pro Arg Ala Gln Leu Leu Lys Ala Thr Pro Glu
            325                 330                 335

Asp Asn Gly Arg Ser Phe Ser Cys Ser Ala Thr Leu Glu Val Ala Gly
            340                 345                 350

Gln Leu Ile His Lys Asn Gln Thr Arg Glu Leu Arg Val Leu Tyr Gly
        355                 360                 365

Pro Arg Leu Asp Glu Arg Asp Cys Pro Gly Asn Trp Thr Trp Pro Glu
    370                 375                 380

Asn Ser Gln Gln Thr Pro Met Cys Gln Ala Trp Gly Asn Pro Leu Pro
385                 390                 395                 400

Glu Leu Lys Cys Leu Lys Asp Gly Thr Phe Pro Leu Pro Ile Gly Glu
            405                 410                 415

Ser Val Thr Val Thr Arg Asp Leu Glu Gly Thr Tyr Leu Cys Arg Ala
            420                 425                 430

Arg Ser Thr Gln Gly Glu Val Thr Arg Glu Val Thr Val Asn Val Leu
        435                 440                 445

Ser Pro Arg Tyr Glu Ile Val Ile Ile Thr Val Ala Ala Ala Val
    450                 455                 460

Ile Met Gly Thr Ala Gly Leu Ser Thr Tyr Leu Tyr Asn Arg Gln Arg
465                 470                 475                 480

Lys Ile Lys Lys Tyr Arg Leu Gln Gln Ala Gln Lys Gly Thr Pro Met
            485                 490                 495

Lys Pro Asn Thr Gln Ala Thr Pro Pro
            500                 505

<210> SEQ ID NO 7
<211> LENGTH: 254
<212> TYPE: PRT
<213> ORGANISM: Homo sapiens

<400> SEQUENCE: 7

Ser Asp Glu Lys Val Phe Glu Val His Val Arg Pro Lys Lys Leu Ala
1               5                   10                  15

Val Glu Pro Lys Gly Ser Leu Glu Val Asn Cys Ser Thr Thr Cys Asn
            20                  25                  30

Gln Pro Glu Val Gly Gly Leu Glu Thr Ser Leu Asp Lys Ile Leu Leu
        35                  40                  45

Asp Glu Gln Ala Gln Trp Lys His Tyr Leu Val Ser Asn Ile Ser His
    50                  55                  60

Asp Thr Val Leu Gln Cys His Phe Thr Cys Ser Gly Lys Gln Glu Ser
65                  70                  75                  80

Met Asn Ser Asn Val Ser Val Tyr Gln Pro Pro Arg Gln Val Ile Leu
            85                  90                  95

Thr Leu Gln Pro Thr Leu Val Ala Val Gly Lys Ser Phe Thr Ile Glu
        100                 105                 110
```

```
Cys Arg Val Pro Thr Val Glu Pro Leu Asp Ser Leu Thr Leu Phe Leu
        115                 120                 125

Phe Arg Gly Asn Glu Thr Leu His Tyr Glu Thr Phe Gly Lys Ala Ala
130                 135                 140

Pro Ala Pro Gln Glu Ala Thr Ala Thr Phe Asn Ser Thr Ala Asp Arg
145                 150                 155                 160

Glu Asp Gly His Arg Asn Phe Ser Cys Leu Ala Val Leu Asp Leu Met
                165                 170                 175

Ser Arg Gly Gly Asn Ile Phe His Lys His Ser Ala Pro Lys Met Leu
                180                 185                 190

Glu Ile Tyr Glu Pro Val Ser Asp Ser Gln Met Val Ile Ile Val Thr
        195                 200                 205

Val Val Ser Val Leu Leu Ser Leu Phe Val Thr Ser Val Leu Leu Cys
210                 215                 220

Phe Ile Phe Gly Gln His Leu Arg Gln Gln Arg Met Gly Thr Tyr Gly
225                 230                 235                 240

Val Arg Ala Ala Trp Arg Arg Leu Pro Gln Ala Phe Arg Pro
                245                 250

<210> SEQ ID NO 8
<211> LENGTH: 518
<212> TYPE: PRT
<213> ORGANISM: Homo sapiens

<400> SEQUENCE: 8

Gln Glu Phe Leu Leu Arg Val Glu Pro Gln Asn Pro Val Leu Ser Ala
1               5                   10                  15

Gly Gly Ser Leu Phe Val Asn Cys Ser Thr Asp Cys Pro Ser Ser Glu
                20                  25                  30

Lys Ile Ala Leu Glu Thr Ser Leu Ser Lys Glu Leu Val Ala Ser Gly
            35                  40                  45

Met Gly Trp Ala Ala Phe Asn Leu Ser Asn Val Thr Gly Asn Ser Arg
    50                  55                  60

Ile Leu Cys Ser Val Tyr Cys Asn Gly Ser Gln Ile Thr Gly Ser Ser
65                  70                  75                  80

Asn Ile Thr Val Tyr Gly Leu Pro Glu Arg Val Glu Leu Ala Pro Leu
                85                  90                  95

Pro Pro Trp Gln Pro Val Gly Gln Asn Phe Thr Leu Arg Cys Gln Val
                100                 105                 110

Glu Gly Gly Ser Pro Arg Thr Ser Leu Thr Val Leu Leu Arg Trp
            115                 120                 125

Glu Glu Glu Leu Ser Arg Gln Pro Ala Val Glu Glu Pro Ala Glu Val
130                 135                 140

Thr Ala Thr Val Leu Ala Ser Arg Asp Asp His Gly Ala Pro Phe Ser
145                 150                 155                 160

Cys Arg Thr Glu Leu Asp Met Gln Pro Gln Gly Leu Gly Leu Phe Val
                165                 170                 175

Asn Thr Ser Ala Pro Arg Gln Leu Arg Thr Phe Val Leu Pro Val Thr
                180                 185                 190

Pro Pro Arg Leu Val Ala Pro Arg Phe Leu Glu Val Glu Thr Ser Trp
                195                 200                 205

Pro Val Asp Cys Thr Leu Asp Gly Leu Phe Pro Ala Ser Glu Ala Gln
        210                 215                 220

Val Tyr Leu Ala Leu Gly Asp Gln Met Leu Asn Ala Thr Val Met Asn
225                 230                 235                 240
```

His Gly Asp Thr Leu Thr Ala Thr Ala Thr Ala Arg Ala Asp
            245                 250                 255

Gln Glu Gly Ala Arg Glu Ile Val Cys Asn Val Thr Leu Gly Gly Glu
            260                 265                 270

Arg Arg Glu Ala Arg Glu Asn Leu Thr Val Phe Ser Phe Leu Gly Pro
            275                 280                 285

Ile Val Asn Leu Ser Glu Pro Thr Ala His Glu Gly Ser Thr Val Thr
            290                 295                 300

Val Ser Cys Met Ala Gly Ala Arg Val Gln Val Thr Leu Asp Gly Val
305                 310                 315                 320

Pro Ala Ala Ala Pro Gly Gln Pro Ala Gln Leu Gln Leu Asn Ala Thr
            325                 330                 335

Glu Ser Asp Asp Gly Arg Ser Phe Phe Cys Ser Ala Thr Leu Glu Val
            340                 345                 350

Asp Gly Glu Phe Leu His Arg Asn Ser Ser Val Gln Leu Arg Val Leu
            355                 360                 365

Tyr Gly Pro Lys Ile Asp Arg Ala Thr Cys Pro Gln His Leu Lys Trp
            370                 375                 380

Lys Asp Lys Thr Arg His Val Leu Gln Cys Gln Ala Arg Gly Asn Pro
385                 390                 395                 400

Tyr Pro Glu Leu Arg Cys Leu Lys Glu Gly Ser Ser Arg Glu Val Pro
            405                 410                 415

Val Gly Ile Pro Phe Phe Val Asn Val Thr His Asn Gly Thr Tyr Gln
            420                 425                 430

Cys Gln Ala Ser Ser Ser Arg Gly Lys Tyr Thr Leu Val Val Val Met
            435                 440                 445

Asp Ile Glu Ala Gly Ser Ser His Phe Val Pro Val Phe Val Ala Val
            450                 455                 460

Leu Leu Thr Leu Gly Val Val Thr Ile Val Leu Ala Leu Met Tyr Val
465                 470                 475                 480

Phe Arg Glu His Gln Arg Ser Gly Ser Tyr His Val Arg Glu Glu Ser
            485                 490                 495

Thr Tyr Leu Pro Leu Thr Ser Met Gln Pro Thr Glu Ala Met Gly Glu
            500                 505                 510

Glu Pro Ser Arg Ala Glu
            515

<210> SEQ ID NO 9
<211> LENGTH: 1212
<212> TYPE: DNA
<213> ORGANISM: Homo sapiens

<400> SEQUENCE: 9
atgagtgact ccaaggaacc aagactgcag cagctgggcc tcctggagga ggaacagctg      60
agaggccttg gattccgaca gactcgagga tacaagagct tagcagggtg tcttggccat     120
ggtcccctgg tgctgcaact cctctccttc acgtcttggg ctgggctcct tgtccaagtg     180
tccaaggtcc ccagctccat aagtcaggaa caatccaggc aagacgcgat ctaccagaac     240
ctgacccagc ttaaagctgc agtgggtgag ctctcagaga atccaagct gcaggagatc     300 taccaggagc tgacccagct gaaggctgca gtgggtgagc ttccagagaa atctaagctg     360
caggagatct accaggagct gacccggctg aaggctgcag tgggtgagct tccagagaaa     420 tctaagctg aggagatcta ccaggagctg acctggctga aggctgcagt gggtgagctt     480

```
ccagagaaat ctaagatgca ggagatctac caggagctga ctcggctgaa ggctgcagtg      540
ggtgagcttc cagagaaatc taagcagcag gagatctacc aggagctgac ccggctgaag      600
gctgcagtgg gtgagcttcc agagaaatct aagcagcagg agatctacca ggagctgacc      660
cggctgaagg ctgcagtggg tgagcttcca gagaaatcta agcagcagga gatctaccag      720
gagctgaccc agctgaaggc tgcagtggaa cgcctgtgcc accccctgtcc ctgggaatgg     780 acattcttcc aaggaaactg ttacttcatg tctaactccc agcggaactg gcacgactcc      840
atcaccgcct gcaaagaagt gggggcccag ctcgtcgtaa tcaaaagtgc tgaggagcag      900
aacttcctac agctgcagtc ttccagaagt aaccgcttca cctggatggg actttcagat      960
ctaaatcagg aaggcacgtg gcaatgggtg gacggctcac ctctgttgcc cagcttcaag     1020
cagtattgga acagaggaga gcccaacaac gttggggagg aagactgcgc ggaatttagt     1080
ggcaatggct ggaacgacga caaatgtaat cttgccaaat tctggatctg caaaaagtcc     1140
gcagcctcct gctccaggga tgaagaacag tttctttctc cagcccctgc caccccaaac     1200
ccccctcctg cg                                                         1212

<210> SEQ ID NO 10
<211> LENGTH: 1212
<212> TYPE: DNA
<213> ORGANISM: Pan troglodytes

<400> SEQUENCE: 10
atgagtgact ccaaggaacc aagactgcag cagctgggcc tcctggagga ggaacagctg       60
agaggccttg gattccgaca gactcgaggc tacaagagct tagcagggtg tcttggccat      120
ggtcccctgg tgctgcaact cctctccttc acgctcttgg ctgggctcct tgtccaagtg      180
tccaaggtcc ccagctccat aagtcaggaa gaatccaggc aagacgtgat ctaccagaac      240
ctgacccagc ttaaagctgc agtgggtgag ctctcagaga aatccaagct gcaggagatc      300
taccaggagc tgacccagct gaaggctgca gtgggtgagc ttccagagaa atctaagcag      360
caggagatct accaggagct gacccggctg aaggctgcag tgggtgagct tccagagaaa      420
tctaagatgc aggagatcta ccaggagctg actcggctga aggctgcagt gggtgagctt      480
ccagagaaat ctaagatgca ggagatctac caggagctga ctcggctgaa ggctgcagtg      540
ggtgagcttc cagagaaatc taagcagcag gagatctacc aggagctgac ccagctgaag      600
gctgcagtgg gtgagcttcc agagaaatct aagcagcagg agatctacca ggagctgacc      660
cagctgaagg ctgcagtggg tgagcttcca gagaaatcta agcagcagga gatctaccag      720
gagctgaccc ggctgaaggc tgcagtggaa cgcctgtgcc gccgctgccc ctgggaatgg      780
acattcttcc aaggaaactg ttacttcatg tctaactccc agcggaactg gcacgactcc      840
atcactgcct gcaaagaagt gggggcccag ctcgtcgtaa tcaaaagtgc tgaggagcag      900
aacttcctac agctgcagtc ttccagaagt aaccgcttca cctggatggg actttcagat      960
ctaaatgagg aaggcatgtg gcaatgggtg gacggctcac ctctgttgcc cagcttcaac     1020
cagtaytgga acagaggaga gcccaacaac gttggggagg aagactgcgc ggaatttagt     1080
ggcaatggct ggaatgacga caaatgtaat cttgccaaat tctggatctg caaaaagtcc     1140
gcagcctcct gctccaggga tgaagaacag tttctttctc cagcccctgc caccccaaac     1200
ccccctcctg cg                                                         1212

<210> SEQ ID NO 11
<211> LENGTH: 1212
```

<212> TYPE: DNA
<213> ORGANISM: Gorilla gorilla

<400> SEQUENCE: 11

```
atgagtgact ccaaggaacc aagactgcag cagctgggcc tcctggagga ggaacagctg      60
agaggccttg gattccgaca gactcgaggc tacaagagct tagcagggtg tcttggccat     120
ggtcccctgg tgctgcaact cctctccttc acgctcttgg ctgcgctcct tgtccaagtg     180
tccaaggtcc ccagctccat aagtcaggaa caatccaggc aagacgcgat ctaccagaac     240
ctgacccagt ttaaagctgc agtgggtgag ctctcagaga atccaagct gcaggagatc      300
tatcaggagc tgacccagct gaaggctgca gtgggtgagc ttccagagaa atctaagcag     360
caggagatct accaggagct gagccagctg aaggctgcag tgggtgagct tccagagaaa     420
tctaagcagc aggagatcta ccaggagctg acccggctga aggctgcagt gggtgagctt     480
ccagagaaat ctaagcagca ggagatctac caggagctga cccggctgaa ggctgcagtg     540
ggtgagcttc agagaaatc taagcagcag gagatctacc aggagctgag ccagctgaag     600
gctgcagtgg gtgagcttcc agagaaatct aagcagcagg agatctacca ggagctgagc     660
cagctgaagg ctgcagtggg tgagcttcca gagaaatcta agcagcagga gatctaccag     720
gagctgaccc agctgaaggc tgcagtggaa cgcctgtgcc gccgctgccc ctgggaatgg     780
acattcttcc aaggaaactg ttacttcatg tctaactccc agcggaactg gcacgactcc     840
atcaccgcct gccaagaagt gggggcccag ctcgtcgtaa tcaaaagtgc tgaggagcag     900
aacttcctac agctgcagtc ttccagaagt aaccgcttca cctggatggg actttcagat     960
ctaaatcatg aaggcacgtg gcaatgggtg gacggctcac ctctgttgcc cagcttcgag    1020
cagtattgga acagaggaga gcccaacaac gttggggagg aagactgcgc ggaatttagt    1080
ggcaatggct ggaacgatga caaatgtaat cttgccaaat tctggatctg caaaaagtct    1140
gcagcctcct gctccaggga tgaagaacag tttctttctc agcctctgc acccccaaac     1200
ccccctcctg cg                                                        1212
```

<210> SEQ ID NO 12
<211> LENGTH: 105
<212> TYPE: PRT
<213> ORGANISM: Pan troglodytes

<400> SEQUENCE: 12

```
Ser Leu Gln Cys Tyr Asn Cys Pro Asn Pro Thr Ala Asp Cys Lys Thr
  1               5                  10                  15

Ala Val Asn Cys Ser Ser Asp Phe Asp Ala Cys Leu Ile Thr Lys Ala
             20                  25                  30

Gly Leu Gln Val Tyr Asn Lys Cys Trp Lys Phe Glu His Cys Asn Phe
         35                  40                  45

Asn Asp Val Thr Thr Arg Leu Arg Glu Asn Glu Leu Thr Tyr Tyr Cys
     50                  55                  60

Cys Lys Lys Asp Leu Cys Asn Phe Asn Glu Gln Leu Glu Asn Gly Gly
 65                  70                  75                  80

Thr Ser Leu Ser Glu Lys Thr Val Leu Leu Val Thr Pro Phe Leu
                 85                  90                  95

Ala Ala Ala Ala Trp Ser Leu His Pro
            100                 105
```

<210> SEQ ID NO 13
<211> LENGTH: 121

```
<212> TYPE: PRT
<213> ORGANISM: Pan troglodytes

<400> SEQUENCE: 13

Ser Leu Gln Cys Tyr Asn Cys Pro Asn Pro Thr Ala Asp Cys Lys Thr
  1               5                  10                  15

Ala Val Asn Cys Ser Ser Asp Phe Asp Ala Cys Leu Ile Thr Lys Ala
             20                  25                  30

Gly Leu Gln Val Tyr Asn Lys Cys Trp Lys Leu Glu His Cys Asn Phe
         35                  40                  45

Lys Asp Leu Thr Thr Arg Leu Arg Glu Asn Glu Leu Thr Tyr Tyr Cys
     50                  55                  60

Cys Lys Lys Asp Leu Cys Asn Phe Asn Glu Gln Leu Glu Asn Gly Gly
 65                  70                  75                  80

Asn Glu Gln Leu Glu Asn Gly Gly Asn Glu Gln Leu Glu Asn Gly Gly
                 85                  90                  95

Thr Ser Leu Ser Glu Lys Thr Val Leu Leu Arg Val Thr Pro Phe Leu
            100                 105                 110

Ala Ala Ala Ala Trp Ser Leu His Pro
        115                 120

<210> SEQ ID NO 14
<211> LENGTH: 5140
<212> TYPE: DNA
<213> ORGANISM: Homo sapiens

<400> SEQUENCE: 14
ctccagacct acccagaaag atgcccggat ggatcctgca gctccgtggc ttttctggga      60
agcagcggcc cctgctctca agagaccctg gctcctgatg gtggcccaa ggttgccagc     120
tggtgctagg gactcaggac agtttcccag aaaaggccaa gcgggcagcc cctccagggg    180
ccgggtgagg aagctggggg gtgcggaggc cacactgggt ccctgaaccc cctgcttggt    240
tacagtgcag ctcctcaagt ccacagacgt gggccggcac agcctcctgt acctgaagga    300
aatcggccgt ggctggttcg ggaaggtgtt cctgggggga gtgaactctg gcatcagcag    360
tgcccaggtg gtggtgaagg agctgcaggc tagtgccagc gtgcaggagc agatgcagtt    420
cctggaggag gtgcagccct acagggccct gaagcacagc aacctgctcc agtgcctggc    480
ccagtgcgcc gaggtgacgc cctacctgct ggtgatggag ttctgcccac tgggggacct    540
caagggctac ctgcgagct gccgggtggc ggagtccatg gctcccgacc ccgacccct    600
gcagcgcatg gcctgtgagg tggcctgtgg cgtcctgcac cttcatcgca caatttcgt    660
gcacagcgac ctggccctgc ggaactgcct gctcacggct gacctgacgg tgaagattgg    720
tgactatggc ctggctcact gcaagtacag agaggactac ttcgtgactg ccgaccagct    780
gtgggtgcct ctgcgctgga tcgcgccaga gctggtggac gaggtgcata gcaacctgct    840
cgtcgtggac cagaccaaga gcgggaatgt gtggtccctg ggcgtgacca tctgggagct    900
ctttgagctg ggcacgcagc cctatcccca gcactggac cagcaggtgc tggcgtacac    960
ggtccgggag cagcagctca agctgcccaa gccccagctg cagctgaccc tgtcggaccg   1020
ctggtacgag gtgatgcagt tctgctggct gcagccgag cagcggccca gccgagga    1080
ggtgcacctg ctgctgtcct acctgtgtgc caagggcgcc accgaagcag aggaggagtt   1140
tgaacgcgc tggcgctctc tgcggcccgg cggggggcgc gtgggccg ggccggtgc      1200
ggcggggccc atgctgggcg gcgtggtgga gctcgccgct gcctcgtcct tcccgctgct   1260
```

```
ggagcagttc gcgggcgacg gcttccacgc ggacggcgac gacgtgctga cggtgaccga    1320
gaccagccga ggcctcaatt ttgagtacaa gtgggaggcg ggccgcggcg cggaggcctt    1380
cccggccacg ctgagccctg ccgcaccgc acgcctgcag gagctgtgcg cccccgacgg    1440 cgcgccccg ggcgtggttc cggtgctcag cgcgcacagc ccgtcgctgg gcagcgagta    1500
cttcatccgc ctagaggagg ccgcaccgc cgccggccac gaccctgact gcgccggctg    1560
cgcccccagt ccacctgcca ccgcggacca ggacgacgac tctgacggca gcaccgccgc    1620
ctcgctggcc atggagccgc tgctgggcca cgggccaccc gtcgacgtcc cctggggccg    1680
cggcgaccac taccctcgca gaagcttggc gcggacccg ctctgcccct cacgctctcc    1740
ctcgccctcg gcggggcccc tgagtctggc ggagggagga gcggaggatg cagactgggg    1800
cgtggccgcc ttctgtcctg ccttcttcga ggacccactg gcacgtccc ctttggggag    1860 ctcaggggcg ccccgctgc cgctgactgg cgaggatgag ctagaggagg tgggagcgcg    1920
gagggccgcc cagcgcgggc actggcgctc caacgtgtca gccaacaaca acagcggcag    1980
ccgctgtcca gagtcctggg accccgtctc tgcgggctgc cacgctgagg gctgccccag    2040
tccaaagcag accccacggg cctcccccga gccggggtac cctggagagc ctctgcttgg    2100
gctccaggca gcctctgccc aggagccagg ctgctgcccc ggcctccctc atctatgctc    2160
tgcccagggc ctggcacctg ctccctgcct ggttacaccc tcctggacag agacagccag    2220 tagtggggt gaccacccgc aggcagagcc caagcttgcc acggaggctg agggcactac    2280 cggacccgc ctgccccttc cttccgtccc ctccccatcc caggagggag ccccacttcc    2340
ctcggaggag gccagtgccc ccgacgcccc tgatgccctg cctgactctc ccacgcctgc    2400
tactggtggc gaggtgtctg ccatcaagct ggcttctgcc ctgaatggca gcagcagctc    2460
tcccgaggtg gaggcaccca gcagtgagga tgaggacacg gctgaggcca cctcaggcat    2520
cttcaccgac acgtccagcg acggcctgca ggccaggagg ccggatgtgg tgccagcctt    2580
ccgctctctg cagaagcagg tggggacccc cgactccctg gactccctgg acatcccgtc    2640
ctcagccagt gatggtggct atgaggtctt cagcccgtcg ccactggcc cctctggagg    2700 gcagccgcga gcgctggaca gtggctatga caccgagaac tatgagtccc ctgagtttgt    2760
gctcaaggag gcgcaggaag ggtgtgagcc ccaggccttt gcggagctgg cctcagaggg    2820
tgagggcccc gggcccgaga cacggctctc cacctccctc agtggcctca cgagaagaa    2880 tccctaccga gactctgcct acttctcaga cctcgaggct gaggccgagg ccacctcagg    2940
cccagagaag aagtgcggcg gggaccgagc ccccgggcca gagctgggcc tgccgagcac    3000
tgggcagccg tctgagcagg tctgtctcag gcctggggtt ccggggagg cacaaggctc    3060 tggcccggg gaggtgctgc ccccactgct gcagcttgaa gggtcctccc cagagcccag    3120
cacctgcccc tcgggcctgg tcccagagcc tccggagccc caaggcccag ccaaggtgcg    3180
gcctgggccc agccccagct gctcccagtt tttcctgctg accccggttc cgctgagatc    3240
agaaggcaac agctctgagt tccaggggcc cccaggactg ttgtcagggc cggccccaca    3300
aaagcggatg ggggggccag gcaccccag agccccactc cgcctggctc tgcccggcct    3360
ccctgcggcc ttgagggcc ggccggagga ggaggaggag acagtgagg acagcgacga    3420 gtctgacgag gagctccgct gctacagcgt ccaggagcct agcgaggaca gcgaagagga    3480
ggcgccggcg gtgcccgtgg tggtggctga gagccagagc gcgcgcaacc tgcgcagcct    3540
gctcaagatg cccagcctgc tgtccgagac cttctgcgag gacctggaac gcaagaagaa    3600
ggccgtgtcc ttcttcgacg acgtcaccgt ctacctcttt gaccaggaaa gccccacccg    3660
```

```
ggagctcggg gagcccttcc cgggcgccaa ggaatcgccc cctacgttcc ttaggggggag    3720 ccccggctct cccagcgccc ccaaccggcc gcagcaggct gatggctccc caaatggctc    3780
cacagcggaa gagggtggtg ggttcgcgtg ggacgacgac ttcccgctga tgacggccaa    3840
ggcagccttc gccatggccc tagacccggc cgcacccgcc ccggctgcgc ccacgcccac    3900
gcccgctccc ttctcgcgct tcacggtgtc gcccgcgccc acgtcccgct tctccatcac    3960
gcacgtgtct gactcggacg ccgagtccaa gagaggacct gaagctggtg ccggggggtga    4020 gagtaaagag gcttgagacc tgggcagctc ctgcccctca aggctggcgt caccggagcc    4080
cctgccaggc agcagcgagg atggtgaccg agaaggtggg gaccacgtcc tggtggctgt    4140
tggcagcaga ttcaggtgcc tctgccccac gcggtgtcct ggagaagccc gtgggatgag    4200
aggccctgga tggtagatcg gccatgctcc gccccagagg cagaattcgt ctgggctttt    4260
aggcttgctg ctagccctg gggggcgcctg gagccacagt gggtgtctgt acacacatac    4320
acactcaaaa ggggccagtg cccctgggca cggcggcccc caccctctgc cctgcctgcc    4380
tggcctcgga ggacccgcat gccccatccg gcagctcctc cggtgtgctc acaggacact    4440
taaaccagga cgaggcatgg ccccgagaca ctggcaggtt tgtgagcctc ttcccacccc    4500
ctgtgccccc acccttgcct ggttcctggt ggctcagggc aaggagtggc cctgggcgcc    4560
cgtgtcggtc ctgtttccgc tgcccttatc tcaaagtccg tggctgtttc cccttcactg    4620
actcagctag acccgtaagc ccaccctttcc cacaggaac aggctgctcc cacctgggtc    4680
ccgctgtggc cacggtgggc agcccaaaag atcaggggtg gaggggcttc caggctgtac    4740
tcctgccccg tgggcccccgt tctagaggtg cccttggcag gaccgtgcag gcagctcccc    4800 tctgtgggc agtatctggt cctgtgcccc agctgccaaa ggagagtggg ggccatgccc    4860
cgcagtcagt gttgggggggc tcctgcctac agggagaggg atggtgggga aggggtggag    4920
ctgggggcag ggcagcacag ggaatatttt tgtaactaac taactgctgt ggttggagcg    4980
aatggaagtt gggtgatttt aagttattgt tgccaaagag atgtaaagtt tattgttgct    5040 tcgcagggg atttgtttg tgttttgttt gaggcttaga acgctggtgc aatgttttct    5100
tgttccttgt ttttaagag aaatgaagct aagaaaaaag                            5140
```

<210> SEQ ID NO 15
<211> LENGTH: 5140
<212> TYPE: DNA
<213> ORGANISM: Homo sapiens
<220> FEATURE:
<221> NAME/KEY: CDS
<222> LOCATION: (413)..(4036)

<400> SEQUENCE: 15

```
ctccagacct acccagaaag atgcccggat ggatcctgca gctccgtggc ttttctggga     60
agcagcggcc cctgctctca agagaccctg gctcctgatg gtggccccaa ggttgccagc    120
tggtgctagg gactcaggac agtttcccag aaaaggccaa gcgggcagcc cctccagggg    180
ccgggtgagg aagctggggg gtgcggaggc cacactgggt ccctgaaccc cctgcttggt    240
tacagtgcag ctcctcaagt ccacagacgt gggccggcac agcctcctgt acctgaagga    300
aatcggccgt ggctggttcg ggaaggtgtt cctggggga gtgaactctg gcatcagcag    360
tgcccaggtg gtggtgaagg agctgcaggc tagtgccagc gtgcaggagc ag atg cag    418
                                                           Met Gln
                                                             1 ttc ctg gag gag gtg cag ccc tac agg gcc ctg aag cac agc aac ctg      466
```

```
                Phe Leu Glu Glu Val Gln Pro Tyr Arg Ala Leu Lys His Ser Asn Leu
                                 5                  10                  15 ctc cag tgc ctg gcc cag tgc gcc gag gtg acg ccc tac ctg ctg gtg              514
Leu Gln Cys Leu Ala Gln Cys Ala Glu Val Thr Pro Tyr Leu Leu Val
             20                  25                  30 atg gag ttc tgc cca ctg ggg gac ctc aag ggc tac ctg cgg agc tgc              562
Met Glu Phe Cys Pro Leu Gly Asp Leu Lys Gly Tyr Leu Arg Ser Cys
 35                  40                  45                  50 cgg gtg gcg gag tcc atg gct ccc gac ccc cgg acc ctg cag cgc atg              610
Arg Val Ala Glu Ser Met Ala Pro Asp Pro Arg Thr Leu Gln Arg Met
                     55                  60                  65 gcc tgt gag gtg gcc tgt ggc gtc ctg cac ctt cat cgc aac aat ttc              658
Ala Cys Glu Val Ala Cys Gly Val Leu His Leu His Arg Asn Asn Phe
                 70                  75                  80 gtg cac agc gac ctg gcc ctg cgg aac tgc ctg ctc acg gct gac ctg              706
Val His Ser Asp Leu Ala Leu Arg Asn Cys Leu Leu Thr Ala Asp Leu
             85                  90                  95 acg gtg aag att ggt gac tat ggc ctg gct cac tgc aag tac aga gag              754
Thr Val Lys Ile Gly Asp Tyr Gly Leu Ala His Cys Lys Tyr Arg Glu
        100                 105                 110 gac tac ttc gtg act gcc gac cag ctg tgg gtg cct ctg cgc tgg atc              802
Asp Tyr Phe Val Thr Ala Asp Gln Leu Trp Val Pro Leu Arg Trp Ile
115                 120                 125                 130 gcg cca gag ctg gtg gac gag gtg cat agc aac ctg ctc gtc gtg gac              850
Ala Pro Glu Leu Val Asp Glu Val His Ser Asn Leu Leu Val Val Asp
                         135                 140                 145 cag acc aag agc ggg aat gtg tgg tcc ctg ggc gtg acc atc tgg gag              898
Gln Thr Lys Ser Gly Asn Val Trp Ser Leu Gly Val Thr Ile Trp Glu
                 150                 155                 160 ctc ttt gag ctg ggc acg cag ccc tat ccc cag cac tcg gac cag cag              946
Leu Phe Glu Leu Gly Thr Gln Pro Tyr Pro Gln His Ser Asp Gln Gln
         165                 170                 175 gtg ctg gcg tac acg gtc cgg gag cag cag ctc aag ctg ccc aag ccc              994
Val Leu Ala Tyr Thr Val Arg Glu Gln Gln Leu Lys Leu Pro Lys Pro
     180                 185                 190 cag ctg cag ctg acc ctg tcg gac cgc tgg tac gag gtg atg cag ttc             1042
Gln Leu Gln Leu Thr Leu Ser Asp Arg Trp Tyr Glu Val Met Gln Phe
195                 200                 205                 210 tgc tgg ctg cag ccc gag cag cgg ccc aca gcc gag gag gtg cac ctg             1090
Cys Trp Leu Gln Pro Glu Gln Arg Pro Thr Ala Glu Glu Val His Leu
                 215                 220                 225 ctg ctg tcc tac ctg tgt gcc aag ggc gcc acc gaa gca gag gag gag             1138
Leu Leu Ser Tyr Leu Cys Ala Lys Gly Ala Thr Glu Ala Glu Glu Glu
             230                 235                 240 ttt gaa cgg cgc tgg cgc tct ctg cgg ccc ggc ggg ggc ggc gtg ggg             1186
Phe Glu Arg Arg Trp Arg Ser Leu Arg Pro Gly Gly Gly Gly Val Gly
         245                 250                 255 ccc ggg ccc ggt gcg gcg ggg ccc atg ctg ggc ggc gtg gtg gag ctc             1234
Pro Gly Pro Gly Ala Ala Gly Pro Met Leu Gly Gly Val Val Glu Leu
 260                 265                 270 gcc gct gcc tcg tcc ttc ccg ctg ctg gag cag ttc gcg ggc gac ggc             1282
Ala Ala Ala Ser Ser Phe Pro Leu Leu Glu Gln Phe Ala Gly Asp Gly
275                 280                 285                 290 ttc cac gcg gac ggc gac gac gtg ctg acg gtg acc gag acc agc cga             1330
Phe His Ala Asp Gly Asp Asp Val Leu Thr Val Thr Glu Thr Ser Arg
                         295                 300                 305 ggc ctc aat ttt gag tac aag tgg gag gcg ggc cgc ggc gcg gag gcc             1378
Gly Leu Asn Phe Glu Tyr Lys Trp Glu Ala Gly Arg Gly Ala Glu Ala
                 310                 315                 320
```

```
                                                           -continued
ttc ccg gcc acg ctg agc cct ggc cgc acc gca cgc ctg cag gag ctg         1426
Phe Pro Ala Thr Leu Ser Pro Gly Arg Thr Ala Arg Leu Gln Glu Leu
            325                 330                 335 tgc gcc ccc gac ggc gcg ccc ccg ggc gtg gtt ccg gtg ctc agc gcg         1474
Cys Ala Pro Asp Gly Ala Pro Pro Gly Val Val Pro Val Leu Ser Ala
340                 345                 350 cac agc ccg tcg ctg ggc agc gag tac ttc atc cgc cta gag gag gcc         1522
His Ser Pro Ser Leu Gly Ser Glu Tyr Phe Ile Arg Leu Glu Glu Ala
355                 360                 365                 370 gca ccc gcc gcc ggc cac gac cct gac tgc gcc ggc tgc gcc ccc agt         1570
Ala Pro Ala Ala Gly His Asp Pro Asp Cys Ala Gly Cys Ala Pro Ser
                375                 380                 385 cca cct gcc acc gcg gac cag gac gac gac tct gac ggc agc acc gcc         1618
Pro Pro Ala Thr Ala Asp Gln Asp Asp Asp Ser Asp Gly Ser Thr Ala
            390                 395                 400 gcc tcg ctg gcc atg gag ccg ctg ctg ggc cac ggg cca ccc gtc gac         1666
Ala Ser Leu Ala Met Glu Pro Leu Leu Gly His Gly Pro Pro Val Asp
        405                 410                 415 gtc ccc tgg ggc cgc ggc gac cac tac cct cgc aga agc ttg gcg cgg         1714
Val Pro Trp Gly Arg Gly Asp His Tyr Pro Arg Arg Ser Leu Ala Arg
    420                 425                 430 gac ccg ctc tgc ccc tca cgc tct ccc tcg ccc tcg gcg ggg ccc ctg         1762
Asp Pro Leu Cys Pro Ser Arg Ser Pro Ser Pro Ser Ala Gly Pro Leu
435                 440                 445                 450 agt ctg gcg gag gga gga gcg gag gat gca gac tgg ggc gtg gcc gcc         1810
Ser Leu Ala Glu Gly Gly Ala Glu Asp Ala Asp Trp Gly Val Ala Ala
                455                 460                 465 ttc tgt cct gcc ttc ttc gag gac cca ctg ggc acg tcc cct ttg ggg         1858
Phe Cys Pro Ala Phe Phe Glu Asp Pro Leu Gly Thr Ser Pro Leu Gly
            470                 475                 480 agc tca ggg gcg ccc ccg ctg ccg ctg act ggc gag gat gag cta gag         1906
Ser Ser Gly Ala Pro Pro Leu Pro Leu Thr Gly Glu Asp Glu Leu Glu
        485                 490                 495 gag gtg gga gcg cgg agg gcc gcc cag cgc ggg cac tgg cgc tcc aac         1954
Glu Val Gly Ala Arg Arg Ala Ala Gln Arg Gly His Trp Arg Ser Asn
    500                 505                 510 gtg tca gcc aac aac aac agc ggc agc cgc tgt cca gag tcc tgg gac         2002
Val Ser Ala Asn Asn Asn Ser Gly Ser Arg Cys Pro Glu Ser Trp Asp
515                 520                 525                 530 ccc gtc tct gcg ggc tgc cac gct gag ggc tgc ccc agt cca aag cag         2050
Pro Val Ser Ala Gly Cys His Ala Glu Gly Cys Pro Ser Pro Lys Gln
                535                 540                 545 acc cca cgg gcc tcc ccc gag ccg ggg tac cct gga gag cct ctg ctt         2098
Thr Pro Arg Ala Ser Pro Glu Pro Gly Tyr Pro Gly Glu Pro Leu Leu
            550                 555                 560 ggg ctc cag gca gcc tct gcc cag gag cca ggc tgc tgc ccc ggc ctc         2146
Gly Leu Gln Ala Ala Ser Ala Gln Glu Pro Gly Cys Cys Pro Gly Leu
        565                 570                 575 cct cat cta tgc tct gcc cag ggc ctg gca cct gct ccc tgc ctg gtt         2194
Pro His Leu Cys Ser Ala Gln Gly Leu Ala Pro Ala Pro Cys Leu Val
    580                 585                 590 aca ccc tcc tgg aca gag aca gcc agt agt ggg ggt gac cac ccg cag         2242
Thr Pro Ser Trp Thr Glu Thr Ala Ser Ser Gly Gly Asp His Pro Gln
595                 600                 605                 610 gca gag ccc aag ctt gcc acg gag gct gag ggc act acc gga ccc cgc         2290
Ala Glu Pro Lys Leu Ala Thr Glu Ala Glu Gly Thr Thr Gly Pro Arg
                615                 620                 625 ctg ccc ctt cct tcc gtc ccc tcc cca tcc cag gag gga gcc cca ctt         2338
Leu Pro Leu Pro Ser Val Pro Ser Pro Ser Gln Glu Gly Ala Pro Leu
            630                 635                 640
```

```
ccc tcg gag gag gcc agt gcc ccc gac gcc cct gat gcc ctg cct gac   2386
Pro Ser Glu Glu Ala Ser Ala Pro Asp Ala Pro Asp Ala Leu Pro Asp
            645                 650                 655 tct ccc acg cct gct act ggt ggc gag gtg tct gcc atc aag ctg gct   2434
Ser Pro Thr Pro Ala Thr Gly Gly Glu Val Ser Ala Ile Lys Leu Ala
    660                 665                 670 tct gcc ctg aat ggc agc agc agc tct ccc gag gtg gag gca ccc agc   2482
Ser Ala Leu Asn Gly Ser Ser Ser Ser Pro Glu Val Glu Ala Pro Ser
675                 680                 685                 690 agt gag gat gag gac acg gct gag gcc acc tca ggc atc ttc acc gac   2530
Ser Glu Asp Glu Asp Thr Ala Glu Ala Thr Ser Gly Ile Phe Thr Asp
                695                 700                 705 acg tcc agc gac ggc ctg cag gcc agg agg ccg gat gtg gtg cca gcc   2578
Thr Ser Ser Asp Gly Leu Gln Ala Arg Arg Pro Asp Val Val Pro Ala
            710                 715                 720 ttc cgc tct ctg cag aag cag gtg ggg acc ccc gac tcc ctg gac tcc   2626
Phe Arg Ser Leu Gln Lys Gln Val Gly Thr Pro Asp Ser Leu Asp Ser
        725                 730                 735 ctg gac atc ccg tcc tca gcc agt gat ggt ggc tat gag gtc ttc agc   2674
Leu Asp Ile Pro Ser Ser Ala Ser Asp Gly Gly Tyr Glu Val Phe Ser
740                 745                 750 ccg tcg gcc act ggc ccc tct gga ggg cag ccg cga gcg ctg gac agt   2722
Pro Ser Ala Thr Gly Pro Ser Gly Gly Gln Pro Arg Ala Leu Asp Ser
755                 760                 765                 770 ggc tat gac acc gag aac tat gag tcc cct gag ttt gtg ctc aag gag   2770
Gly Tyr Asp Thr Glu Asn Tyr Glu Ser Pro Glu Phe Val Leu Lys Glu
                775                 780                 785 gcg cag gaa ggg tgt gag ccc cag gcc ttt gcg gag ctg gcc tca gag   2818
Ala Gln Glu Gly Cys Glu Pro Gln Ala Phe Ala Glu Leu Ala Ser Glu
            790                 795                 800 ggt gag ggc ccc ggg ccc gag aca cgg ctc tcc acc tcc ctc agt ggc   2866
Gly Glu Gly Pro Gly Pro Glu Thr Arg Leu Ser Thr Ser Leu Ser Gly
        805                 810                 815 ctc aac gag aag aat ccc tac cga gac tct gcc tac ttc tca gac ctc   2914
Leu Asn Glu Lys Asn Pro Tyr Arg Asp Ser Ala Tyr Phe Ser Asp Leu
820                 825                 830 gag gct gag gcc gag gcc acc tca ggc cca gag aag aag tgc ggc ggg   2962
Glu Ala Glu Ala Glu Ala Thr Ser Gly Pro Glu Lys Lys Cys Gly Gly
835                 840                 845                 850 gac cga gcc ccc ggg cca gag ctg ggc ctg ccg agc act ggg cag ccg   3010
Asp Arg Ala Pro Gly Pro Glu Leu Gly Leu Pro Ser Thr Gly Gln Pro
                855                 860                 865 tct gag cag gtc tgt ctc agg cct ggg gtt tcc ggg gag gca caa ggc   3058
Ser Glu Gln Val Cys Leu Arg Pro Gly Val Ser Gly Glu Ala Gln Gly
            870                 875                 880 tct ggc ccc ggg gag gtg ctg ccc cca ctg ctg cag ctt gaa ggg tcc   3106
Ser Gly Pro Gly Glu Val Leu Pro Pro Leu Leu Gln Leu Glu Gly Ser
        885                 890                 895 tcc cca gag ccc agc acc tgc ccc tcg ggc ctg gtc cca gag cct ccg   3154
Ser Pro Glu Pro Ser Thr Cys Pro Ser Gly Leu Val Pro Glu Pro Pro
900                 905                 910 gag ccc caa ggc cca gcc aag gtg cgg cct ggg ccc agc ccc agc tgc   3202
Glu Pro Gln Gly Pro Ala Lys Val Arg Pro Gly Pro Ser Pro Ser Cys
915                 920                 925                 930 tcc cag ttt ttc ctg acc ccg gtt ccg ctg aga tca gaa ggc aac       3250
Ser Gln Phe Phe Leu Thr Pro Val Pro Leu Arg Ser Glu Gly Asn
                935                 940                 945 agc tct gag ttc cag ggg ccc cca gga ctg ttg tca ggg ccg gcc cca   3298
Ser Ser Glu Phe Gln Gly Pro Pro Gly Leu Leu Ser Gly Pro Ala Pro
```

-continued

```
              950           955           960
caa aag cgg atg ggg ggc cca ggc acc ccc aga gcc cca ctc cgc ctg        3346
Gln Lys Arg Met Gly Gly Pro Gly Thr Pro Arg Ala Pro Leu Arg Leu
        965               970               975 gct ctg ccc ggc ctc cct gcg gcc ttg gag ggc cgg ccg gag gag gag        3394
Ala Leu Pro Gly Leu Pro Ala Ala Leu Glu Gly Arg Pro Glu Glu Glu
    980               985               990 gag gag gac agt gag gac agc gac gag tct gac gag gag ctc cgc tgc        3442
Glu Glu Asp Ser Glu Asp Ser Asp Glu Ser Asp Glu Glu Leu Arg Cys
995               1000              1005              1010 tac agc gtc cag gag cct agc gag gac agc gaa gag gag gcg ccg gcg        3490
Tyr Ser Val Gln Glu Pro Ser Glu Asp Ser Glu Glu Ala Pro Ala
            1015              1020              1025 gtg ccc gtg gtg gtg gct gag agc cag agc gcg cgc aac ctg cgc agc        3538
Val Pro Val Val Val Ala Glu Ser Gln Ser Ala Arg Asn Leu Arg Ser
        1030              1035              1040 ctg ctc aag atg ccc agc ctg ctg tcc gag acc ttc tgc gag gac ctg        3586
Leu Leu Lys Met Pro Ser Leu Leu Ser Glu Thr Phe Cys Glu Asp Leu
    1045              1050              1055 gaa cgc aag aag aag gcc gtg tcc ttc ttc gac gac gtc acc gtc tac        3634
Glu Arg Lys Lys Lys Ala Val Ser Phe Phe Asp Asp Val Thr Val Tyr
1060              1065              1070 ctc ttt gac cag gaa agc ccc acc cgg gag ctc ggg gag ccc ttc ccg        3682
Leu Phe Asp Gln Glu Ser Pro Thr Arg Glu Leu Gly Glu Pro Phe Pro
1075              1080              1085              1090 ggc gcc aag gaa tcg ccc cct acg ttc ctt agg ggg agc ccc ggc tct        3730
Gly Ala Lys Glu Ser Pro Pro Thr Phe Leu Arg Gly Ser Pro Gly Ser
        1095              1100              1105 ccc agc gcc ccc aac cgg ccg cag cag gct gat ggc tcc cca aat ggc        3778
Pro Ser Ala Pro Asn Arg Pro Gln Gln Ala Asp Gly Ser Pro Asn Gly
    1110              1115              1120 tcc aca gcg gaa gag ggt ggt ggg ttc gcg tgg gac gac gac ttc ccg        3826
Ser Thr Ala Glu Glu Gly Gly Gly Phe Ala Trp Asp Asp Asp Phe Pro
1125              1130              1135 ctg atg acg gcc aag gca gcc ttc gcc atg gcc cta gac ccg gcc gca        3874
Leu Met Thr Ala Lys Ala Ala Phe Ala Met Ala Leu Asp Pro Ala Ala
    1140              1145              1150 ccc gcc ccg gct gcg ccc acg ccc acg ccc gct ccc ttc tcg cgc ttc        3922
Pro Ala Pro Ala Ala Pro Thr Pro Thr Pro Ala Pro Phe Ser Arg Phe
1155              1160              1165              1170 acg gtg tcg ccc gcg ccc acg tcc cgc ttc tcc atc acg cac gtg tct        3970
Thr Val Ser Pro Ala Pro Thr Ser Arg Phe Ser Ile Thr His Val Ser
        1175              1180              1185 gac tcg gac gcc gag tcc aag aga gga cct gaa gct ggt gcc ggg ggt        4018
Asp Ser Asp Ala Glu Ser Lys Arg Gly Pro Glu Ala Gly Ala Gly Gly
    1190              1195              1200 gag agt aaa gag gct tga gacctgggca gctcctgccc ctcaaggctg              4066
Glu Ser Lys Glu Ala
        1205 gcgtcaccgg agcccctgcc aggcagcagc gaggatggtg accgagaagg tggggaccac      4126 gtcctggtgg ctgttggcag cagattcagg tgcctctgcc ccacgcggtg tcctggagaa      4186 gcccgtggga tgagaggccc tggatggtag atcggccatg ctccgcccca gaggcagaat      4246 tcgtctgggc ttttaggctt gctgctagcc cctgggggcg cctggagcca cagtgggtgt      4306 ctgtacacac atacacactc aaaaggggca agtgccctg gcacggcgg ccccaccct         4366 ctgccctgcc tgcctggcct cggaggaccc gcatgcccca tccggcagct cctccggtgt      4426
```

-continued

```
gctcacagga cacttaaacc aggacgaggc atggccccga gacactggca ggtttgtgag    4486
cctcttccca cccctgtgc ccccacccct gcctggttcc tggtggctca gggcaaggag    4546
tggccctggg cgcccgtgtc ggtcctgttt ccgctgccct tatctcaaag tccgtggctg    4606
tttccccttc actgactcag ctagacccgt aagcccaccc ttcccacagg gaacaggctg    4666
ctcccacctg ggtcccgctg tggccacggt gggcagccca aaagatcagg ggtggagggg    4726
cttccaggct gtactcctgc cccgtgggcc ccgttctaga ggtgcccttg gcaggaccgt    4786
gcaggcagct cccctctgtg gggcagtatc tggtcctgtg ccccagctgc caaaggagag    4846
tgggggccat gccccgcagt cagtgttggg gggctcctgc ctacagggag agggatggtg    4906 gggaagggt ggagctgggg gcagggcagc acagggaata tttttgtaac taactaactg    4966
ctgtggttgg agcgaatgga agttgggtga ttttaagtta ttgttgccaa agagatgtaa    5026
agtttattgt tgcttcgcag ggggatttgt tttgtgtttt gtttgaggct tagaacgctg    5086
gtgcaatgtt ttcttgttcc ttgtttttta agagaaatga agctaagaaa aaag         5140
```

<210> SEQ ID NO 16
<211> LENGTH: 1207
<212> TYPE: PRT
<213> ORGANISM: Homo sapiens

<400> SEQUENCE: 16

```
Met Gln Phe Leu Glu Glu Val Gln Pro Tyr Arg Ala Leu Lys His Ser
  1               5                  10                  15

Asn Leu Leu Gln Cys Leu Ala Gln Cys Ala Glu Val Thr Pro Tyr Leu
             20                  25                  30

Leu Val Met Glu Phe Cys Pro Leu Gly Asp Leu Lys Gly Tyr Leu Arg
         35                  40                  45

Ser Cys Arg Val Ala Glu Ser Met Ala Pro Asp Pro Arg Thr Leu Gln
     50                  55                  60

Arg Met Ala Cys Glu Val Ala Cys Gly Val Leu His Leu His Arg Asn
 65                  70                  75                  80

Asn Phe Val His Ser Asp Leu Ala Leu Arg Asn Cys Leu Leu Thr Ala
                 85                  90                  95

Asp Leu Thr Val Lys Ile Gly Asp Tyr Gly Leu Ala His Cys Lys Tyr
            100                 105                 110

Arg Glu Asp Tyr Phe Val Thr Ala Asp Gln Leu Trp Val Pro Leu Arg
        115                 120                 125

Trp Ile Ala Pro Glu Leu Val Asp Glu Val His Ser Asn Leu Leu Val
    130                 135                 140

Val Asp Gln Thr Lys Ser Gly Asn Val Trp Ser Leu Gly Val Thr Ile
145                 150                 155                 160

Trp Glu Leu Phe Glu Leu Gly Thr Gln Pro Tyr Pro Gln His Ser Asp
                165                 170                 175

Gln Gln Val Leu Ala Tyr Thr Val Arg Glu Gln Leu Lys Leu Pro
            180                 185                 190

Lys Pro Gln Leu Gln Leu Thr Leu Ser Asp Arg Trp Tyr Glu Val Met
        195                 200                 205

Gln Phe Cys Trp Leu Gln Pro Glu Gln Arg Pro Thr Ala Glu Glu Val
    210                 215                 220

His Leu Leu Leu Ser Tyr Leu Cys Ala Lys Gly Ala Thr Glu Ala Glu
225                 230                 235                 240

Glu Glu Phe Glu Arg Arg Trp Arg Ser Leu Arg Pro Gly Gly Gly Gly
                245                 250                 255
```

```
Val Gly Pro Gly Pro Gly Ala Ala Gly Pro Met Leu Gly Gly Val Val
            260                 265                 270

Glu Leu Ala Ala Ala Ser Ser Phe Pro Leu Leu Glu Gln Phe Ala Gly
            275                 280                 285

Asp Gly Phe His Ala Asp Gly Asp Val Leu Thr Val Thr Glu Thr
            290                 295                 300

Ser Arg Gly Leu Asn Phe Glu Tyr Lys Trp Glu Ala Gly Arg Gly Ala
305                 310                 315                 320

Glu Ala Phe Pro Ala Thr Leu Ser Pro Gly Arg Thr Ala Arg Leu Gln
                325                 330                 335

Glu Leu Cys Ala Pro Asp Gly Ala Pro Pro Gly Val Val Pro Val Leu
            340                 345                 350

Ser Ala His Ser Pro Ser Leu Gly Ser Glu Tyr Phe Ile Arg Leu Glu
            355                 360                 365

Glu Ala Ala Pro Ala Ala Gly His Asp Pro Asp Cys Ala Gly Cys Ala
            370                 375                 380

Pro Ser Pro Pro Ala Thr Ala Asp Gln Asp Asp Ser Asp Gly Ser
385                 390                 395                 400

Thr Ala Ala Ser Leu Ala Met Glu Pro Leu Leu Gly His Gly Pro Pro
                405                 410                 415

Val Asp Val Pro Trp Gly Arg Gly Asp His Tyr Pro Arg Arg Ser Leu
            420                 425                 430

Ala Arg Asp Pro Leu Cys Pro Ser Arg Ser Pro Ser Pro Ser Ala Gly
            435                 440                 445

Pro Leu Ser Leu Ala Glu Gly Ala Glu Asp Ala Asp Trp Gly Val
            450                 455                 460

Ala Ala Phe Cys Pro Ala Phe Phe Glu Asp Pro Leu Gly Thr Ser Pro
465                 470                 475                 480

Leu Gly Ser Ser Gly Ala Pro Pro Leu Pro Leu Thr Gly Glu Asp Glu
                485                 490                 495

Leu Glu Glu Val Gly Ala Arg Arg Ala Ala Gln Arg Gly His Trp Arg
            500                 505                 510

Ser Asn Val Ser Ala Asn Asn Ser Gly Ser Arg Cys Pro Glu Ser
            515                 520                 525

Trp Asp Pro Val Ser Ala Gly Cys His Ala Glu Gly Cys Pro Ser Pro
            530                 535                 540

Lys Gln Thr Pro Arg Ala Ser Pro Glu Pro Gly Tyr Pro Gly Glu Pro
545                 550                 555                 560

Leu Leu Gly Leu Gln Ala Ala Ser Ala Gln Glu Pro Gly Cys Cys Pro
                565                 570                 575

Gly Leu Pro His Leu Cys Ser Ala Gln Gly Leu Ala Pro Ala Pro Cys
            580                 585                 590

Leu Val Thr Pro Ser Trp Thr Glu Thr Ala Ser Gly Gly Asp His
            595                 600                 605

Pro Gln Ala Glu Pro Lys Leu Ala Thr Glu Ala Glu Gly Thr Thr Gly
            610                 615                 620

Pro Arg Leu Pro Leu Pro Ser Val Pro Ser Pro Ser Gln Glu Gly Ala
625                 630                 635                 640

Pro Leu Pro Ser Glu Glu Ala Ser Ala Pro Asp Ala Pro Asp Ala Leu
                645                 650                 655

Pro Asp Ser Pro Thr Pro Ala Thr Gly Gly Glu Val Ser Ala Ile Lys
            660                 665                 670
```

```
Leu Ala Ser Ala Leu Asn Gly Ser Ser Ser Pro Glu Val Glu Ala
            675                 680                 685

Pro Ser Ser Glu Asp Glu Asp Thr Ala Glu Ala Thr Ser Gly Ile Phe
690                 695                 700

Thr Asp Thr Ser Ser Asp Gly Leu Gln Ala Arg Arg Pro Asp Val Val
705                 710                 715                 720

Pro Ala Phe Arg Ser Leu Gln Lys Gln Val Gly Thr Pro Asp Ser Leu
                725                 730                 735

Asp Ser Leu Asp Ile Pro Ser Ser Ala Ser Asp Gly Gly Tyr Glu Val
            740                 745                 750

Phe Ser Pro Ser Ala Thr Gly Pro Ser Gly Gln Pro Arg Ala Leu
        755                 760                 765

Asp Ser Gly Tyr Asp Thr Glu Asn Tyr Glu Ser Pro Glu Phe Val Leu
        770                 775                 780

Lys Glu Ala Gln Glu Gly Cys Glu Pro Gln Ala Phe Ala Glu Leu Ala
785                 790                 795                 800

Ser Glu Gly Glu Gly Pro Gly Pro Glu Thr Arg Leu Ser Thr Ser Leu
                805                 810                 815

Ser Gly Leu Asn Glu Lys Asn Pro Tyr Arg Asp Ser Ala Tyr Phe Ser
            820                 825                 830

Asp Leu Glu Ala Glu Ala Glu Ala Thr Ser Gly Pro Glu Lys Lys Cys
        835                 840                 845

Gly Gly Asp Arg Ala Pro Gly Pro Glu Leu Gly Leu Pro Ser Thr Gly
850                 855                 860

Gln Pro Ser Glu Gln Val Cys Leu Arg Pro Gly Val Ser Gly Glu Ala
865                 870                 875                 880

Gln Gly Ser Gly Pro Gly Glu Val Leu Pro Leu Leu Gln Leu Glu
                885                 890                 895

Gly Ser Ser Pro Glu Pro Ser Thr Cys Pro Ser Gly Leu Val Pro Glu
                    900                 905                 910

Pro Pro Glu Pro Gln Gly Pro Ala Lys Val Arg Pro Gly Pro Ser Pro
        915                 920                 925

Ser Cys Ser Gln Phe Phe Leu Leu Thr Pro Val Pro Leu Arg Ser Glu
        930                 935                 940

Gly Asn Ser Ser Glu Phe Gln Gly Pro Pro Gly Leu Leu Ser Gly Pro
945                 950                 955                 960

Ala Pro Gln Lys Arg Met Gly Gly Pro Gly Thr Pro Arg Ala Pro Leu
                965                 970                 975

Arg Leu Ala Leu Pro Gly Leu Pro Ala Ala Leu Glu Gly Arg Pro Glu
            980                 985                 990

Glu Glu Glu Glu Asp Ser Glu Asp Ser Asp Ser Asp Glu Glu Leu
        995                 1000                1005

Arg Cys Tyr Ser Val Gln Glu Pro Ser Glu Asp Ser Glu Glu Ala
    1010                1015                1020

Pro Ala Val Pro Val Val Ala Glu Ser Gln Ser Ala Arg Asn Leu
1025                1030                1035                1040

Arg Ser Leu Leu Lys Met Pro Ser Leu Leu Ser Glu Thr Phe Cys Glu
                1045                1050                1055

Asp Leu Glu Arg Lys Lys Lys Ala Val Ser Phe Phe Asp Asp Val Thr
            1060                1065                1070

Val Tyr Leu Phe Asp Gln Glu Ser Pro Thr Arg Glu Leu Gly Glu Pro
        1075                1080                1085

Phe Pro Gly Ala Lys Glu Ser Pro Pro Thr Phe Leu Arg Gly Ser Pro
```

```
              1090              1095              1100
Gly Ser Pro Ser Ala Pro Asn Arg Pro Gln Gln Ala Asp Gly Ser Pro
1105                1110                1115                1120

Asn Gly Ser Thr Ala Glu Glu Gly Gly Gly Phe Ala Trp Asp Asp Asp
                1125                1130                1135

Phe Pro Leu Met Thr Ala Lys Ala Ala Phe Ala Met Ala Leu Asp Pro
            1140                1145                1150

Ala Ala Pro Ala Pro Ala Ala Pro Thr Pro Thr Pro Ala Pro Phe Ser
        1155                1160                1165

Arg Phe Thr Val Ser Pro Ala Pro Thr Ser Arg Phe Ser Ile Thr His
    1170                1175                1180

Val Ser Asp Ser Asp Ala Glu Ser Lys Arg Gly Pro Glu Ala Gly Ala
1185                1190                1195                1200

Gly Gly Glu Ser Lys Glu Ala
            1205

<210> SEQ ID NO 17
<211> LENGTH: 1803
<212> TYPE: DNA
<213> ORGANISM: Pan troglodytes

<400> SEQUENCE: 17
gctccctgcc tggttacacc ctcctggaca gagacagccg gtagtggggg tgaccacccg      60
caggcagagc ccaagcttgc cacggaggct gagggcactg ccggaccctg tctgcccctt     120
ccttccgtcc cctccccatc caggaggga gccccacttc cctcggagga ggccagtgcc      180
cctgacgccc ctgatgccct gcctgactct cccatgcctg ctactggtgg cgaggtgtct     240
gccatcaagc tggcttctgt cctgaatggc agcagcagct ccccgaggt ggaggcaccc      300 agcagcgagg atgaggacac ggctgaggcc acctcaggca tcttcaccga cacgtccagc     360
gacggcctgc aggccgagag gctggatgtg gtgccagcct ccgctctct gcagaagcag      420 gtggggaccc ccgactccct ggactccctg acatcccat cctcagccag tgatggtggc      480
tatgaggtct tcagcccgtc ggccactggc ccctctggag gcagccccg agcgctggac      540 agtggctatg acaccgagaa ctatgagtcc cctgagtttg tgctcaagga ggcgcaggaa     600
gggtgtgagc ccaggccctt tgaggagctg gcctcagagg gtgagggccc cggccccggg     660
cccgagacgc ggctctccac ctccctcagt ggcctcaacg agaagaatcc ctaccgagac     720
tctgcctact ctcagacctg gaggctgag gccgaggccg aggccacctc aggcccagag      780
aagaagtgcg gcggggacca agccccgggg ccagagctgg acctgccgag cactgggcag     840
ccgtctgagc aggtctccct caggcctggg gtttccgggg aggcacaagg ctctggcccc     900
ggggaggtgc tgcccccact gctgcggctt gaaggatcct cccagagcc cagcacctgc      960 ccctcgggcc tggtcccaga gcctccggag cccaaggcc cagccgaggt gcggcctggg     1020
cccagcccca gctgctccca gttttttcctg ctgaccccgg ttccgctgag atcagaaggc    1080
aacagctctg agttccaggg gcccccagga ctgttgtcag gccggcccc acaaaagcgg     1140 atggggggcc taggcacccc cagagcccca ctccgcctgg ctctgcccgg cctccctgcg    1200
gccttggagg ccggccgga ggaggagag gaggacagtg aggacagcgg cgagtctgac     1260
gaggagctcc gctgctacag cgtccaggag cctagcgagg acagcgaaga ggaggcgccg     1320
gcggtgcccg tggtggtggc tgagagccag agcgcgcgca acctgcgcag cctgctcaag    1380
atgcccagcc tgctgtccga ggccttctgc gaggacctgg aacgcaagaa gaaggccgtg    1440
```

```
tccttcttcg acgacgtcac cgtctacctc tttgaccagg aaagccccac ctgggagctc    1500
ggggagccct tcccgggcgc caaggaatcg ccccccacgt tccttagggg gagcccggc     1560 tctcccagcg cccccaaccg gccgcagcag gctgatggct ccccaaatgg ctccacagcg    1620
gaagagggtg gtgggttcgc gtgggacgac gacttcccgc tgatgccggc caaggcagcc    1680
ttcgccatgg ccctagaccc ggccgcaccc gccccggctg cgcccacgcc cgctcccttc    1740
tcgcgcttca cggtgtcgcc cgcgcccacg tccacgtccc gcttctccat cacgcacgtg    1800
tct                                                                  1803

<210> SEQ ID NO 18
<211> LENGTH: 1785
<212> TYPE: DNA
<213> ORGANISM: Gorilla gorilla

<400> SEQUENCE: 18
gctccctgcc tggttacacc ctcctggaca gagacagacg gtagtggggg tgaccacccg      60
caggcagagc ccaagcttgc cacggaggct gagggcactg ccggaccccg cctgcccctt    120
ccttccgtcc cctccccatc ccaggaggga gccccacttc cctcggagga ggccagtgcc    180
cccgacgccc ctgatgccct gcctgactcg cccacgcctg ctactggtgg cgaggtgtct    240
gccaccaagc tggcttccgc cctgaatggc agcagcagct cccgaggt ggaggcaccc     300 agcagtgagg atgaggacac ggctgaggca acctcaggca tcttcaccga cacgtccagc    360
gacggcctgc aggccgagag gcaggatgtg gtgccagcct tccactctct gcagaagcag    420
gtggggaccc ccgactccct ggactccctg gacatcccgt cctcagccag tgatggtggc    480
tatgaggtct tcagcccgtc ggccacgggc ccctctggag ggcagcccg agcgctggac    540 agtggctatg acaccgagaa ctatgagtcc cctgagtttg tgctcaagga ggcgcaggaa    600
gggtgtgagc cccaggcctt tgcggagctg gcctcagagg gcgagggccc cgggcccgag    660
acgcggctct ccacctccct cagtggcctc aacgagaaga atccctaccg agattctgcc    720
tacttctcag acctggaggc tgaggccgag gctacctcag gcccagagaa gaagtgcggt    780
ggggaccaag ccccgggcc agagctgggc ctgccgagca ctgggcagcc gtctgagcag    840
gtctccctca gtcctggggt ttccgtggag gcacaaggct ctggccccgg ggaggtgctg    900
cccccactgc tgcggcttga agggtcctcc ccagagccca gcacctgccc ctcgggcctg    960
gtcccagagc ctccggagcc ccaaggccca gccgaggtgc ggcctgggcc cagccccagc   1020
tgctcccagt ttttcctgct gaccccggtt ccgctgagat cagaaggcaa cagctctgag   1080
ttccaggggc ccccaggact gttgtcaggg ccggccccac aaaagcggat gggggggccca   1140 ggcaccccca gagccccaca ccgcctggct ctgcccggcc tccctgcggc cttggagggc   1200 cggccgagg aggaggagga ggacagtgag gacagcgacg agtctgacga ggagctccgc   1260
tgctacagcg tccaggagcc tagcgaggac agcgaagagg aggcgccggc ggtgcccgtg   1320
gtggtggctg agagccagag cgcgcgcaac ctgcgcagcc tgctcaagat gcccagcctg   1380
ctgtccgagg ccttctgcga ggacctggaa cgcaagaaga aggccgtgtc cttcttcgac   1440
gacgtcaccg tctacctctt tgaccaggaa agccccaccc gggagctcgg ggagcccttc   1500
ccgggcgcca aggaatcgcc cccacgttc cttaggggga gccccggctc ttccagcgcc    1560
cccaaccggc cgcagcaggc tgatggctcc ccaaatggct ccacagcgga gagggtggt    1620 gggttcgcgt gggacgacga cttcccgctg atgccggca aggcagcctt cgccatggcc    1680
ctagacccgg ccgcacccgc cccggctgcg cccacgcccg ctcccttctc gcgcttcacg    1740
```

-continued

```
gtgtcgcccg cgcccacgtc ccgcttctcc atcacgcacg tgtct              1785
```

<210> SEQ ID NO 19
<211> LENGTH: 24
<212> TYPE: DNA
<213> ORGANISM: Pan troglodytes

<400> SEQUENCE: 19

```
ggtgagggcc ccggccccgg gccc                                      24
```

<210> SEQ ID NO 20
<211> LENGTH: 18
<212> TYPE: DNA
<213> ORGANISM: Homo sapiens

<400> SEQUENCE: 20

```
ggtgagggcc ccgggccc                                             18
```

<210> SEQ ID NO 21
<211> LENGTH: 18
<212> TYPE: DNA
<213> ORGANISM: Gorilla gorilla

<400> SEQUENCE: 21

```
ggcgagggcc ccgggccc                                             18
```

<210> SEQ ID NO 22
<211> LENGTH: 24
<212> TYPE: DNA
<213> ORGANISM: Pan troglodytes

<400> SEQUENCE: 22

```
ctggaggctg aggccgaggc cgag                                      24
```

<210> SEQ ID NO 23
<211> LENGTH: 18
<212> TYPE: DNA
<213> ORGANISM: Homo sapiens

<400> SEQUENCE: 23

```
ctcgaggctg aggccgag                                             18
```

<210> SEQ ID NO 24
<211> LENGTH: 18
<212> TYPE: DNA
<213> ORGANISM: Gorilla gorilla

<400> SEQUENCE: 24

```
ctggaggctg aggccgag                                             18
```

<210> SEQ ID NO 25
<211> LENGTH: 18
<212> TYPE: DNA
<213> ORGANISM: Pan troglodytes

<400> SEQUENCE: 25

```
cccacgcccg ctcccttc                                             18
```

<210> SEQ ID NO 26
<211> LENGTH: 24
<212> TYPE: DNA
<213> ORGANISM: Homo sapiens

```
-continued

<400> SEQUENCE: 26
cccacgccca cgcccgctcc cttc                                          24

<210> SEQ ID NO 27
<211> LENGTH: 18
<212> TYPE: DNA
<213> ORGANISM: Gorilla gorilla

<400> SEQUENCE: 27
cccacgcccg ctcccttc                                                 18

<210> SEQ ID NO 28
<211> LENGTH: 24
<212> TYPE: DNA
<213> ORGANISM: Pan troglodytes

<400> SEQUENCE: 28
cccacgtcca cgtcccgctt ctcc                                          24

<210> SEQ ID NO 29
<211> LENGTH: 18
<212> TYPE: DNA
<213> ORGANISM: Homo sapiens

<400> SEQUENCE: 29
cccacgtccc gcttctcc                                                 18

<210> SEQ ID NO 30
<211> LENGTH: 18
<212> TYPE: DNA
<213> ORGANISM: Gorilla gorilla

<400> SEQUENCE: 30
cccacgtccc gcttctcc                                                 18

<210> SEQ ID NO 31
<211> LENGTH: 1335
<212> TYPE: DNA
<213> ORGANISM: Pan troglodytes

<400> SEQUENCE: 31
atggcagtga caactcgttt gacatggttg catgaaaaga tcctgcaaaa tcattttgga    60
gggaagcggc ttagccttct ctataagggt agtgtccatg gattccataa tggagttttg   120
cttgacagat gttgtaatca agggcctact ctaacagtga tttatagtga agatcatatt   180
attggagcat atgcagaaga gggttaccag gmaagaaagt atgcttccat catccttttt   240
gcacttcaag agactaaaat ttcagaatgg aaactaggac tatatacacc agaaacactg   300
ttttgttgtg acgttgcaaa atataactcc ccaactaatt tccagataga tggaagaaat   360
agaaaagtga ttatggactt aaagacaatg gaaaatcttg acttgctcaa aaattgtact   420
atctctattc aggattatga agttttcga tgcgaagatt cactggacga agaaagata    480 aaagggtca ttgagctcag gaagagctta ctgtctgcct tgagaactta tgaaccatat   540
ggatccctgg ttcaacaaat acgaattctg ctgctgggtc aattggagc tgggaagtct   600 agcttttttca actcagtgag gtctgttttc caagggcatg taacgcatca ggctttggtg   660
ggcactaata caactgggat atctgagaag tataggacat actctattag agacgggaaa   720
gatggcaaat acctgccatt tattctgtgt gactcactgg ggctgagtga aaagaaggc   780 ggcctgtgca tggatgacat atcctacatc ttgaacggta acattcgtga tagataccag   840
```

```
tttaatccca tggaatcaat caaattaaat catcatgact acattgattc cccatcgctg     900
aaggacagaa ttcattgtgt ggcatttgta tttgatgcca gctctattga atacttctcc     960
tctcagatga tagtaaagat caaaagaatt cgaagggagt tggtaaacgc tggtgtggta    1020
catgtggctt tgctcactca tgtggatagc atggatctga ttacaaaagg tgaccttata    1080
gaaatagaga gatgtgtgcc tgtgaggtcc aagctagagg aagtccaaag aaaacttgga    1140
tttgctcttt ctgacatctc ggtggttagc aattattcct ctgagtggga gctggaccct    1200
gtaaaggatg ttctaattct ttctgctctg agacgaatgc tatgggctgc agatgacttc    1260
ttagaggatt tgccttttga gcaaataggg aatctaaggg aggaaattat caactgtgca    1320
caaggaaaaa aatag                                                     1335
```

```
<210> SEQ ID NO 32
<211> LENGTH: 1335
<212> TYPE: DNA
<213> ORGANISM: Pan troglodytes
<220> FEATURE:
<221> NAME/KEY: Variation
<222> LOCATION: 212
<223> OTHER INFORMATION: M= A or C

<400> SEQUENCE: 32
```

```
atg gca gtg aca act cgt ttg aca tgg ttg cat gaa aag atc ctg caa      48
Met Ala Val Thr Thr Arg Leu Thr Trp Leu His Glu Lys Ile Leu Gln
  1               5                  10                  15 aat cat ttt gga ggg aag cgg ctt agc ctt ctc tat aag ggt agt gtc      96
Asn His Phe Gly Gly Lys Arg Leu Ser Leu Leu Tyr Lys Gly Ser Val
             20                  25                  30 cat gga ttc cat aat gga gtt ttg ctt gac aga tgt tgt aat caa ggg     144
His Gly Phe His Asn Gly Val Leu Leu Asp Arg Cys Cys Asn Gln Gly
         35                  40                  45 cct act cta aca gtg att tat agt gaa gat cat att att gga gca tat     192
Pro Thr Leu Thr Val Ile Tyr Ser Glu Asp His Ile Ile Gly Ala Tyr
     50                  55                  60 gca gaa gag ggt tac cag gma aga aag tat gct tcc atc atc ctt ttt     240
Ala Glu Glu Gly Tyr Gln Xaa Arg Lys Tyr Ala Ser Ile Ile Leu Phe
 65                  70                  75                  80 gca ctt caa gag act aaa att tca gaa tgg aaa cta gga cta tat aca     288
Ala Leu Gln Glu Thr Lys Ile Ser Glu Trp Lys Leu Gly Leu Tyr Thr
                 85                  90                  95 cca gaa aca ctg ttt tgt tgt gac gtt gca aaa tat aac tcc cca act     336
Pro Glu Thr Leu Phe Cys Cys Asp Val Ala Lys Tyr Asn Ser Pro Thr
            100                 105                 110 aat ttc cag ata gat gga aga aat aga aaa gtg att atg gac tta aag     384
Asn Phe Gln Ile Asp Gly Arg Asn Arg Lys Val Ile Met Asp Leu Lys
        115                 120                 125 aca atg gaa aat ctt gga ctt gct caa aat tgt act atc tct att cag     432
Thr Met Glu Asn Leu Gly Leu Ala Gln Asn Cys Thr Ile Ser Ile Gln
    130                 135                 140 gat tat gaa gtt ttt cga tgc gaa gat tca ctg gac gaa aga aag ata     480
Asp Tyr Glu Val Phe Arg Cys Glu Asp Ser Leu Asp Glu Arg Lys Ile
145                 150                 155                 160 aaa ggg gtc att gag ctc agg aag agc tta ctg tct gcc ttg aga act     528
Lys Gly Val Ile Glu Leu Arg Lys Ser Leu Leu Ser Ala Leu Arg Thr
                165                 170                 175 tat gaa cca tat gga tcc ctg gtt caa caa ata cga att ctg ctg ctg     576
Tyr Glu Pro Tyr Gly Ser Leu Val Gln Gln Ile Arg Ile Leu Leu Leu
            180                 185                 190
```

```
ggt cca att gga gct ggg aag tct agc ttt ttc aac tca gtg agg tct    624
Gly Pro Ile Gly Ala Gly Lys Ser Ser Phe Phe Asn Ser Val Arg Ser
            195                 200                 205 gtt ttc caa ggg cat gta acg cat cag gct ttg gtg ggc act aat aca    672
Val Phe Gln Gly His Val Thr His Gln Ala Leu Val Gly Thr Asn Thr
        210                 215                 220 act ggg ata tct gag aag tat agg aca tac tct att aga gac ggg aaa    720
Thr Gly Ile Ser Glu Lys Tyr Arg Thr Tyr Ser Ile Arg Asp Gly Lys
225                 230                 235                 240 gat ggc aaa tac ctg cca ttt att ctg tgt gac tca ctg ggg ctg agt    768
Asp Gly Lys Tyr Leu Pro Phe Ile Leu Cys Asp Ser Leu Gly Leu Ser
                245                 250                 255 gag aaa gaa ggc ggc ctg tgc atg gat gac ata tcc tac atc ttg aac    816
Glu Lys Glu Gly Gly Leu Cys Met Asp Asp Ile Ser Tyr Ile Leu Asn
            260                 265                 270 ggt aac att cgt gat aga tac cag ttt aat ccc atg gaa tca atc aaa    864
Gly Asn Ile Arg Asp Arg Tyr Gln Phe Asn Pro Met Glu Ser Ile Lys
        275                 280                 285 tta aat cat cat gac tac att gat tcc cca tcg ctg aag gac aga att    912
Leu Asn His His Asp Tyr Ile Asp Ser Pro Ser Leu Lys Asp Arg Ile
    290                 295                 300 cat tgt gtg gca ttt gta ttt gat gcc agc tct att gaa tac ttc tcc    960
His Cys Val Ala Phe Val Phe Asp Ala Ser Ser Ile Glu Tyr Phe Ser
305                 310                 315                 320 tct cag atg ata gta aag atc aaa aga att cga agg gag ttg gta aac   1008
Ser Gln Met Ile Val Lys Ile Lys Arg Ile Arg Arg Glu Leu Val Asn
                325                 330                 335 gct ggt gtg gta cat gtg gct ttg ctc act cat gtg gat agc atg gat   1056
Ala Gly Val Val His Val Ala Leu Leu Thr His Val Asp Ser Met Asp
            340                 345                 350 ctg att aca aaa ggt gac ctt ata gaa ata gag aga tgt gtg cct gtg   1104
Leu Ile Thr Lys Gly Asp Leu Ile Glu Ile Glu Arg Cys Val Pro Val
        355                 360                 365 agg tcc aag cta gag gaa gtc caa aga aaa ctt gga ttt gct ctt tct   1152
Arg Ser Lys Leu Glu Glu Val Gln Arg Lys Leu Gly Phe Ala Leu Ser
    370                 375                 380 gac atc tcg gtg gtt agc aat tat tcc tct gag tgg gag ctg gac cct   1200
Asp Ile Ser Val Val Ser Asn Tyr Ser Ser Glu Trp Glu Leu Asp Pro
385                 390                 395                 400 gta aag gat gtt cta att ctt tct gct ctg aga cga atg cta tgg gct   1248
Val Lys Asp Val Leu Ile Leu Ser Ala Leu Arg Arg Met Leu Trp Ala
                405                 410                 415 gca gat gac ttc tta gag gat ttg cct ttt gag caa ata ggg aat cta   1296
Ala Asp Asp Phe Leu Glu Asp Leu Pro Phe Glu Gln Ile Gly Asn Leu
            420                 425                 430 agg gag gaa att atc aac tgt gca caa gga aaa aaa tag               1335
Arg Glu Glu Ile Ile Asn Cys Ala Gln Gly Lys Lys
        435                 440

<210> SEQ ID NO 33
<211> LENGTH: 444
<212> TYPE: PRT
<213> ORGANISM: Pan troglodytes
<220> FEATURE:
<221> NAME/KEY: Variation
<222> LOCATION: 71
<223> OTHER INFORMATION: Xaa= Glu or Ala

<400> SEQUENCE: 33

Met Ala Val Thr Thr Arg Leu Thr Trp Leu His Glu Lys Ile Leu Gln
 1               5                  10                  15
```

```
Asn His Phe Gly Gly Lys Arg Leu Ser Leu Leu Tyr Lys Gly Ser Val
                20                  25                  30

His Gly Phe His Asn Gly Val Leu Leu Asp Arg Cys Cys Asn Gln Gly
            35                  40                  45

Pro Thr Leu Thr Val Ile Tyr Ser Glu Asp His Ile Ile Gly Ala Tyr
        50                  55                  60

Ala Glu Glu Gly Tyr Gln Xaa Arg Lys Tyr Ala Ser Ile Ile Leu Phe
65                  70                  75                  80

Ala Leu Gln Glu Thr Lys Ile Ser Glu Trp Lys Leu Gly Leu Tyr Thr
                85                  90                  95

Pro Glu Thr Leu Phe Cys Cys Asp Val Ala Lys Tyr Asn Ser Pro Thr
            100                 105                 110

Asn Phe Gln Ile Asp Gly Arg Asn Arg Lys Val Ile Met Asp Leu Lys
        115                 120                 125

Thr Met Glu Asn Leu Gly Leu Ala Gln Asn Cys Thr Ile Ser Ile Gln
130                 135                 140

Asp Tyr Glu Val Phe Arg Cys Glu Asp Ser Leu Asp Glu Arg Lys Ile
145                 150                 155                 160

Lys Gly Val Ile Glu Leu Arg Lys Ser Leu Leu Ser Ala Leu Arg Thr
                165                 170                 175

Tyr Glu Pro Tyr Gly Ser Leu Val Gln Gln Ile Arg Ile Leu Leu Leu
            180                 185                 190

Gly Pro Ile Gly Ala Gly Lys Ser Ser Phe Phe Asn Ser Val Arg Ser
        195                 200                 205

Val Phe Gln Gly His Val Thr His Gln Ala Leu Val Gly Thr Asn Thr
210                 215                 220

Thr Gly Ile Ser Glu Lys Tyr Arg Thr Tyr Ser Ile Arg Asp Gly Lys
225                 230                 235                 240

Asp Gly Lys Tyr Leu Pro Phe Ile Leu Cys Asp Ser Leu Gly Leu Ser
                245                 250                 255

Glu Lys Glu Gly Gly Leu Cys Met Asp Asp Ile Ser Tyr Ile Leu Asn
            260                 265                 270

Gly Asn Ile Arg Asp Arg Tyr Gln Phe Asn Pro Met Glu Ser Ile Lys
        275                 280                 285

Leu Asn His His Asp Tyr Ile Asp Ser Pro Ser Leu Lys Asp Arg Ile
290                 295                 300

His Cys Val Ala Phe Val Phe Asp Ala Ser Ser Ile Glu Tyr Phe Ser
305                 310                 315                 320

Ser Gln Met Ile Val Lys Ile Lys Arg Ile Arg Arg Glu Leu Val Asn
                325                 330                 335

Ala Gly Val Val His Val Ala Leu Leu Thr His Val Asp Ser Met Asp
            340                 345                 350

Leu Ile Thr Lys Gly Asp Leu Ile Glu Ile Glu Arg Cys Val Pro Val
        355                 360                 365

Arg Ser Lys Leu Glu Glu Val Gln Arg Lys Leu Gly Phe Ala Leu Ser
370                 375                 380

Asp Ile Ser Val Val Ser Asn Tyr Ser Ser Glu Trp Glu Leu Asp Pro
385                 390                 395                 400

Val Lys Asp Val Leu Ile Leu Ser Ala Leu Arg Arg Met Leu Trp Ala
                405                 410                 415

Ala Asp Asp Phe Leu Glu Asp Leu Pro Phe Glu Gln Ile Gly Asn Leu
            420                 425                 430

Arg Glu Glu Ile Ile Asn Cys Ala Gln Gly Lys Lys
```

<210> SEQ ID NO 34
<211> LENGTH: 1335
<212> TYPE: DNA
<213> ORGANISM: Homo sapiens

<400> SEQUENCE: 34

```
atggcagtga caactcgttt gacatggttg cacgaaaaga tcctgcaaaa tcattttgga      60
gggaagcggc ttagccttct ctataagggt agtgtccatg gattccgtaa tggagttttg     120
cttgacagat gttgtaatca agggcctact ctaacagtga tttatagtga agatcatatt     180
attggagcat atgcagaaga gagttaccag gaaggaaagt atgcttccat catccttttt     240
gcacttcaag atactaaaat ttcagaatgg aaactaggac tatgtacacc agaaacactg     300
ttttgttgtg atgttacaaa atataactcc ccaactaatt tccagataga tggaagaaat     360
agaaaagtga ttatggactt aaagacaatg gaaaatcttg acttgctca aaattgtact      420
atctctattc aggattatga agttttcga tgcgaagatt cactggatga agaaagata      480
aaagggtca ttgagctcag gaagagctta ctgtctgcct tgagaactta tgaaccatat      540
ggatccctgg ttcaacaaat acgaattctc ctcctgggtc aattggagc tcccaagtcc      600
agcttttttca actcagtgag gtctgttttc caagggcatg taacgcatca ggctttggtg     660
ggcactaata caactgggat atctgagaag tataggacat actctattag agacgggaaa     720
gatggcaaat acctgccgtt tattctgtgt gactcactgg ggctgagtga aaagaaggc      780
ggcctgtgca gggatgacat attctatatc ttgaacggta acattcgtga tagataccag     840
tttaatccca tggaatcaat caaattaaat catcatgact acattgattc cccatcgctg     900
aaggacagaa ttcattgtgt ggcatttgta tttgatgcca gctctattca atacttctcc     960
tctcagatga tagtaaagat caaaagaatt caaagggagt tggtaaacgc tggtgtggta    1020
catgtggctt tgctcactca tgtggatagc atggatttga ttacaaaagg tgaccttata    1080
gaaatagaga gatgtgagcc tgtgaggtcc aagctagagg aagtccaaag aaaacttgga    1140
tttgctcttt ctgacatctc ggtggttagc aattattcct ctgagtggga gctggaccct    1200
gtaaaggatg ttctaattct ttctgctctg agacgaatgc tatgggctgc agatgacttc    1260
ttagaggatt tgcctttga gcaaataggg aatctaaggg aggaaattat caactgtgca    1320
caaggaaaaa aatag                                                     1335
```

<210> SEQ ID NO 35
<211> LENGTH: 1335
<212> TYPE: DNA
<213> ORGANISM: Homo sapiens
<220> FEATURE:
<221> NAME/KEY: CDS
<222> LOCATION: (1)..(1335)

<400> SEQUENCE: 35

```
atg gca gtg aca act cgt ttg aca tgg ttg cac gaa aag atc ctg caa       48
Met Ala Val Thr Thr Arg Leu Thr Trp Leu His Glu Lys Ile Leu Gln
  1               5                  10                  15 aat cat ttt gga ggg aag cgg ctt agc ctt ctc tat aag ggt agt gtc       96
Asn His Phe Gly Gly Lys Arg Leu Ser Leu Leu Tyr Lys Gly Ser Val
             20                  25                  30 cat gga ttc cgt aat gga gtt ttg ctt gac aga tgt tgt aat caa ggg      144
His Gly Phe Arg Asn Gly Val Leu Leu Asp Arg Cys Cys Asn Gln Gly
         35                  40                  45
```

```
cct act cta aca gtg att tat agt gaa gat cat att att gga gca tat        192
Pro Thr Leu Thr Val Ile Tyr Ser Glu Asp His Ile Ile Gly Ala Tyr
    50                  55                  60 gca gaa gag agt tac cag gaa gga aag tat gct tcc atc atc ctt ttt        240
Ala Glu Glu Ser Tyr Gln Glu Gly Lys Tyr Ala Ser Ile Ile Leu Phe
 65                  70                  75                  80 gca ctt caa gat act aaa att tca gaa tgg aaa cta gga cta tgt aca        288
Ala Leu Gln Asp Thr Lys Ile Ser Glu Trp Lys Leu Gly Leu Cys Thr
                 85                  90                  95 cca gaa aca ctg ttt tgt tgt gat gtt aca aaa tat aac tcc cca act        336
Pro Glu Thr Leu Phe Cys Cys Asp Val Thr Lys Tyr Asn Ser Pro Thr
            100                 105                 110 aat ttc cag ata gat gga aga aat aga aaa gtg att atg gac tta aag        384
Asn Phe Gln Ile Asp Gly Arg Asn Arg Lys Val Ile Met Asp Leu Lys
        115                 120                 125 aca atg gaa aat ctt gga ctt gct caa aat tgt act atc tct att cag        432
Thr Met Glu Asn Leu Gly Leu Ala Gln Asn Cys Thr Ile Ser Ile Gln
130                 135                 140 gat tat gaa gtt ttt cga tgc gaa gat tca ctg gat gaa aga aag ata        480
Asp Tyr Glu Val Phe Arg Cys Glu Asp Ser Leu Asp Glu Arg Lys Ile
145                 150                 155                 160 aaa ggg gtc att gag ctc agg aag agc tta ctg tct gcc ttg aga act        528
Lys Gly Val Ile Glu Leu Arg Lys Ser Leu Leu Ser Ala Leu Arg Thr
                165                 170                 175 tat gaa cca tat gga tcc ctg gtt caa caa ata cga att ctc ctc ctg        576
Tyr Glu Pro Tyr Gly Ser Leu Val Gln Gln Ile Arg Ile Leu Leu Leu
            180                 185                 190 ggt cca att gga gct ccc aag tcc agc ttt ttc aac tca gtg agg tct        624
Gly Pro Ile Gly Ala Pro Lys Ser Ser Phe Phe Asn Ser Val Arg Ser
        195                 200                 205 gtt ttc caa ggg cat gta acg cat cag gct ttg gtg ggc act aat aca        672
Val Phe Gln Gly His Val Thr His Gln Ala Leu Val Gly Thr Asn Thr
210                 215                 220 act ggg ata tct gag aag tat agg aca tac tct att aga gac ggg aaa        720
Thr Gly Ile Ser Glu Lys Tyr Arg Thr Tyr Ser Ile Arg Asp Gly Lys
225                 230                 235                 240 gat ggc aaa tac ctg ccg ttt att ctg tgt gac tca ctg ggg ctg agt        768
Asp Gly Lys Tyr Leu Pro Phe Ile Leu Cys Asp Ser Leu Gly Leu Ser
                245                 250                 255 gag aaa gaa ggc ggc ctg tgc agg gat gac ata ttc tat atc ttg aac        816
Glu Lys Glu Gly Gly Leu Cys Arg Asp Asp Ile Phe Tyr Ile Leu Asn
            260                 265                 270 ggt aac att cgt gat aga tac cag ttt aat ccc atg gaa tca atc aaa        864
Gly Asn Ile Arg Asp Arg Tyr Gln Phe Asn Pro Met Glu Ser Ile Lys
        275                 280                 285 tta aat cat cat gac tac att gat tcc cca tcg ctg aag gac aga att        912
Leu Asn His His Asp Tyr Ile Asp Ser Pro Ser Leu Lys Asp Arg Ile
290                 295                 300 cat tgt gtg gca ttt gta ttt gat gcc agc tct att caa tac ttc tcc        960
His Cys Val Ala Phe Val Phe Asp Ala Ser Ser Ile Gln Tyr Phe Ser
305                 310                 315                 320 tct cag atg ata gta aag atc aaa aga att caa agg gag ttg gta aac       1008
Ser Gln Met Ile Val Lys Ile Lys Arg Ile Gln Arg Glu Leu Val Asn
                325                 330                 335 gct ggt gtg gta cat gtg gct ttg ctc act cat gtg gat agc atg gat       1056
Ala Gly Val Val His Val Ala Leu Leu Thr His Val Asp Ser Met Asp
            340                 345                 350 ttg att aca aaa ggt gac ctt ata gaa ata gag aga tgt gag cct gtg       1104
Leu Ile Thr Lys Gly Asp Leu Ile Glu Ile Glu Arg Cys Glu Pro Val
        355                 360                 365
```

```
agg tcc aag cta gag gaa gtc caa aga aaa ctt gga ttt gct ctt tct      1152
Arg Ser Lys Leu Glu Glu Val Gln Arg Lys Leu Gly Phe Ala Leu Ser
    370                 375                 380 gac atc tcg gtg gtt agc aat tat tcc tct gag tgg gag ctg gac cct      1200
Asp Ile Ser Val Val Ser Asn Tyr Ser Ser Glu Trp Glu Leu Asp Pro
385                 390                 395                 400 gta aag gat gtt cta att ctt tct gct ctg aga cga atg cta tgg gct      1248
Val Lys Asp Val Leu Ile Leu Ser Ala Leu Arg Arg Met Leu Trp Ala
            405                 410                 415 gca gat gac ttc tta gag gat ttg cct ttt gag caa ata ggg aat cta      1296
Ala Asp Asp Phe Leu Glu Asp Leu Pro Phe Glu Gln Ile Gly Asn Leu
        420                 425                 430 agg gag gaa att atc aac tgt gca caa gga aaa aaa tag                  1335
Arg Glu Glu Ile Ile Asn Cys Ala Gln Gly Lys Lys
    435                 440
```

<210> SEQ ID NO 36
<211> LENGTH: 444
<212> TYPE: PRT
<213> ORGANISM: Homo sapiens

<400> SEQUENCE: 36

```
Met Ala Val Thr Thr Arg Leu Thr Trp Leu His Glu Lys Ile Leu Gln
1               5                   10                  15

Asn His Phe Gly Gly Lys Arg Leu Ser Leu Leu Tyr Lys Gly Ser Val
                20                  25                  30

His Gly Phe Arg Asn Gly Val Leu Leu Asp Arg Cys Cys Asn Gln Gly
            35                  40                  45

Pro Thr Leu Thr Val Ile Tyr Ser Glu Asp His Ile Ile Gly Ala Tyr
        50                  55                  60

Ala Glu Glu Ser Tyr Gln Glu Gly Lys Tyr Ala Ser Ile Ile Leu Phe
65                  70                  75                  80

Ala Leu Gln Asp Thr Lys Ile Ser Glu Trp Lys Leu Gly Leu Cys Thr
                85                  90                  95

Pro Glu Thr Leu Phe Cys Cys Asp Val Thr Lys Tyr Asn Ser Pro Thr
            100                 105                 110

Asn Phe Gln Ile Asp Gly Arg Asn Arg Lys Val Ile Met Asp Leu Lys
        115                 120                 125

Thr Met Glu Asn Leu Gly Leu Ala Gln Asn Cys Thr Ile Ser Ile Gln
130                 135                 140

Asp Tyr Glu Val Phe Arg Cys Glu Asp Ser Leu Asp Glu Arg Lys Ile
145                 150                 155                 160

Lys Gly Val Ile Glu Leu Arg Lys Ser Leu Leu Ser Ala Leu Arg Thr
                165                 170                 175

Tyr Glu Pro Tyr Gly Ser Leu Val Gln Gln Ile Arg Ile Leu Leu Leu
            180                 185                 190

Gly Pro Ile Gly Ala Pro Lys Ser Ser Phe Phe Asn Ser Val Arg Ser
        195                 200                 205

Val Phe Gln Gly His Val Thr His Gln Ala Leu Val Gly Thr Asn Thr
210                 215                 220

Thr Gly Ile Ser Glu Lys Tyr Arg Thr Tyr Ser Ile Arg Asp Gly Lys
225                 230                 235                 240

Asp Gly Lys Tyr Leu Pro Phe Ile Leu Cys Asp Ser Leu Gly Leu Ser
                245                 250                 255

Glu Lys Glu Gly Gly Leu Cys Arg Asp Asp Ile Phe Tyr Ile Leu Asn
            260                 265                 270
```

-continued

```
Gly Asn Ile Arg Asp Arg Tyr Gln Phe Asn Pro Met Glu Ser Ile Lys
            275                 280                 285

Leu Asn His His Asp Tyr Ile Asp Ser Pro Ser Leu Lys Asp Arg Ile
            290                 295                 300

His Cys Val Ala Phe Val Phe Asp Ala Ser Ser Ile Gln Tyr Phe Ser
305                 310                 315                 320

Ser Gln Met Ile Val Lys Ile Lys Arg Ile Gln Arg Glu Leu Val Asn
                325                 330                 335

Ala Gly Val Val His Val Ala Leu Leu Thr His Val Asp Ser Met Asp
                340                 345                 350

Leu Ile Thr Lys Gly Asp Leu Ile Glu Ile Glu Arg Cys Glu Pro Val
            355                 360                 365

Arg Ser Lys Leu Glu Glu Val Gln Arg Lys Leu Gly Phe Ala Leu Ser
            370                 375                 380

Asp Ile Ser Val Val Ser Asn Tyr Ser Ser Glu Trp Glu Leu Asp Pro
385                 390                 395                 400

Val Lys Asp Val Leu Ile Leu Ser Ala Leu Arg Arg Met Leu Trp Ala
                405                 410                 415

Ala Asp Asp Phe Leu Glu Asp Leu Pro Phe Glu Gln Ile Gly Asn Leu
                420                 425                 430

Arg Glu Glu Ile Ile Asn Cys Ala Gln Gly Lys Lys
            435                 440
```

What is claimed is:

1. A method for identifying an agent that increases human or chimpanzee p44 function, comprising:
   (i) contacting at least one candidate agent with a p44 polypeptide selected from the group consisting of:
      (a) a human p44 polypeptide comprising SEQ ID NO:36;
      (b) a polypeptide encoded by a polynucleotide comprising SEQ ID NO:34;
      (c) a chimpanzee p44 polypeptide comprising SEQ ID NO:33;
      (d) a polypeptide encoded by a polynucleotide comprising SEQ ID NO:31;
      (e) a polypeptide encoded by a polynucleotide comprising nucleotides 1-457 of SEQ ID NO:34 or SEQ ID NO:31; and
      (f) a polypeptide, having a p44 function, having at least one amino acid change at positions 36, 68, 71, 72, 84, 95, and 106, but is otherwise identical to SEQ ID NO:36 or SEQ ID NO:34; and
   (ii) detecting a p44 polypeptide function,
      wherein said agent is identified by its ability to increase the human or chimpanzee p44 polypeptide function relative to the function of the p44 polypeptide in the absence of the candidate agent, and wherein the p44 function is selected from the group consisting of microtubule assembly and resistance to HCV infection.

2. The method of claim 1 wherein the p44 polypeptide function to be increased is human.

3. The method of claim 2 wherein the increase of the p44 function results in a human function that is more similar to a chimpanzee p44 function.

4. The method of claim 2 wherein said p44 polypeptide is encoded by a p44 exon 2 polynucleotide comprising nucleotides 1-457 of SEQ ID NO:34.

5. The method of claim 2 wherein said candidate agent is a small molecule that forms a complex with human p44 that mimics the three-dimensional structure of the chimpanzee p44, whereby the human p44 function is increased.

6. The method of claim 2 wherein said candidate agent is a small molecule that interacts with human p44 amino acids so as to increase the human p44 polypeptide function.

7. The method of claim 2, wherein said candidate agent is a small molecule that interacts with at least one human p44 amino acid selected from the group consisting of Arg36, Ser68, Glu71, Gly72, Asp84, Cys95, and Thr106 of SEQ ID NO:36.

8. A method for identifying an agent that decreases susceptibility to a human's hepatitis C virus (HCV) infection, comprising:
   (i) contacting at least one candidate agent with a p44 polypeptide capable of decreasing susceptibility to a human's HCV infection selected from the group consisting of:
      (a) a human p44 polypeptide comprising SEQ ID NO:36;

(b) a polypeptide encoded by a polynucleotide comprising SEQ ID NO:34;
(c) a polypeptide encoded by a polynucleotide comprising nucleotides 1-457 of SEQ ID NO:34; and
(d) a polypeptide having a p44 function, having at least one amino acid change at positions 36, 38, 71, 72, 84, 95, and 106, but is otherwise identical to SEQ ID NO:34; and (ii) detecting susceptibility to HCV infection in in vitro hepatocytes or in vivo animal model, wherein said agent is identified by its ability to decrease susceptibility to HCV infection relative to the susceptibility to HCV infection in the absence of the candidate agent.

9. The method of claim 1, wherein increased microtubule assembly is detected via antibody detection of enhanced p44 assembly into microtubules in cultured hepatocytes.

10. The method of claim 1, wherein increased resistance to HCV infection is detected via decreased viral titer in in vitro hepatocytes or an in vivo animal model.

* * * * *